US006288302B1

(12) United States Patent
Yu et al.

(10) Patent No.: US 6,288,302 B1
(45) **Date of Patent: *Sep. 11, 2001**

(54) APPLICATION OF α-AMYLASE GENE PROMOTER AND SIGNAL SEQUENCE IN THE PRODUCTION OF RECOMBINANT PROTEINS IN TRANSGENIC PLANTS AND TRANSGENIC PLANT SEEDS

(75) Inventors: Su-May Yu; Li-Fei Liu; Ming-Tsair Chan, all of Taipei (TW)

(73) Assignee: National Science Council of R.O.C., Taipei City (TW)

( * ) Notice: Subject to any disclaimer, the term of this patent is extended or adjusted under 35 U.S.C. 154(b) by 0 days.

This patent is subject to a terminal disclaimer.

(21) Appl. No.: 09/072,917

(22) Filed: May 4, 1998

Related U.S. Application Data

(63) Continuation of application No. 08/947,201, filed on Oct. 8, 1997, now abandoned, which is a continuation of application No. 08/509,962, filed on Aug. 1, 1995, now abandoned, which is a continuation-in-part of application No. 08/343,380, filed on Nov. 22, 1994, now Pat. No. 5,712,112, which is a continuation of application No. 07/973,324, filed on Nov. 4, 1992, now Pat. No. 5,460,952.

(51) Int. Cl.[7] .......................... C12N 15/29; C12N 15/82; C12N 15/84; A01H 4/00

(52) U.S. Cl. .......................... 800/287; 800/278; 800/294; 800/320; 800/320.2; 800/69.1; 800/69.8; 800/204; 800/429; 800/468; 800/469

(58) Field of Search .................................... 800/278, 279, 800/287, 288, 292, 293, 294, 298, 320, 320.2, 320.3; 435/69.1, 468, 469, 470, 69.8, 204, 205, 429

(56) References Cited

U.S. PATENT DOCUMENTS

| | | | |
|---|---|---|---|
| 5,460,952 | 10/1995 | Yu et al. | 435/69.1 |
| 5,677,474 | 10/1997 | Rogers | 800/205 |
| 5,693,506 | 12/1997 | Rodriguez | 435/172.3 |
| 5,712,112 | 1/1998 | Yu et al. | 435/69.1 |

FOREIGN PATENT DOCUMENTS

| | | |
|---|---|---|
| 0 486 233 A2 | 5/1992 | (EP) . |
| WO 91/05054 | 4/1991 | (WO) . |

OTHER PUBLICATIONS

Reynolds et al. Plant Mol. Biol. 29: 885–896, 1995.*

Gould et al. J. Cell. Biochem. Suppl. 16F:207, 1992.*

Chan et al. Plant Mol. Biol. 22:491–546, 1993.*

Simmons et al., "Synthesis and Secretion of α–Amylase by Rice Callus: Evidence for Differential Gene Expression," *Biotechnology and Bioengineering*, 38:545–551 (1991).

Yu et al., "Sugars act as signal molecules and osmotica to regulate the expression of α–amylase genes and metabolic activities in germinating cereal grains," *Plant Molecular Biology*, 30:1277–1289 (1996).

Akazawa, T. et al., "Topographic Aspects of Biosynthesis, Extracellular Secretion, and Intracellular Storage of Proteins in Plant Cells," *Ann. Rev. Psychol.*, 36:441–472 (1985).

An, G. et al., "Transformation of Tobacco, Tomato, Potato, and *Arabidopsis thaliana* Using a Binary Ti Vector System," *Plant Physiol.*, 81:301–305 (1986).

Ashikari, T. et al., "Rhizopus Raw–Starch–Degrading Glucoamylase: Its Cloning and Expression in Yeast," *Agric. Biol. Chem.*, 50(4):957–964 (1986).

Baulcombe, D.C. et al., "A novel wheat α–amylase gene (α–*Amy3*)," *Mol. Gen. Genet.*, 209:33–40 (1987).

Belanger, F.C. et al., "Heat shock causes destabilization of specific mRNAs and destruction of endoplasmic reticulum in barley aleurone cells," *Proc. Nat'l Acad. Sci., USA*, 83:1354–1358 (Mar., 1986).

Benfey, P.N. et al., "The CaMV 35S enhancer contains at least two domains which can confer different development and tissue–specific expression patterns," *EMBO J.*, 8(8):2195–2202 (1989).

Bevan, M., "Binary *Agrobacterium* vectors for plant transformation," *Nucleic Acids Research.*, 12(22):8711–8721 (1984).

Briggs, D.E., "Barley Germination: Biochemical Changes and Hormonal Conrol," *Genetics, Biochemistry, Molecular Biology & Biotechnology*, Shewry, P.R., (ed.), C.A.B. International, UK, pp. 369–401 (1992).

Bytebier, B. et al., "T–DNA organization in tumor cultures and transgenic plants of the monocotyledon *Asparagus officinalis,*" *Proc. Nat'l Acad. Sci., USA*, 84:5345–5349 (Aug., 1987).

Chan et al., "Novel Gene Expression System for Plant Cells Based on Induction of α–Amylase Promoter by Carbohydrate Starvation," *The Journal of Biological Chemistry*, 269(26):17635–17641 (Jul. 1, 1994).

(List continued on next page.)

*Primary Examiner*—David T. Fox
(74) *Attorney, Agent, or Firm*—Marshall, O'Toole, Gerstein, Murray & Borun

(57) ABSTRACT

Disclosed is a method for producing a transgenic angiosperm plant, particularly a monocot, comprising the step of transforming an immature embryo of an angiosperm plant with a DNA fragment expressible in said angiosperm embryo, said DNA fragment comprising a promoter region derived from an α-amylase gene of a plant, and an exogenous gene encoding a desired gene product, said promoter region being inducible under a sugar-depleted or sugar-free condition to promote the expression of said gene, whereby at least a part of the resultant transgenic angiosperm plant has the ability to express said gene product. Transgenic angiosperm plants and transgenic angiosperm plant seeds are also disclosed. The transgenic angiosperm plant seeds may have application in the industrial production of alcohol, beer, glucose and the like.

6 Claims, 42 Drawing Sheets

(7 of 42 Drawing Sheet(s) Filed in Color)

OTHER PUBLICATIONS

Chan, M–T et al., "Transformation of Indica Rice (*Oryza sativa* L.) Mediated by *Agrobacterium tumefaciens," Plant Cell Physiol.*, 33(5):577–583 (1992).

Chandler, P.M. et al., "The effects of gibberellic acid and a bscisic acid on α–amylase mRNA levels in barley aleurone layers studies using an α–amylase cDNA clone," *Plant Molecular Biology*, 3:407–418 (1984).

Chang, H–H et al., "*Agrobacterium tumefaciens*–mediated transformation of soybean (*Glycine max* (L.) Merr.) is promoted by the inclusion of potato suspension culture," *Bot. Bull. Academia Sinica*, 32:171–178 (1991).

Christou, P. et al., "The development of a variety–independent gene–transfer method for rice," *Tibtech*, 10:239–246 (Jul., 1992).

Christou, P. et al., "Production of Transgenic Rice (*Oryza Sativa* L.) Plants From Agronomically Important Indica and Japonica Varieties via Electric Discharge Particle Acceleration of Exogenous DNA into Immature Zygotic Embryos," *Bio/Technology*, 9:957–962 (Oct., 1991).

Dale et al., "Agroinfection of Wheat: Inoculation of In Vitro Grown Seedlings and Embryos," *Plant Science*, 63:237–245 (1989).

Datta, S.K. et al., "Genetically Engineered Fertile Indica–Rice Recovered From Protoplasts," *Bio/Technology*, 8:736–740 (Aug., 1990).

Deikman, J. et al., "Control of α–Amylase mRNA Accumulation by Gibberellic Acid and Calcium in Barley Aleurone Layers," *Plant Physiol.*, 78:192–198 (1985).

Depicker, A. et al., "Molecular Cloning of Overlapping Segments of the Nonpaline Ti–Plasmid pTiC58 as a Means to Restriction Endonuclease Mapping," *Plasmid*, 3:193–211 (1980).

Düring, K. et al., "Synthesis and self–assembly of a functional monoclonal antibody in transgenic *Nicotiana tabacum", Plant Molecular Biology*, 15:281–293 (1990).

Firek et al., "Secretion of a functional single–chain Fv protein in transgenic tobacco plants and cell suspension cultures," *Plant Molecular Biology*, 23:861–870 (1993).

Garfinkel, D.J. et al., "*Agrobacterium tumefaciens* Mutants Affected in Crown Gall Tumorigenesis and Octopine Catabolism," *J. Bacteriology*, 144(2):732–743 (Nov., 1980).

Gillies, S.D. et al., "A Tissue–specific Transcription Enhancer Element is Located in the Major Intron of a Rearranged Immunoglobulin Heavy Chain Gene," *Cell*, 33:717–728 (Jul., 1983).

Gould, J. et al., "Transformation of *Zea mays* L. Using *Agrobacterium tumefaciens* and the Shoot Apex," *Plant Physiol.*, 95:426–434 (1991).

Hain, R. et al., "Uptake, integration, expression and genetic transmission of a selectable chimaeric gene by plant protoplasts," *Mol Gen. Genet.*, 199:161–168 (1985).

Hernalsteens, J–P et al., "An Agrobacterium–transformed cell culture from the monocot *Asparagus officinalis*,"*EMBO J.*, 3(13):3039–3041 (1984).

Hiatt, A. et al., "Production of antibodies in transgenic plants," *Nature*, 342:76–78 (Nov. 2, 1989).

Ho, T.D. et al., "Regulation of Gene Expression in Barley Aleurone Layers," *Molecular Biology Plant Growth Control*, Alan R. Liss, Inc., pp. 35–49 (1987).

Holsters, M. et al., "Transfection and Transformation of *Agrobacterium tumefaciens," Mol. Gen. Genet.*, 163:181–187 (1978).

Hooykaas, P.J.J., "Transformation of plant cells via *Agrobacterium," Plant Molecular Biology*, 13:327–336 (1989).

Horsch, R.B. et al., "A Simple and General Method for Transferring Genes into Plants," *Science*, 227:1229–1231 (Mar., 1985).

Huang, N. et al., "Structural organization and differential expression of rice α–amylase genes," *Nucleic Acids Research*, 18(23):7007–7014 (1990).

Huang, N. et al., "Classification and characterization of the rice α–amylase multigene family," *Plant Molecular Biology*, 14:655–668 (1990).

Itoh et al., "Developmental and Hormonal Regulation of Rice α–Amylase (RA*mylA*)–*gusA* Fusion Genes in Transgenic Rice Seeds," *Plant Physiol.*, 107:25–31 (1995).

Janssens, A. et al., "Plant Cells Induce Transcription of the *Agrobacterium Tumefaciens* Noplaine pTiC58 Virulence Region," *Plant Science*, 47:185–193 (1986).

Johnson, J.W. et al., "Glycine potentiates the NMDA response in cultured mouse brain neurons," *Nature*, 325:529–531 (Feb., 1987).

Karrer, E.E. et al., "Differential expression of α–amylase genes in germinating rice and barley seeds," *Plant Molecular Biology*, 16:797–805 (1991).

Khursheed, B. et al., "Barley α–Amylase Genes," *J. Biological Chemistry*, 263(35):18953–18960 (Dec. 15, 1988).

Kim, J–K et al., "Nucleotide sequence of a high–pI rice (*Oryza sativa*)–amylase gene," *Plant Molecular Biology*, 18:399–402 (1992).

Knox, C.A.P. et al., "Structure and organization of two divergent α–amylase genes from barley," *Plant Molecular Biology*, 9:3–17 (1987).

Krebbers, E. et al., "Production of peptides in plant seeds," *Tibtech.*, 8:1–3 (Jan., 1990).

Kumagai, M.H. et al., "Expression and secretion of rice α–amylase by *Saccharomyces cereviae," Gene*, 94:209–216 (1990).

Lanahan, M.B. et al., "Gibberellin Response Complex in Cereal α–Amylase Gene Promoters," *Plant Cell*, 4:203–211 (Feb., 1992).

Li, B–J et al., "Studies on Introduction of Foreign Genes into Cultured Cells of Oryza–Sativa Indica Using Agrobacterium Ti Plasmid System," *Sci China Ser B Chem Life Sci Earth Sci*, 34(1):54–63 (1991) (Abstract Only).

McElroy et al., "Foreign gene expression in transgenic cereals," *Tibtech*, 12:62–68 (Feb., 1994).

McElroy et al., "What's Brewing in Barley Biotechnology?" *Bio/Technology*, 13:245–249 (Mar. 13, 1995).

McElroy, D. et al., "Structural characterization of a rice actin gene," *Plant Molecular Biology*, 14:163–171 (1990).

O'Neil, S. et al., "The α–amylase genes in *Oryza sativa*: Characterization of cDNA clones and mRNA expression during seed germination," *Mol. Gen. Genet.*, 221:235–244 (1990).

Pen, J. et al., "Production of Active *Bacillus Licheniformis* Alpha–Amylase in Tobacco and its Application in Starch Liquefaction," *Bio/Technology*, 10:292–296 (Mar., 1992).

Pen et al., "Phytase–containing Transgenic Seeds as a Novel Feed Additive for Improved Phosphorus Utilization," *Bio/Technology*, 11:811–814 (Jul., 1993).

Radke, S.E. et al., "Transformation of *Brassica napus* L. Using *Agrobacterium tumefaciens*: developmentally regulated expression of a retintroduced napin gene," *Theor. Appl. Genet.*, 75:685–694 (1988).

Raineri, D.M. et al., "Agrobacterium–Mediated Transformation of Rice (*Oryza Sativa* L.)," *Bio/Technology*, 8:33–38 (Jan., 1990).

Rogers, J.C. "Two Barley α–Amylase Gene Families are Regulated Differentially in Aleurone Cells," *J. Biological Chemistry*, 260(6):3731–3738 (Mar. 25, 1985).

Rogers, J.C. et al., "Coordinate Increase in Major Transcripts from the High pI α–Amylase Multigene Family in Barley Aleurone Cells Stimulated with Gibberellic Acid," *J. Biological Chemistry*, 259(19):12234–12240 (Oct. 10, 1984).

Sahi, S.V. et al., "Corn metabolites affect growth and virulence of *Agrobacterium tumefaciens*," *Proc. Nat'l Acad. Sci., USA*, 87:3879–3883 (May, 1990).

Salisbury, F.B. et al., (eds.), "Respiration," *Plant Physiology*, Second Edition, Wadsworth Publishing Company, Inc., Belmont, California, Chapter 2, pp. 174–177 (1978).

Schäfer, W. et al., "T–DNA integration and expression in a monocot crop plant after induction of *Agrobacterium*," *Nature*, 327:529–532 (Jun., 1987).

Schläppi, M. et al., "Competence of Immature Maize Embryos for Agrobacterium–Mediated Gene Transfer," *Plant Cell*, 4:7–16 (Jan., 1992).

Sheu, J–J et al., "Carbohydrate Starvation Stimulates Differential Expression of Rice α–Amylase Genes That is Modulated through Complicated Transcriptional and Posttranscriptional Processes," *J. Biological Chemistry*, 271(43):26998–27004 (1996).

Shimamoto, K. et al., "Fertile transgenic rice plants regenerated from transformed protoplasts," *Nature*, 338:274–276 (1989).

Shimamoto, K., "Expression and Regulation of Monocot Promoters in Transgenic Rice Plants," *In Vitro* 27 (3, pt.2):57 A (1991) Abstract 86).

Sijmons, P.C. et al., "Production of Correctly Processed Human Serum Albumin in Transgenic Plants," *Bio/Technology*, 8:217–221 (Mar. 1990).

Stachel, S.E. et al., "Identification of the signal molecules produced by wounded plant cells that activate T–DNA transfer in *Agrobacterium tumefaciens*," *Nature*, 318:624–629 (Dec., 1985).

Sutliff, T.D. et al., "Characterization of an α–amylase multigene cluster in rice," *Plant Molecular Biology*, 16:579–591 (1991).

Ueda, S. "Fungal glucoamylases and raw starch digestion," *Tibs*, pp. 89–90 (Mar., 1981).

Usami, S. et al., "Factor inducing *Agrobacterium tumefaciens* vir gene expression is present in monocotyledonous plants," *Proc. Nat'l Acad. Sci., USA*, 85:3748–3752 (Jun., 1988).

Vandekerckhove, J. et al., "Enkephalins Produced in Transgenic Plants Using Modified 2S Seed Storage Proteins," *Bio/Technology*, 7:929–932 (Sep., 1989).

Wandelt, C.I. et al., "Vicilin with carboxy–terminal KDEL is retained in the endoplasmic reticulum and accumulates to high levels in the leaves of transgenic plants," *Plant J.*, 2(2):181–192 (1992).

Weiher, H. et al., "Multiple Point Mutations Affecting the Simian Virus 40 Enhancer," *Science*, 219:626–631 (Feb., 1983).

Yasuda, T. et al., "Analogues of Phenoxyacetic Acid and the Generation of Calluses from Seeds of Indica Rice," *Plant Cell Physiology*, 31:763–766 (1990).

Yu, S–M et al., "Metabolic Derepression of α–Amylase Gene Expression in Suspension–cultured Cells of Rice," *J. Biological Chemistry*, 266(31):21131–21137 (Nov. 5, 1991).

Yu et al., "Regulation of α–amylase–encoding gene expression in germinating seeds and cultured cell of rice," *Gene*, 122:247–253 (1992).

Zaenen, I. et al., "Supercoiled Circular DNA in Crown–gall Inducing *Agrobacterium* Strains," *J. Mol. Biol.*, 86:109–127 (1974).

Zheng, K–L et al., "Somatic cell culture of rice cultivars with different grain types: Somaclonal variation in some grain and quality characters," *Plant Cell, Tissue and Organ Culture*, 18:201–208 (1989).

* cited by examiner

```
                    1                                                          60
αAmy6-C         GGATCCATG*G******C****G*C******A*G*CGC****A*G*AA****CA*C****CC****GG
αAmy8-C         ********C*G*G*CAG**G**G*CGC****A*G*AA****CA*C****CC****GG
αAmy7-C         ********C*G*G*C*******G*C******CGT****A*G*A****CA*C*TC****CC*****G
αAmy10-C        ********C*G*G*C*******G*C******CGT****A*G*A****CA*C*TC****CC*****G

                   61                                                         120
αAmy6-C         TGATCGATGATAAGGTCATAACAAAGATTGGGACACGGTATGACGTGGGCAACTTAATCC
αAmy8-C         ********C*GC****G*C**C****C*C****C*GA****C****CC**GGGA*C****
αAmy7-C         A*******G*******G*C*******AC**A**C****A**A*C****C*C*C*****
αAmy10-C        A*******C*GA****G*C*******C*AG**C****AG**A*C****C*AGC**C*C***

                  121                                                         180
αAmy6-C         CGTCAGACTTCCATGTCGTTGCTCACGGCAACAATTACTGCATTTGGGAAAAGAGCGGTC
αAmy8-C         ****C*******G********G*********C****G*C******G*C*****GAA*---
αAmy7-C         *CGA**G*****G********G*******C****TG*TGGC***GCA**C*****G**---
αAmy10-C        *CGA**G*****G********G*******C****T*TG**GGC****GCAG*C**G**---

                  181                                                         240
αAmy6-C         TCAGAGTTCCTGCTGAGGCGGCACCACTATTAGGCGAAGAAAATTTTCAGACTATTGG
αAmy8-C         ****G******C****TA*AA*G*****TAGCTTT**CT*TAGCGATC*AGT*GCA***
αAmy7-C         ------AAT*TGA***CACGATGACGAGACTCAGTTTAGCAGATTT*ACC*GC*A
αAmy10-C        ------AAT*TGA****TGGAGAGGCACAATT*GC*G*T***A*TTACCTGCAATTT
                        "PstI"
```

FIG. 1A

```
           241                                                          300
αAmy6-C    TGCCTGGAA---TAAGATTTGAATTATATCCTAAATAACCAG--------ATTATGATTGT
αAmy8-C    ***T*T*C*ACCCT****AAT*TA****CGTACGTGGCT*TA--------GC*****A*CA
αAmy7-C    *TTT*ACCCTGACCG*TA*ACGTA****CGTGCCGGC*A*GA--------GCTG*ATCC*A
αAmy10-C   *TTCCACCCTCGACGT*TAAC*TA**C**GTG*TGGC*A*GAGTTGTATGC*G*ATC**A

           301                                                          360
αAmy6-C    ATGAGATTTCTTAATCTGAGCAAAGCGTTGAGCATTGCTC---CGATATTTCTATGTATT
αAmy8-C    TGC*AT***GC*GCGAGAT*TGT*CGAGC****T*C*A**GATGT*CGC***GT*AT*AC
αAmy7-C    TCCGA***A*GG*TG*AATTGTCCA**AA*TA*T*CCTC*GTAAATAAAG*GAGGA*CAG
αAmy10-C   TCTGA*C*ATG**CG*GATTGTCCA*AAA*TA*TACCTC*GTAAATAAAG*GAGGA***G
                                         "ScaI"  "PvuI"

           361                                                          420
αAmy6-C    CTACCTGCCTGGGGATATGATATTTGTATCCTCTAGAAGTAAAGATGATTTTAACTC(A)n
αAmy8-C    TAG*G*T*T*C**A*ATAAG**AGC*G*ATG*ACCCTGT***TCC**CAGAA*TG*AGGA
αAmy7-C    GG**A*ACA*TT*T**GGTT*TACGAATAATG***TGCAAT**A**TTGCACTG**TAAT
αAmy10-C   GA**A***G*TT*C**GCATGG***T(A)n

           421                                   458
αAmy8-C    TGAATGGAATTAACTAGCTACTGTTCGTTTCGATCCTC(A)n
αAmy7-C    GCTTAT*C***TTTGCTTGGT*C(A)n
```

FIG. 1B

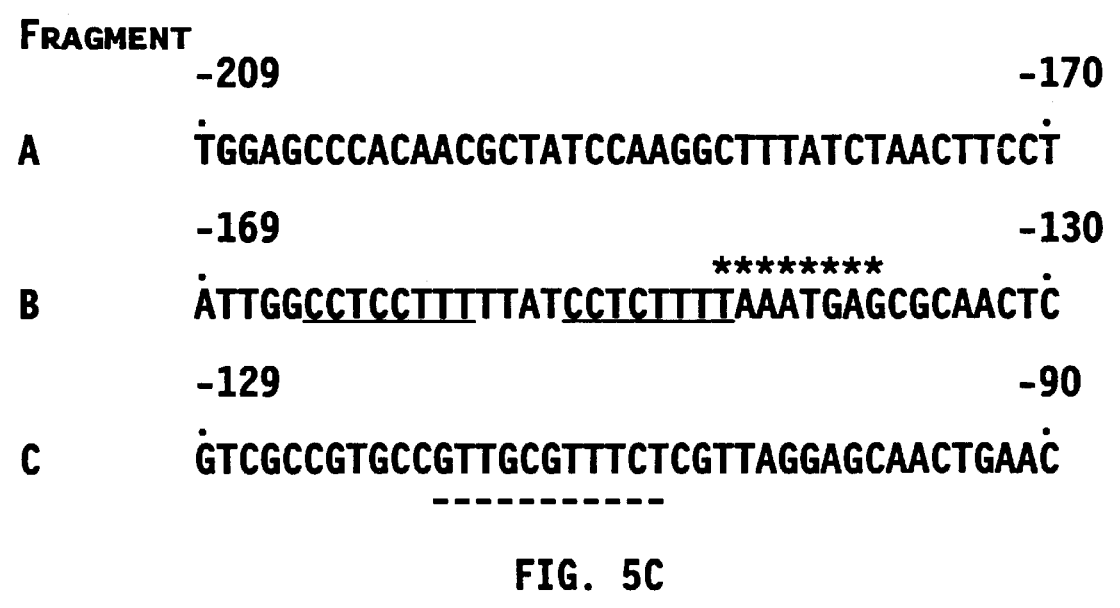

FRAGMENT

```
           -209                                      -170
A          TGGAGCCCACAACGCTATCCAAGGCTTTATCTAACTTCCT

           -169                              *******  -130
B          ATTGGCCTCCTTTTTATCCTCTTTTAAATGAGCGCAACTC

           -129                                      -90
C          GTCGCCGTGCCGTTGCGTTTCTCGTTAGGAGCAACTGAAC
                     -----------
```

FIG. 5C

```
αAmy7-C    GATCCACCCG GCGAGCGAGC TGCGCATCAT GGAAGCTGAC
αAmy10-C   ********** ********** ****T***** ***G******
αAmy8-C    ******TG** *A****AC** **GA****C* CA*G**C**G
αAmy6-C           **C *G****A*** **AAA***C* T*CT*****G
αAmy3-C    C***A**G*C *G****A*** *C**G***G* C*TC**C***
                                                  1220

                                                    81
αAmy7-C    AGCGATCTCT ACCTCGCGGA GATCGATGGC AAGGTGATCA
αAmy10-C   ********** *******C** ******C**A *****C****
αAmy8-C    G*G**CA*** **G****CAT ******C*** **********
αAmy6-C    G*A**CG*** *TG****CAT ********AT *****C**A*
αAmy3-C    GC***CGCA* **G****C*T CG****C*AG *****C**GG
                                                  1260

                                                   121
αAmy7-C    CAAAGATTGG ACCAAGATAC GACGTCGAAC ACCTCATCCC
αAmy10-C   *G***G*C** ********** ********G* **********
αAmy8-C    *C***C*C** G**G**G*** ****C**GCG GGA*******
αAmy6-C    ********** GA**C*G**T *****G*GCA **T*A*****
αAmy3-C    TG*****C** GA*G**G*** *****G*GCA **GCGG*G**
                                                  1300

                                                   161
αAmy7-C    CGAAGGCTTC CAGGTCGTCG CGCACGGTGA TGGCTACGCA
αAmy10-C   ********** ********** ********** C*********
αAmy8-C    *TCC*A**** **T*****T* *******CA* C*A****TGC
αAmy6-C    GTC**A**** **T*****T* *T*****CA* CAAT***TGC
αAmy3-C    GTCG*AT*** **TCAGACG* T******CA* G*A****AGC
                                                1340

                                                   199
αAmy7-C    ATCTGGGAGA A--AATCTGA GCGCACGATG ACGAGACTCT
αAmy10-C   G********* *--------- AAT*TGAGC* GT*GAGAGGC
αAmy8-C    G********* *GG**GGCCT CA*GGTTCCT G*CG*TAGAA
αAmy6-C    **T*****A* **AGCGG*CT CAGAGTTCCT G*AG*G*GGC
αAmy3-C    G********* ***GG**CCT C***GTCCC* G**G*GCGGC
                                           Pst I  1380

                                                   230
αAmy7-C    CAGTTTAGC- -------AGA TTTAACCTGC GATTTTT-AC
αAmy10-C   ACAA*****A GATTTT-**C --*TTA*CTG C*A****-TT
αAmy8-C    AGCAC**TT* *C***A---- GC**TAGC*A TCGAG**GCA
αAmy6-C    ACCAC**TT* *GCGAAG*A* A**TTT*A*G AC*A***-GG
αAmy3-C    ACC*A****G *GC*CA-**C CC***A***A ACGGGA*-*G
                                                1418
```

FIG. 21A

```
                                                     270
αAmy7-C    CCTGACCGGT ATACGTATAT ACGTGCCGGC AACGAGCTGT
αAmy10-C   **ACC*TC*A CGTATA*C** *TACATGT*A TGGC*A*GAG
αAmy8-C    TGGTG*TTTG CA**CCTAGA TAA*ATATAT *CGT*CG**G
αAmy6-C    TGCCTGGAA* *AGAT*TG*A TTA*AT*CTA **TA*C*A*A
αAmy3-C    T*ATG*TCAA *CCAG*T*C* **AC*G*AAG **TTTA***A
                                                  1458

                                                     296
αAmy7-C    ATCCGATCCG AAT------- -------TAC GGATGCAATT
αAmy10-C   T*GTATG*T* T**CTG---A TCTGAAC**T *T*C**G***
αAmy8-C    C**TAGCTAT G*ATCA---T G*AATTT*G* T*CGAG*TG*
αAmy6-C    T*AT***TGT *TGAGATTTC *TAATCTG*G CA*A**GT*G
αAmy3-C    T**TT**A*T TT*GA---G **AATTAA*T TATG*TTT**
                                                  1495

                                                     336
αAmy7-C    GTCCACGAAG TACTTCCTCC GTAAATAAAG TGAGGATCAG
αAmy10-C   ******A*** ****A***** ********** *******AT*
αAmy8-C    **A*GA*CGA GCT*CGA*-* *ATGTACGCT *CGTT**A*C
αAmy6-C    AG*ATT*CTC CGA*ATT**T A*GT**TCTA CCT*CC*GG*
αAmy3-C    A*AT*T*T*A *TT*GTA*** *ATTG**GC* *TC*A**A**
                 Sca I      Pvu I                 1535

                                                     376
αAmy7-C    GGACATACAT TTGTATGGTT TTACGAATAA TGCTATGCAA
αAmy10-C   *A****G*G* ***C*-T*CA *GGTTTT
αAmy8-C    TAG*G*T*T* CG*A*-ATAA G**A*CGG** *--GTAC*CT
αAmy6-C    *ATATG*T** *****-TCC* C**GA*G*** A*A*GATTTT
αAmy3-C    TAGGCAGGC* C*C**-*CC* C**G*TTA*T ***GGG***T
                                              Nde I 1574

                                                     416
αAmy7-C    TAAAATTTGC ACTGCTTAAT GCTTATGCAT TTTTGCTTGG
αAmy8-C    GTT***CCTG CAGAAA*GTA *GA*GAATGG AA**AAC*A*
αAmy6-C    A*CTC
αAmy3-C    ATGT*GC*TG C*A*T*A*T* *TG*T**T** CACGCAG*TT
                                                  1614

αAmy7-C    TTC
αAmy8-C    C*ACTGTTCG TTTCGATCCT C
αAmy3-C    G*AACCG*T* G*G*A**ATA TAATGTCAGG TTCAGGATGC
                                                  1654
```

FIG. 21B

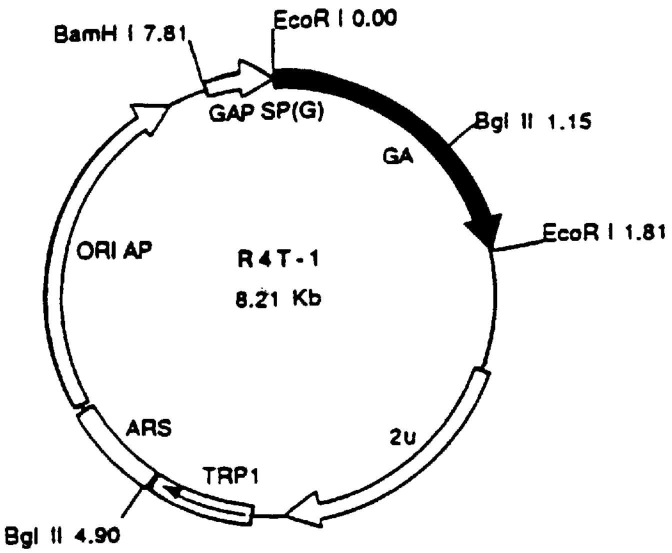
FIG. 30A
FIG. 30B
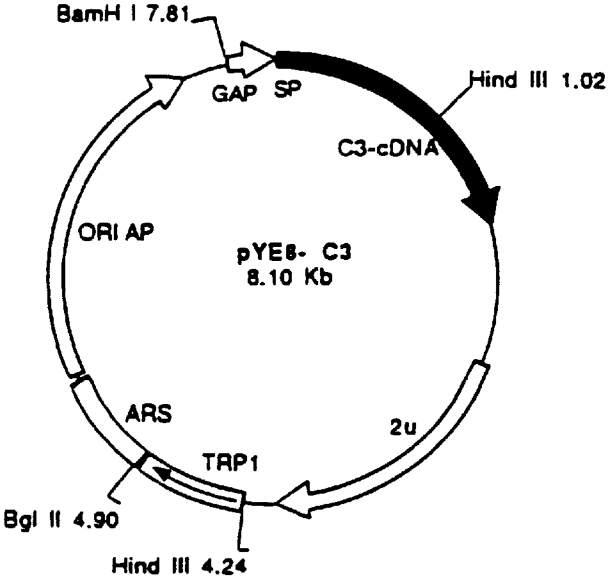

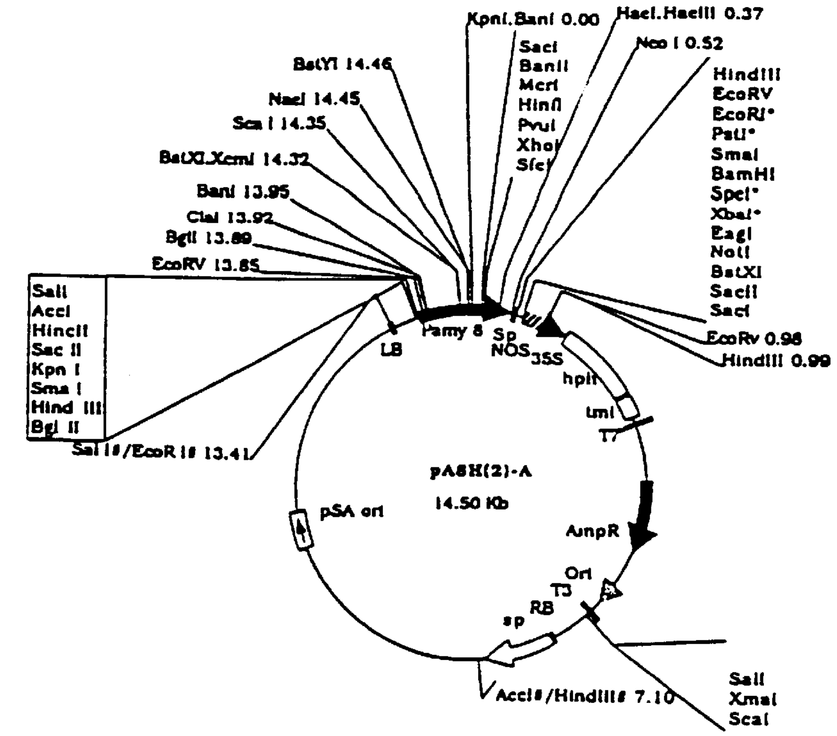
FIG. 32A
FIG. 32B
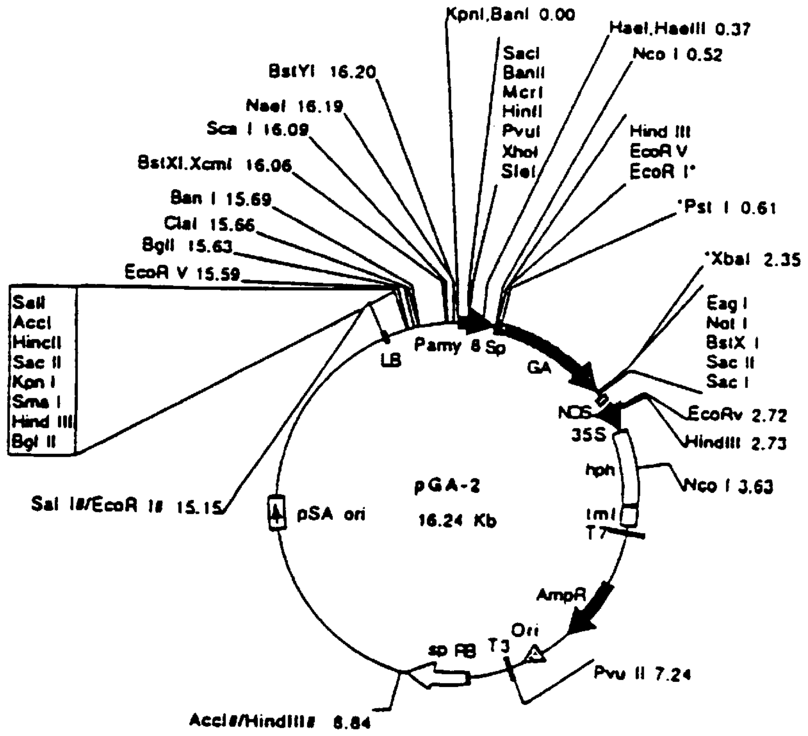

SEQUENCE LISTING

```
(1) GENERAL INFORMATION:

   (iii) NUMBER OF SEQUENCES: 15


(2) INFORMATION FOR SEQ ID NO: 1:

     (i) SEQUENCE CHARACTERISTICS:
          (A) LENGTH: 2086 base pairs
          (B) TYPE: nucleic acid
          (C) STRANDEDNESS: double
          (D) TOPOLOGY: linear

    (ii) MOLECULE TYPE: DNA (genomic)

    (vi) ORIGINAL SOURCE:
          (A) ORGANISM: Rice (Oryzae sativa)
          (B) STRAIN: CV. M202

   (vii) IMMEDIATE SOURCE:
          (A) LIBRARY: (EMBL) genomic
          (B) CLONE: alpha-Amy6-C
```

(ix) FEATURE:
    (A) NAME/KEY: CDS
    (B) LOCATION: join(481..495, 572..1510, 1610..1891)

(ix) FEATURE:
    (A) NAME/KEY: mat_peptide
    (B) LOCATION: join(481..495, 572..1510, 1610..1891)

(x) PUBLICATION INFORMATION:
    (A) AUTHORS: Yu et al., Su-May
    (B) TITLE: Regulation of alpha-amylase-encoding gene
        expression in germinating seeds and cultured cells of rice
    (C) JOURNAL: Gene
    (D) VOLUME: in press (xi) SEQUENCE DESCRIPTION: SEQ ID NO: 1:

```
AAGCTTCTGA AGCTGATGCG ATCAAACCTC AAAAGACCAT GGGCAGCAGC ACGGAAGTTA      60

CAAACCGAAG CCGCGCGGCG CGCATACGCA TCAGAAAGGC GCGCAATAAC GGACCACCCA     120

TACGGCGGCC GCGCTCTGTT CGCGGCGTCC CTGCGCCTGC ATCGCACGCC ATCCAAGGCT     180

GCATAGCACG ACGCATACAT ATCTCACGCG CCCTTTTTAT CTGCTTATAA ATGAGATAGC     240

CCACATAGCA GCGCTGCCGT TTCTCCTCTT CTCTCGTTGG GGGCAACCGA ACTTATCCAA     300

CAACGATCCA TCCATTGGCC AAGTGGCTGC CGTGCTGCAC CTATAAATTC ACATGCACCG     360

GCATGCCACT CCACACAAGT GAGCTACTCG AAAGAAGCAG CA ATG GCA AAG CGC       414
                                               Met Ala Lys Arg
                                               -26 -25

ATA GCC TCA ATG AGC AGC CTC CTC CTT ATC GCC TTG CTC TGT CTG AGC      462
Ile Ala Ser Met Ser Ser Leu Leu Leu Ile Ala Leu Leu Cys Leu Ser
        -20              -15              -10

TCT CAC TTG GCC CAA GCC CAG GTC CTC TTC CAG GTAAGCATCC TGTAGTACAA     515
Ser His Leu Ala Gln Ala Gln Val Leu Phe Gln
 -5               1               5

TGTCACATTA CATAAAAAAA AATGACTTGC GTTTGACATG ACTGTTCTTG GTGTAG         571

GGG TTC AAC TGG GAG TCG TGG AAG AAG CAG GGC GGG TGG TAC AAC TTC      619
Gly Phe Asn Trp Glu Ser Trp Lys Lys Gln Gly Gly Trp Tyr Asn Phe
             10              15              20

CTC CAT GGC CAC GTC GAC GAC ATC GCC GCG ACC GGT GTC ACG CAC GTC      667
Leu His Gly His Val Asp Asp Ile Ala Ala Thr Gly Val Thr His Val
         25              30              35

TGG CTC CCA CCG CCG TCG CAC TCC GTC GCC CCG CAG GGA TAC ATG CCG      715
Trp Leu Pro Pro Pro Ser His Ser Val Ala Pro Gln Gly Tyr Met Pro
         40              45              50

GGC CGG CTC TAC GAC CTG GAC GCT TCC AAG TAC GGC ACG GGG GCA GAG      763
Gly Arg Leu Tyr Asp Leu Asp Ala Ser Lys Tyr Gly Thr Gly Ala Glu
         55              60              65

CTC AGG TCG CTG ATC GCC GCC TTC CAC AGC AAA GGC ATC AAG TGC GTC      811
Leu Arg Ser Leu Ile Ala Ala Phe His Ser Lys Gly Ile Lys Cys Val
 70              75              80                          85

GCC GAC ATC GTC ATC AAC CAC CGG TGC GCG GAT TAC AAG GAT AGC CGT      859
Ala Asp Ile Val Ile Asn His Arg Cys Ala Asp Tyr Lys Asp Ser Arg
                 90              95              100

GGC ATC TAC TGC ATT TTC GAG GGT GGC ACG CCG GAC AGC CGC CTC GAC      907
Gly Ile Tyr Cys Ile Phe Glu Gly Gly Thr Pro Asp Ser Arg Leu Asp
             105             110             115

TGG GGC CCC GAC ATG ATC TGC AGC GAC GAC ACG CAG TAC TCC AAC GGC      955
Trp Gly Pro Asp Met Ile Cys Ser Asp Asp Thr Gln Tyr Ser Asn Gly
         120             125             130

CGC GGT CAC CGC GAC ACC GGC GCA GAC TTC GGC GCG GCG CCC GAC ATC     1003
Arg Gly His Arg Asp Thr Gly Ala Asp Phe Gly Ala Ala Pro Asp Ile
         135             140             145
```

-continued

```
GAC CAC CTC AAC ACG CGT GTG CAG ACA GAG CTG TCC GAC TGG CTC AAT     1051
Asp His Leu Asn Thr Arg Val Gln Thr Glu Leu Ser Asp Trp Leu Asn
150                 155                 160                 165

TGG CTC AAG TCC GAC GTC GGC TTC GAC GGC TGG CGC CTC GAC TTC GCC     1099
Trp Leu Lys Ser Asp Val Gly Phe Asp Gly Trp Arg Leu Asp Phe Ala
                170                 175                 180

AAG GGA TAC TCG GCG GCC GTC GCC AAG ACG TAC GTC GAC AAC ACC GAC     1147
Lys Gly Tyr Ser Ala Ala Val Ala Lys Thr Tyr Val Asp Asn Thr Asp
            185                 190                 195

CCG TCC TTC GTC GTC GCC GAG ATA TGG AGC AAC ATG CGT TAC GAC GGC     1195
Pro Ser Phe Val Val Ala Glu Ile Trp Ser Asn Met Arg Tyr Asp Gly
        200                 205                 210

AAC GGT GAG CCG TCG TGG AAC CAG GAC GGT GAC CGG CAG GAG CTG GTG     1243
Asn Gly Glu Pro Ser Trp Asn Gln Asp Gly Asp Arg Gln Glu Leu Val
    215                 220                 225

AAC TGG GCG CAG GCC GTC GGT GGC CCT GCG TCA GCG TTC GAC TTC ACG     1291
Asn Trp Ala Gln Ala Val Gly Gly Pro Ala Ser Ala Phe Asp Phe Thr
230                 235                 240                 245

ACC AAG GGC GAG CTG CAG GCG GCG GTG CAA GGT GAG CTG TGG CGG ATG     1339
Thr Lys Gly Glu Leu Gln Ala Ala Val Gln Gly Glu Leu Trp Arg Met
                250                 255                 260

AAG GAC GGC AAC GGC AAG GCG CCG GGG ATG ATT GGC TGG CTG CCA GAG     1387
Lys Asp Gly Asn Gly Lys Ala Pro Gly Met Ile Gly Trp Leu Pro Glu
            265                 270                 275

AAG GCC GTC ACC TTC ATC GAC AAC CAT GAC ACT GGC TCC ACA CAG AAC     1435
Lys Ala Val Thr Phe Ile Asp Asn His Asp Thr Gly Ser Thr Gln Asn
        280                 285                 290

TCA TGG CCG TTC CCC TCC GAC AAG GTC ATG CAG GGC TAC GCC TAC ATC     1483
Ser Trp Pro Phe Pro Ser Asp Lys Val Met Gln Gly Tyr Ala Tyr Ile
    295                 300                 305

CTC ACA CAC CCT GGA GTA CCC TGC ATT GTGAGTCCTC AGCTGCATGA           1530
Leu Thr His Pro Gly Val Pro Cys Ile
310                 315

ATACGAATGC CATAAAGAAA AATCTAATTT TCTCAACCAG TTTCTCCGAC TAAATTCTGT   1590

TTATTGACTA TGTGTGCAG TTC TAC GAC CAT GTA TTT GAC TGG AAC CTG AAG    1642
                     Phe Tyr Asp His Val Phe Asp Trp Asn Leu Lys
                         320                 325

CAG GAG ATC AGC ACA TTA GCT GCA GTG AGA TCA AGA AAT GAG ATT CAT     1690
Gln Glu Ile Ser Thr Leu Ala Ala Val Arg Ser Arg Asn Glu Ile His
330                 335                 340                 345

CCC GGG AGC AAG CTG AAA ATC CTT GCT GCT GAG GGA GAC GTC TAT GTC     1738
Pro Gly Ser Lys Leu Lys Ile Leu Ala Ala Glu Gly Asp Val Tyr Val
                350                 355                 360

GCC ATG ATC GAT GAT AAG GTC ATA ACA AAG ATT GGG ACA CGG TAT GAC     1786
Ala Met Ile Asp Asp Lys Val Ile Thr Lys Ile Gly Thr Arg Tyr Asp
            365                 370                 375

GTG GGC AAC TTA ATC CCG TCA GAC TTC CAT GTC GTT GCT CAC GGC AAC     1834
Val Gly Asn Leu Ile Pro Ser Asp Phe His Val Val Ala His Gly Asn
        380                 385                 390

AAT TAC TGC ATT TGG GAA AAG AGC GGT CTC AGA GTT CCT GCA GGG CGG     1882
Asn Tyr Cys Ile Trp Glu Lys Ser Gly Leu Arg Val Pro Ala Gly Arg
    395                 400                 405

CAC CAC TAT TAGGCGAAGA AAATTTTTCA GGACTATTTG GTGCCTGGAA             1931
His His Tyr
410

TAAGATTTGA ATTATATCCT AAATAACCAG ATTATGATTG TATGAGATTT CTTAATCTGA   1991

GCAAAGCGTT GAGCATTGCT CCGATATTTC TATGTATTCT ACCTGCCTGG GGATATGATA   2051
```

-continued

```
TTTGTATCCT CTAGAAGTAA AGATGATTTT AACTC                                   2086


(2) INFORMATION FOR SEQ ID NO: 2:

     (i) SEQUENCE CHARACTERISTICS:
          (A) LENGTH: 438 amino acids
          (B) TYPE: amino acid
          (D) TOPOLOGY: linear

    (ii) MOLECULE TYPE: protein

    (xi) SEQUENCE DESCRIPTION: SEQ ID NO: 2:

Met Ala Lys Arg Ile Ala Ser Met Ser Ser Leu Leu Leu Ile Ala Leu
-26 -25                 -20                 -15

Leu Cys Leu Ser Ser His Leu Ala Gln Ala Gln Val Leu Phe Gln Gly
-10                  -5                   1               5

Phe Asn Trp Glu Ser Trp Lys Lys Gln Gly Gly Trp Tyr Asn Phe Leu
            10                  15                  20

His Gly His Val Asp Asp Ile Ala Ala Thr Gly Val Thr His Val Trp
        25                  30                  35

Leu Pro Pro Pro Ser His Ser Val Ala Pro Gln Gly Tyr Met Pro Gly
    40                  45                  50

Arg Leu Tyr Asp Leu Asp Ala Ser Lys Tyr Gly Thr Gly Ala Glu Leu
 55                  60                  65                  70

Arg Ser Leu Ile Ala Ala Phe His Ser Lys Gly Ile Lys Cys Val Ala
                 75                  80                  85

Asp Ile Val Ile Asn His Arg Cys Ala Asp Tyr Lys Asp Ser Arg Gly
            90                  95                 100

Ile Tyr Cys Ile Phe Glu Gly Gly Thr Pro Asp Ser Arg Leu Asp Trp
        105                 110                 115

Gly Pro Asp Met Ile Cys Ser Asp Asp Thr Gln Tyr Ser Asn Gly Arg
    120                 125                 130

Gly His Arg Asp Thr Gly Ala Asp Phe Gly Ala Ala Pro Asp Ile Asp
135                 140                 145                 150

His Leu Asn Thr Arg Val Gln Thr Glu Leu Ser Asp Trp Leu Asn Trp
                155                 160                 165

Leu Lys Ser Asp Val Gly Phe Asp Gly Trp Arg Leu Asp Phe Ala Lys
            170                 175                 180

Gly Tyr Ser Ala Ala Val Ala Lys Thr Tyr Val Asp Asn Thr Asp Pro
        185                 190                 195

Ser Phe Val Val Ala Glu Ile Trp Ser Asn Met Arg Tyr Asp Gly Asn
    200                 205                 210

Gly Glu Pro Ser Trp Asn Gln Asp Gly Asp Arg Gln Glu Leu Val Asn
215                 220                 225                 230

Trp Ala Gln Ala Val Gly Gly Pro Ala Ser Ala Phe Asp Phe Thr Thr
                235                 240                 245

Lys Gly Glu Leu Gln Ala Ala Val Gln Gly Glu Leu Trp Arg Met Lys
            250                 255                 260

Asp Gly Asn Gly Lys Ala Pro Gly Met Ile Gly Trp Leu Pro Glu Lys
        265                 270                 275

Ala Val Thr Phe Ile Asp Asn His Asp Thr Gly Ser Thr Gln Asn Ser
    280                 285                 290

Trp Pro Phe Pro Ser Asp Lys Val Met Gln Gly Tyr Ala Tyr Ile Leu
295                 300                 305                 310

Thr His Pro Gly Val Pro Cys Ile Phe Tyr Asp His Val Phe Asp Trp
                315                 320                 325
```

-continued

Asn Leu Lys Gln Glu Ile Ser Thr Leu Ala Ala Val Arg Ser Arg Asn
330 335 340

Glu Ile His Pro Gly Ser Lys Leu Lys Ile Leu Ala Ala Glu Gly Asp
345 350 355

Val Tyr Val Ala Met Ile Asp Asp Lys Val Ile Thr Lys Ile Gly Thr
360 365 370

Arg Tyr Asp Val Gly Asn Leu Ile Pro Ser Asp Phe His Val Val Ala
375 380 385 390

His Gly Asn Asn Tyr Cys Ile Trp Glu Lys Ser Gly Leu Arg Val Pro
395 400 405

Ala Gly Arg His His Tyr
410

(2) INFORMATION FOR SEQ ID NO: 3:

(i) SEQUENCE CHARACTERISTICS:
(A) LENGTH: 4276 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Rice (Oryzae sativa)
(B) STRAIN: CV. M202

(vii) IMMEDIATE SOURCE:
(A) LIBRARY: (EMBL) genomic
(B) CLONE: alpha-Amy7-C (ix) FEATURE:
(A) NAME/KEY: CDS
(B) LOCATION: join(2459..2473, 2582..2713, 2807..3619, 3704 ..3952)

(ix) FEATURE:
(A) NAME/KEY: mat_peptide
(B) LOCATION: join(2459..2473, 2582..2713, 2807..3619, 3704 ..3952)

(x) PUBLICATION INFORMATION:
(A) AUTHORS: Yu et al., Su-May
(B) TITLE: Regulation of alpha-amylase-encoding gene expression in germinating seeds and cultured cells of rice
(C) JOURNAL: Gene
(D) VOLUME: in press (xi) SEQUENCE DESCRIPTION: SEQ ID NO: 3:

GCATGCGAGA GGCACGGGGT TCGATTCCCC GCGTCTCCAT CGGCACTGTT TTTTAACATC 60

AAACGCTGTT CGATCCACTA TCTGTTAATT TCGCAAACAC AACTAAATCT TTTTTTTTTT 120

TTGCCGGTGC GTGCAGTGTG ACGTCCAAGG CATGGCGCAT TGGCGCCTCC CCTCTTTCCC 180

TTGATCTTTT CATCAGTTCG TTCTTCTTGC AGAAAAGCTG TTCTGTTAAG TCGGTTCCGA 240

TCTGCTCTTG GGCTCTTGCC AGAAACAACC TGTGTACGCC AGACTTATCA AGCCAACCAT 300

CCTGATGAGC CTCTGCTTAT ACAAGCCTTT GACTCCAAAA AGGACGAGGC GGCTTGCAGC 360

CGCACGGAAA TAAGCCGACC GATCCTTTAT TGCTCTATCT TTTTCCCTTG GAATAAAAAA 420

CAGCCCAATT AAAATCTGGG ATGAAACTAT GGCTAGCTGT TCGCGGTGTC AGTTCTCGGG 480

ACGCTACCGT TGTTTTGTTT GAACCGGAAT GTTCAGGGCG GTTCACACCA TAGACTTGGA 540

GCCAAGTGGT TCCATCCACA AAATTTTCTC ATCTTGAATA TTCTGTTATC TGCCTCGACA 600

GACGCGCCAT ATCCTGTGTT CAGGAATGAA TGTGCTACAG CCAACGTGCT GCATGAAATT 660

-continued

```
TGCTGAAATC GTGCTAAAAT GTGCATGGCA ACAGGAACCT GATGCCCTGG TCCTGTGGAA    720

CTGCCACGGG AAAGTATTTT TTATAGCTAG GTGCAATCGT ATCTAGGTGT ATACATGTCA    780

CCTACATAGC TACTCCCCTT TATCTTAAAA TATAATAATT TTTAACTCTC AGTATTTGTC    840

CTAAAATATA ACAAATTCTC CATCAACATT ATCTTCCCAA CCAATCACAA CCCTTCATCA    900

TTAATTTTTT CCCCCTACCT CCACTACTCA TCTAATCACA ACCCTCCAAC ACTCACTTCT    960

ATCTACTTTC TTAATAACTG TCTTCAACCC TAAAACTTCT TATATTTTAG GACGGAGGGA   1020

GTATCTAAAT ATTTCATAAA AAAAATGTTA AGATAGATAA AGAAGATATA AACCCACTAT   1080

GCAAACATGC ACATCAAAAT TTAATTTACA GTAAAGAAAC AGAAATAACA TATTCTATTT   1140

GTGCTGGAGA TGTACTGTTC ACAATATTGT TTTTTTATTT TTTATTTATC TGATTATATA   1200

TCTGTTTCAG CCTTGCATGG TTGTGTATGT TTGTGTATAG ACTTATGCCA TTGTGATTGA   1260

TGCTACCAAT TATTTTCAGA CTATTTTTTT ATAGAGGAAT TTTATAGTTC TTGAGAAAAT   1320

ACCTTGAAGT ATCTAAATTT TACACTAAAA TTGTTGGTAC CTTGAGGTAC AAAGTACCTA   1380

GAGGTACCAA ATTTTACTAG AAAATTGTGG CACCTTTAGG TACCTTCTCA AAAATAGTAC   1440

AATTATGGGC CGTTTTGGAT TTAGTGCCAA AACGTGCTCT ACAAATATTT TGATAGTTTG   1500

AACAGTGCAT AAGACGGGTT TGGTTTGAAG CCAAATCATT GGCATTGCCA ATGTCCAATT   1560

TGATATTTTC TATATTATGC TAAAAGCTTG GTTCTAAATT GGCCTCCAAC CAAATACAAC   1620

TCTACTCTAC CAAAAAATTT GTAGTGCCAA AACTTGCCTA GGTTTTGTCA CTACCAACAT   1680

TTTGGTAAGT ATTAAACCAA ACAAGCCCTA CATTTTTTTA TGTACATTTA AGTTGTATGT   1740

AAATGATGGG TGCGGTTGCA CCTAGGTGAA AAAAAATACA TATTCGCCAC AACTCGCAAC   1800

ATGTACCAAT TCAGCAGCAA GTGTAAGAGA GAAGATTTCT CTCGTTTTAC ACGCGCACGT   1860

TCAATTCCTG AACTACTAAA CGGTATGATT TTTTGCAAAA ATTTTCTATA GGAAAGTTAC   1920

TTAAAAATTA TATTAATCTA TTTTTAAAAT TTAAAATAGT TAATACTCAA TTAATTATAC   1980

GTTAATGGCT CAGCTCGTTT TGCGTACATT CTCAATCGAT TCTTTTCCTC TGCTCTCAAA   2040

TGCTCTGTGT GCGATCAGGT ATTCATGTTC AGCTCGCACA AGCACAAGCA AGACAGATGG   2100

AATTCCTACT GACCTGCGCC TTTTGCATCG CTCCAACTCT CAAAGTCTCA AGGCCATTAA   2160

ATTGCCTATG GGCTCACCAG CCAATAACAA ACTCCGGCTG TTATCCATCC AATCCAGTGT   2220

CCCAAAGCAA CATTCAAGCC CAGCCAGGCC TCCAAAAGTT GCAAGTTGAG CATGGCAAAA   2280

TCCCCGGCAA TTCTCGACTA TAAATACCTG ACCAGACACA CCCAGGAGCT TCATCAATCA   2340

TCCATCTCCG AAGTGTGTCT GCAGCATGCA GGTGCTGAAC ACC ATG GTG AAC AAA     2395
                                                Met Val Asn Lys
                                                -25

CAC TTC TTG TCC CTT TCG GTC CTC ATC GTC CTC CTT GGC CTC TCC TCC     2443
His Phe Leu Ser Leu Ser Val Leu Ile Val Leu Leu Gly Leu Ser Ser
    -20                 -15                 -10

AAC TTG ACA GCC GGG CAA GTC CTG TTT CAG GTAAGAGATC GCCATGAGTT       2493
Asn Leu Thr Ala Gly Gln Val Leu Phe Gln
 -5                  1               5

GGGTTTCAGG CTTCAGTGAA CTGATCCGGT TTTGTACTGA GCCTAAGAGA ATGATGCAGT   2553

GATGCTCTTG TGTTTGATGA TGATGCAG GGA TTC AAC TGG GAC TCG TGG AAG      2605
                               Gly Phe Asn Trp Asp Ser Trp Lys
                                                10

GAG AAT GGC GGG TGG TAC AAC TTC CTG ATG GGC AAG GTG GAC GAC ATC     2653
Glu Asn Gly Gly Trp Tyr Asn Phe Leu Met Gly Lys Val Asp Asp Ile
     15                  20                  25

GCC GCA GCC GGC ATC ACC CAC GTC TGG CTC CCT CCG CCG TCT CAC TCT     2701
```

-continued

```
Ala Ala Ala Gly Ile Thr His Val Trp Leu Pro Pro Pro Ser His Ser
 30                 35                  40                  45

GTC GGC GAG CAA GGTGCGGTGC TCTGCTCTCT CGATCCCCTC GTCGTCGCAC        2753
Val Gly Glu Gln

CATTGCCGGC AAAATACATG CACAGGTCGT TGAATTGCTT GAATGCTTCT GCA GGC     2809
                                                           Gly
                                                            50

TAC ATG CCT GGG CGG CTG TAC GAT CTG GAC GCG TCT AAG TAC GGC AAC    2857
Tyr Met Pro Gly Arg Leu Tyr Asp Leu Asp Ala Ser Lys Tyr Gly Asn
                 55                  60                  65

GAG GCG CAG CTC AAG TCG CTG ATC GAG GCG TTC CAT GGC AAG GGC GTC    2905
Glu Ala Gln Leu Lys Ser Leu Ile Glu Ala Phe His Gly Lys Gly Val
             70                  75                  80

CAG GTC ATC GCC GAC ATC GTC ATC AAC CAC CGC ACG GCG GAG CAC AAG    2953
Gln Val Ile Ala Asp Ile Val Ile Asn His Arg Thr Ala Glu His Lys
         85                  90                  95

GAC GGC CGC GGC ATC TAC TGC CTC TTC GAG GGC GGG ACG CCC GAC TCC    3001
Asp Gly Arg Gly Ile Tyr Cys Leu Phe Glu Gly Gly Thr Pro Asp Ser
    100                 105                 110

CGC CTC GAC TGG GGC CCG CAC ATG ATC TGC CGC GAC GAC CCC TAC GGC    3049
Arg Leu Asp Trp Gly Pro His Met Ile Cys Arg Asp Asp Pro Tyr Gly
115                 120                 125                 130

GAT GGC ACC GGC AAC CCG GAC ACC GGC GCC GAC TTC GCC GCC GCG CCG    3097
Asp Gly Thr Gly Asn Pro Asp Thr Gly Ala Asp Phe Ala Ala Ala Pro
                135                 140                 145

GAC ATC GAC CAC CTC AAC AAG CGC GTC CAG CGG GAC CTC ATT GGC TGG    3145
Asp Ile Asp His Leu Asn Lys Arg Val Gln Arg Asp Leu Ile Gly Trp
            150                 155                 160

CTC GAC TGG CTC AAG ATG GAC ATC GGC TTC GAC GCG TGG CGC CTC GAC    3193
Leu Asp Trp Leu Lys Met Asp Ile Gly Phe Asp Ala Trp Arg Leu Asp
        165                 170                 175

TTC GCC AAG GGC TAC TCC GCC GAC ATG GCA AAG ATC TAC ATC GAC GCC    3241
Phe Ala Lys Gly Tyr Ser Ala Asp Met Ala Lys Ile Tyr Ile Asp Ala
    180                 185                 190

ACC GAG CCG AGC TTC GCC GTG GCC GAG ATA TGG ACG TCC ATG GCG AAC    3289
Thr Glu Pro Ser Phe Ala Val Ala Glu Ile Trp Thr Ser Met Ala Asn
195                 200                 205                 210

GGC GGG GAC GGC AAG CCG AAC TAC GAC CAG AAC GCG CAC CGG CAG GAG    3337
Gly Gly Asp Gly Lys Pro Asn Tyr Asp Gln Asn Ala His Arg Gln Glu
                215                 220                 225

CTG GTC AAC TGG GTC GAT CGT GTC GGC GGC GCC AAC AGC AAC GGC ACG    3385
Leu Val Asn Trp Val Asp Arg Val Gly Gly Ala Asn Ser Asn Gly Thr
            230                 235                 240

GCG TTC GAC TTC ACC ACC AAG GGC ATC CTC AAC GTC GCC GTG GAG GGC    3433
Ala Phe Asp Phe Thr Thr Lys Gly Ile Leu Asn Val Ala Val Glu Gly
        245                 250                 255

GAG CTG TGG CGC CTC CGC GGC GAG GAC GGC AAG GCG CCC GGC ATG ATC    3481
Glu Leu Trp Arg Leu Arg Gly Glu Asp Gly Lys Ala Pro Gly Met Ile
    260                 265                 270

GGG TGG TGG CCG GCC AAG GCG ACG ACC TTC GTC GAC AAC CAC GAC ACC    3529
Gly Trp Trp Pro Ala Lys Ala Thr Thr Phe Val Asp Asn His Asp Thr
275                 280                 285                 290

GGC TCG ACG CAG CAC CTG TGG CCG TTC CCC TCC GAC AAG GTC ATG CAG    3577
Gly Ser Thr Gln His Leu Trp Pro Phe Pro Ser Asp Lys Val Met Gln
                295                 300                 305

GGC TAC GCA TAC ATC CTC ACC CAC CCC GGC AAC CCA TGC ATC            3619
Gly Tyr Ala Tyr Ile Leu Thr His Pro Gly Asn Pro Cys Ile
            310                 315                 320

GTGAGTAGCC AACTCGATCA GAAATTCTGA ATCATCCTGC AAACTGATCG ATGAACTGAT  3679
```

-continued

```
GATAAATTCT GTAAAATTGT TCAG TTC TAC GAC CAT TTC TTC GAT TGG GGT      3730
                           Phe Tyr Asp His Phe Phe Asp Trp Gly
                                           325

CTC AAG GAG GAG ATC GAG CGC CTG GTG TCA ATC AGA AAC CGG CAG GGG     3778
Leu Lys Glu Glu Ile Glu Arg Leu Val Ser Ile Arg Asn Arg Gln Gly
330                 335                 340                 345

ATC CAC CCG GCG AGC GAG CTG CGC ATC ATG GAA GCT GAC AGC GAT CTC     3826
Ile His Pro Ala Ser Glu Leu Arg Ile Met Glu Ala Asp Ser Asp Leu
                350                 355                 360

TAC CTC GCG GAG ATC GAT GGC AAG GTG ATC ACA AAG ATT GGA CCA AGA     3874
Tyr Leu Ala Glu Ile Asp Gly Lys Val Ile Thr Lys Ile Gly Pro Arg
            365                 370                 375

TAC GAC GTC GAA CAC CTC ATC CCC GAA GGC TTC CAG GTC GTC GCG CAC     3922
Tyr Asp Val Glu His Leu Ile Pro Glu Gly Phe Gln Val Val Ala His
        380                 385                 390

GGT GAT GGC TAC GCA ATC TGG GAG AAA ATC TGAGCGCACG ATGACGAGAC       3972
Gly Asp Gly Tyr Ala Ile Trp Glu Lys Ile
    395                 400

TCTCAGTTTA GCAGATTTAA CCTGCGATTT TTACCCTGAC CGGTATACGT ATATACGTGC   4032

CGGCAACGAG CTGTATCCGA TCCGAATTAC GGATGCAATT GTCCACGAAG TACTTCCTCC   4092

GTAAATAAAG TAGGATCAGG GACATACATT TGTATGGTTT TACGAATAAT GCTATGCAAT   4152

AAAATTTGCA CTGCTTAATG CTTATGCATT TTTGCTTGGT TCGATTCTAC TGGTGAATTA   4212

TTGTTACTGT TCTTTTTACT TCTCGAGTGG CAGTATTGTT CTTCTACGAA AATTTGATGC   4272

GTAG                                                                4276
```

(2) INFORMATION FOR SEQ ID NO: 4:

(i) SEQUENCE CHARACTERISTICS:
(A) LENGTH: 428 amino acids
(B) TYPE: amino acid
(D) TOPOLOGY: linear (ii) MOLECULE TYPE: protein (xi) SEQUENCE DESCRIPTION: SEQ ID NO: 4:

```
Met Val Asn Lys His Phe Leu Ser Leu Ser Val Leu Ile Val Leu Leu
-25                 -20                 -15                 -10

Gly Leu Ser Ser Asn Leu Thr Ala Gly Gln Val Leu Phe Gln Gly Phe
                 -5                   1               5

Asn Trp Asp Ser Trp Lys Glu Asn Gly Gly Trp Tyr Asn Phe Leu Met
        10                  15                  20

Gly Lys Val Asp Asp Ile Ala Ala Ala Gly Ile Thr His Val Trp Leu
     25                  30                  35

Pro Pro Pro Ser His Ser Val Gly Glu Gln Gly Tyr Met Pro Gly Arg
 40                  45                  50                  55

Leu Tyr Asp Leu Asp Ala Ser Lys Tyr Gly Asn Glu Ala Gln Leu Lys
                 60                  65                  70

Ser Leu Ile Glu Ala Phe His Gly Lys Gly Val Gln Val Ile Ala Asp
             75                  80                  85

Ile Val Ile Asn His Arg Thr Ala Glu His Lys Asp Gly Arg Gly Ile
        90                  95                 100

Tyr Cys Leu Phe Glu Gly Gly Thr Pro Asp Ser Arg Leu Asp Trp Gly
    105                 110                 115

Pro His Met Ile Cys Arg Asp Asp Pro Tyr Gly Asp Gly Thr Gly Asn
120                 125                 130                 135
```

-continued

```
Pro Asp Thr Gly Ala Asp Phe Ala Ala Ala Pro Asp Ile Asp His Leu
                140                 145                 150

Asn Lys Arg Val Gln Arg Asp Leu Ile Gly Trp Leu Asp Trp Leu Lys
            155                 160                 165

Met Asp Ile Gly Phe Asp Ala Trp Arg Leu Asp Phe Ala Lys Gly Tyr
        170                 175                 180

Ser Ala Asp Met Ala Lys Ile Tyr Ile Asp Ala Thr Glu Pro Ser Phe
    185                 190                 195

Ala Val Ala Glu Ile Trp Thr Ser Met Ala Asn Gly Gly Asp Gly Lys
200                 205                 210                 215

Pro Asn Tyr Asp Gln Asn Ala His Arg Gln Glu Leu Val Asn Trp Val
                220                 225                 230

Asp Arg Val Gly Gly Ala Asn Ser Asn Gly Thr Ala Phe Asp Phe Thr
            235                 240                 245

Thr Lys Gly Ile Leu Asn Val Ala Val Glu Gly Glu Leu Trp Arg Leu
        250                 255                 260

Arg Gly Glu Asp Gly Lys Ala Pro Gly Met Ile Gly Trp Trp Pro Ala
    265                 270                 275

Lys Ala Thr Thr Phe Val Asp Asn His Asp Thr Gly Ser Thr Gln His
280                 285                 290                 295

Leu Trp Pro Phe Pro Ser Asp Lys Val Met Gln Gly Tyr Ala Tyr Ile
                300                 305                 310

Leu Thr His Pro Gly Asn Pro Cys Ile Phe Tyr Asp His Phe Phe Asp
            315                 320                 325

Trp Gly Leu Lys Glu Glu Ile Glu Arg Leu Val Ser Ile Arg Asn Arg
        330                 335                 340

Gln Gly Ile His Pro Ala Ser Glu Leu Arg Ile Met Glu Ala Asp Ser
    345                 350                 355

Asp Leu Tyr Leu Ala Glu Ile Asp Gly Lys Val Ile Thr Lys Ile Gly
360                 365                 370                 375

Pro Arg Tyr Asp Val Glu His Leu Ile Pro Glu Gly Phe Gln Val Val
                380                 385                 390

Ala His Gly Asp Gly Tyr Ala Ile Trp Glu Lys Ile
            395                 400
```

(2) INFORMATION FOR SEQ ID NO: 5:

(i) SEQUENCE CHARACTERISTICS:
(A) LENGTH: 3314 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Rice (Oryzae sativa)
(B) STRAIN: CV. M202

(vii) IMMEDIATE SOURCE:
(A) LIBRARY: (EMBL) genomic
(B) CLONE: alpha-Amy8-C (ix) FEATURE:
(A) NAME/KEY: CDS
(B) LOCATION: join (1152..1241, 1385..2323, 2409..2690)

(ix) FEATURE:
(A) NAME/KEY: mat_peptide
(B) LOCATION: join (1227..1241, 1385..2323, 2409..2690)

(x) PUBLICATION INFORMATION:

-continued

```
         (A) AUTHORS: Yu et al., Su-May
         (B) TITLE: Regulation of alpha-amylase-encoding gene
             expression in germinating seeds and cultured cells of rice
         (C) JOURNAL: Gene
         (D) VOLUME: in press

    (xi) SEQUENCE DESCRIPTION: SEQ ID NO:5:

GATATCCCGC CAGCACAGTG CCGGAAACTT TAATGCCGAT GGGGCTTTTA ATGCCGGTTG     60

AGAGCATATC GATACGGTTA CGAATTGGCG GCACCCACAG ATTCGCCAGC CCCGGCAGCC    120

GCACGGTGTT ATCCAGTTCC TCAATGATTT TGTCCATCGT CATGCCTGGC CGCCACTGCT    180

CCTGCGGCTT AAGCTGGATG GTCGTTTCTA CCATCTCCAG CGGACAGAAT CGGTGGCCGG    240

TTTCCGTTTC CCGGTTTTGC CAAATACCCG CGCCACTTCA GGTACGCTCA TAATTAGCTT    300

GTCGGTTTTT TGCAGCATAC CGCCGCCTCT GCTGCGGAAA TCCCCGGCAG CGTCGATGGC    360

ATATACACAA GTCGCCTTCA TTGATCTGCG GTAAAAATTC CCGCCAACTT TATTGAGCGG    420

CCAGAGAANN GTAGCACCGA AAGCNCCGCC ACCAGCAGCG TGGTTTTNNN CCAGTGCAGT    480

ACTTCAGCAA CACGGATGAT AAACACGAAT CAAAAAGCGA TTGTGCGGGT TACTGCTTTC    540

CGGCGGAATT TTGCCACGGA TCTCCTTTCC AAAGAAAGTT TCCCTGCCGG CGCTTGATCC    600

GTCACACCGA TGACGCGACG CGGTAGAGGC CGGTACCTGT TCGAACAACC AACTGATCTG    660

CGGCTCCTCC GCTTGCGGCT TGCCTCTTAT CAACGTATCG CCGTTTCCGT CATGCGTGAT    720

CGGTGATCGA TCACCGAGAG AGACCGGACG ACGAGTCGAG AGAGCTCGCG CCGCCTCGAT    780

CGGCGCGGCG GTGACTCGAG CAGGGCCTGA AGTAGCTGCA CGGCTCAAGG CGGCACTCCA    840

TCACCGGACA CCGGGGTCCA GACTACTCGT TTCCGTTGGA GAAATAACCA CCTTTATCCA    900

TGTTGCTTAT CCGTGAATTG CAACAGCATT GATTGTTCGC GTTTAATTCG CCTCGGCCAT    960

GTAACCTCCG ACCTGATCCT CTTGGACACT ATAAATAGAG GCCAGTTCAG GCAATGCAAG   1020

AGCAGAGAAG CAGAGTACAG CAGGCAGCTC TTCTTCTCTT TGCGAAGGTT GGCTACTTGG   1080

CCAGCCATTA GGAAACAAGT TAGTTTGGAG AAGAAGCAGA GTTGAGACTG CATTTGCATT   1140

GCTCTGTAGC C ATG GGC AAG CAC CAT GTC ACC CTG TGT TGT GTC GTT TTT   1190
             Met Gly Lys His His Val Thr Leu Cys Cys Val Val Phe
             -25                 -20                 -15

GCT GTG CTC TGC CTG GCG TCC AGC TTA GCA CAA GCC CAA GTT CTC TTC    1238
Ala Val Leu Cys Leu Ala Ser Ser Leu Ala Gln Ala Gln Val Leu Phe
        -10                 -5                   1

CAG GTAGTTTAAT TTACTGACGC CTTGGTGAAA GTTTGTTAAT ACTTGATAAT         1291
Gln
  5

AATAATCTTG CACGGCAATA TAATGTACGC GCCGCAGTCA GGAAGCTTGA TTTGACCATG   1351

GGTTGCGTTT GGGTGTTTTT GCCGTACGTG CAG GGG TTT AAC TGG GAG TCG TGG   1405
                                     Gly Phe Asn Trp Glu Ser Trp
                                                          10

AGG AAG CAA GGC GGG TGG TAC AAC TTT CTG CAC GAG AAG GTG GAG GAG    1453
Arg Lys Gln Gly Gly Trp Tyr Asn Phe Leu His Glu Lys Val Glu Glu
         15                  20                  25

ATC GCC AGC ACG GGC GCC ACC CAC GTC TGG CTC CCG CCG CCG TCG CAC    1501
Ile Ala Ser Thr Gly Ala Thr His Val Trp Leu Pro Pro Pro Ser His
     30                  35                  40

TCT GTC TCG CCG CAG GGT TAC ATG CCG GGG CGG CTC TAC GAC CTG GAC    1549
Ser Val Ser Pro Gln Gly Tyr Met Pro Gly Arg Leu Tyr Asp Leu Asp
 45                  50                  55                  60

GCG TCC AAG TAC GGC ACG GAG GCG GAG CTC AAG TCG CTG ATC GAG GCA    1597
Ala Ser Lys Tyr Gly Thr Glu Ala Glu Leu Lys Ser Leu Ile Glu Ala
                 65                  70                  75
```

-continued

```
TTC CAC GAC AAG AAC GTC GAG TGC CTC GCC GAC ATC GTC ATC AAC CAC      1645
Phe His Asp Lys Asn Val Glu Cys Leu Ala Asp Ile Val Ile Asn His
             80                  85                  90

CGC TGC GCC GAC TAC AAG GAC AGC CGC GGC GTG TAC TGC GTG TTC GAG      1693
Arg Cys Ala Asp Tyr Lys Asp Ser Arg Gly Val Tyr Cys Val Phe Glu
         95                 100                 105

GGC GGC ACG CCC GAC GGC CGC CTC GAC TGG GGC CCC GAC ATG ATC TGC      1741
Gly Gly Thr Pro Asp Gly Arg Leu Asp Trp Gly Pro Asp Met Ile Cys
    110                 115                 120

AGC GAC GAC ACG CAG TAC TCC AAC GGC CGC GGC CAC CGC GAC ACC GGC      1789
Ser Asp Asp Thr Gln Tyr Ser Asn Gly Arg Gly His Arg Asp Thr Gly
125                 130                 135                 140

GCC GGG TTC GGC GCC GCG CCC GAC ATC GAC CAC CTC AAC CCG CGT GTC      1837
Ala Gly Phe Gly Ala Ala Pro Asp Ile Asp His Leu Asn Pro Arg Val
                145                 150                 155

CAG CGG GAG CTC ACC GAC TGG CTC AAC TGG CTC AGG ACC CAC CTC GGC      1885
Gln Arg Glu Leu Thr Asp Trp Leu Asn Trp Leu Arg Thr His Leu Gly
            160                 165                 170

TTC GAC GGA TGG CGC CTC GAC TTC GCG AAG GGC TAC TCC GCG CCG CTG      1933
Phe Asp Gly Trp Arg Leu Asp Phe Ala Lys Gly Tyr Ser Ala Pro Leu
        175                 180                 185

GCG AGG ATC TAC GTC GAC AAC ACC AAC CCG ACG TTC GTC GTC GGC GAG      1981
Ala Arg Ile Tyr Val Asp Asn Thr Asn Pro Thr Phe Val Val Gly Glu
    190                 195                 200

ATC TGG AGC TCG CTC ATC TAC AAC GGC GAC GGC AAG CCG TCG ACC AAC      2029
Ile Trp Ser Ser Leu Ile Tyr Asn Gly Asp Gly Lys Pro Ser Thr Asn
205                 210                 215                 220

CAG GAC GCG GAC AGG CAG GAG CTG GTG AAC TGG GTG GAG GGC GTC GGC      2077
Gln Asp Ala Asp Arg Gln Glu Leu Val Asn Trp Val Glu Gly Val Gly
                225                 230                 235

AAG CCG GCG ACG GCG TTC GAC TTC ACC ACC AAG GGC ATC CTC CAG GCC      2125
Lys Pro Ala Thr Ala Phe Asp Phe Thr Thr Lys Gly Ile Leu Gln Ala
            240                 245                 250

GCC GTG CAG GGC GAG CTG TGG AGG CTC CAC GAC GGC AAC GGC AAG GCG      2173
Ala Val Gln Gly Glu Leu Trp Arg Leu His Asp Gly Asn Gly Lys Ala
        255                 260                 265

CCC GGC CTC ATG GGG TGG ATG CCC GAT CAG GCC GTA ACC TTC GTC GAC      2221
Pro Gly Leu Met Gly Trp Met Pro Asp Gln Ala Val Thr Phe Val Asp
    270                 275                 280

AAC CAC GAC ACC GGC TCG ACC CAG TCG CTC TGG CCG TTC CCT TCC GAC      2269
Asn His Asp Thr Gly Ser Thr Gln Ser Leu Trp Pro Phe Pro Ser Asp
285                 290                 295                 300

AAG GTC ATG CAG GGC TAC GCC TAC ATC CTC ACT CAC CCT GGC ATC CCA      2317
Lys Val Met Gln Gly Tyr Ala Tyr Ile Leu Thr His Pro Gly Ile Pro
                305                 310                 315

TGC ATC GTAAGTATCA CCACCGAAAT CTTTCTCATC AAATTCGTTC ATATTGGTGA      2373
Cys Ile

GCTCATTGCT GGTGCATGTG TACGTGTGTA TGCAG TTC TAC GAC CAT GTG TTC      2426
                                       Phe Tyr Asp His Val Phe
                                           320

GAC TGG AAC CTG CAG CAC GAG ATC GCG ACG CTG GCT GAA ATC CGG TCA      2474
Asp Trp Asn Leu Gln His Glu Ile Ala Thr Leu Ala Glu Ile Arg Ser
325                 330                 335                 340

AGG AAC GGG ATC CAT GCG GAG AGC ACG CTG GAC ATC CTC AAG GCC GAG      2522
Arg Asn Gly Ile His Ala Glu Ser Thr Leu Asp Ile Leu Lys Ala Glu
                345                 350                 355

GGG GAC ATC TAC GTC GCC ATG ATC GAC GGC AAG GTG ATC ACC AAG CTC      2570
Gly Asp Ile Tyr Val Ala Met Ile Asp Gly Lys Val Ile Thr Lys Leu
            360                 365                 370
```

-continued

```
GGG CCG AGG TAC GAC GCC GGC GGG ATC ATC CCC TCC GAC TTC CAT GTC      2618
Gly Pro Arg Tyr Asp Ala Gly Gly Ile Ile Pro Ser Asp Phe His Val
        375                 380                 385

GTG GCG CAC GGC AAC GAC TAC TGC GTC TGG GAG AAG GAA GGC CTC AGG      2666
Val Ala His Gly Asn Asp Tyr Cys Val Trp Glu Lys Glu Gly Leu Arg
    390                 395                 400

GTT CCT GCC GGT AGA AAG CAC TAT TAGCTTTAGC TATAGCGATC GAGTTGCATG    2720
Val Pro Ala Gly Arg Lys His Tyr
405                 410

GTGCTTTGCA ACCCTAGATA ATATATATAC GTACGTGGCT CTAGCTATGA ATCATGCAAT   2780

TTTGCTGCGA GATGTGTACG AGCGAGCTTC GATCGATGTA CGCTTCGTTA TAACTAGCGT   2840

TCTTCGGAAA TAAGTAATCG GAATGTACCC TGTTAATCCT GCAGAAATGT AGGATGAATG   2900

GAATTAACTA GCTACTGTTC GTTTCGATCC TCAAGAAAGA CTTGCAAGAT CTTGTCCAGT   2960

TGACTTCAGT TTTTTACTCC CGCTTTTAGC GTCTGGATAC CGTGGTGGAT TGAAAGCTCA   3020

ACTTGATCCC GTTTGGCCCA GCAATATTAG GCCGTAAGTA AAACGAATGA CACCTGCATA   3080

TTCCGGCCCA AAGCGCACGC TCGTTGTCTC TCATTTAGCG GTCCAAAGAT AATGGGACGA   3140

ATGTTCTTCA CAGCAACGAT TTAGCCTAAC TATAATGGGG CACCTTTCCT TTATAACCCA   3200

AGGAATAAGT TCACTGGTCC CTTAATTTAT CAGCGAGTCT GAAATTTATC CCTAAACCGA   3260

AATACTGTAT ATAATTGGTC CCCCAATTTT CAAAACGGTT CACTTAGAGG ACCC         3314
```

(2) INFORMATION FOR SEQ ID NO: 6:

(i) SEQUENCE CHARACTERISTICS:
(A) LENGTH: 437 amino acids
(B) TYPE: amino acid
(D) TOPOLOGY: linear (ii) MOLECULE TYPE: protein (xi) SEQUENCE DESCRIPTION: SEQ ID NO: 6:

```
Met Gly Lys His His Val Thr Leu Cys Cys Val Val Phe Ala Val Leu
-25                 -20                 -15                 -10

Cys Leu Ala Ser Ser Leu Ala Gln Ala Gln Val Leu Phe Gln Gly Phe
                 -5                   1               5

Asn Trp Glu Ser Trp Arg Lys Gln Gly Gly Trp Tyr Asn Phe Leu His
         10                  15                  20

Glu Lys Val Glu Glu Ile Ala Ser Thr Gly Ala Thr His Val Trp Leu
     25                  30                  35

Pro Pro Pro Ser His Ser Val Ser Pro Gln Gly Tyr Met Pro Gly Arg
 40                  45                  50                  55

Leu Tyr Asp Leu Asp Ala Ser Lys Tyr Gly Thr Glu Ala Glu Leu Lys
                 60                  65                  70

Ser Leu Ile Glu Ala Phe His Asp Lys Asn Val Glu Cys Leu Ala Asp
             75                  80                  85

Ile Val Ile Asn His Arg Cys Ala Asp Tyr Lys Asp Ser Arg Gly Val
         90                  95                 100

Tyr Cys Val Phe Glu Gly Gly Thr Pro Asp Gly Arg Leu Asp Trp Gly
    105                 110                 115

Pro Asp Met Ile Cys Ser Asp Asp Thr Gln Tyr Ser Asn Gly Arg Gly
120                 125                 130                 135

His Arg Asp Thr Gly Ala Gly Phe Gly Ala Ala Pro Asp Ile Asp His
                140                 145                 150

Leu Asn Pro Arg Val Gln Arg Glu Leu Thr Asp Trp Leu Asn Trp Leu
```

-continued

```
            155                 160                 165

Arg Thr His Leu Gly Phe Asp Gly Trp Arg Leu Asp Phe Ala Lys Gly
        170                 175                 180

Tyr Ser Ala Pro Leu Ala Arg Ile Tyr Val Asp Asn Thr Asn Pro Thr
    185                 190                 195

Phe Val Val Gly Glu Ile Trp Ser Ser Leu Ile Tyr Asn Gly Asp Gly
200                 205                 210                 215

Lys Pro Ser Thr Asn Gln Asp Ala Asp Arg Gln Glu Leu Val Asn Trp
                220                 225                 230

Val Glu Gly Val Gly Lys Pro Ala Thr Ala Phe Asp Phe Thr Thr Lys
            235                 240                 245

Gly Ile Leu Gln Ala Ala Val Gln Gly Glu Leu Trp Arg Leu His Asp
        250                 255                 260

Gly Asn Gly Lys Ala Pro Gly Leu Met Gly Trp Met Pro Asp Gln Ala
    265                 270                 275

Val Thr Phe Val Asp Asn His Asp Thr Gly Ser Thr Gln Ser Leu Trp
280                 285                 290                 295

Pro Phe Pro Ser Asp Lys Val Met Gln Gly Tyr Ala Tyr Ile Leu Thr
                300                 305                 310

His Pro Gly Ile Pro Cys Ile Phe Tyr Asp His Val Phe Asp Trp Asn
            315                 320                 325

Leu Gln His Glu Ile Ala Thr Leu Ala Glu Ile Arg Ser Arg Asn Gly
        330                 335                 340

Ile His Ala Glu Ser Thr Leu Asp Ile Leu Lys Ala Glu Gly Asp Ile
    345                 350                 355

Tyr Val Ala Met Ile Asp Gly Lys Val Ile Thr Lys Leu Gly Pro Arg
360                 365                 370                 375

Tyr Asp Ala Gly Gly Ile Ile Pro Ser Asp Phe His Val Val Ala His
                380                 385                 390

Gly Asn Asp Tyr Cys Val Trp Glu Lys Glu Gly Leu Arg Val Pro Ala
            395                 400                 405

Gly Arg Lys His Tyr
        410
```

(2) INFORMATION FOR SEQ ID NO: 7:

(i) SEQUENCE CHARACTERISTICS:
(A) LENGTH: 1519 base pairs
(B) TYPE: nucleic acid
(C) STRANDEDNESS: double
(D) TOPOLOGY: linear (ii) MOLECULE TYPE: cDNA (vi) ORIGINAL SOURCE:
(A) ORGANISM: Rice (Oryzae sativa)
(B) STRAIN: CV. Labelle (vii) IMMEDIATE SOURCE:
(A) LIBRARY: (Lambda gt-11) cDNA
(B) CLONE: alpha-Amy10-C (x) PUBLICATION INFORMATION:
(A) AUTHORS: Yu et al., Su-May
(B) TITLE: Regulation of alpha-amylase-encoding gene expression in germinating seeds and cultured cells of rice
(C) JOURNAL: Gene
(D) VOLUME: in press (xi) SEQUENCE DESCRIPTION: SEQ ID NO: 7:

```
AGCAAACGCT TCTTGTCCCT GTCCCTGCTC ATCCTCCTCC TCGGCTTCTC CTCCAGCTTG     60
```

-continued

```
GCAGCCGGGC AAGTCCTGTT TCAGGGCTTC AACTGGGAGT CGTGGAAGGA GAATGGCGGG    120
TGGTACAACA TGCTGATGGG CAAGGTGGAC GACATCGCCG CCGCCGGCAT CACCCACGTC    180
TGGCTCCCTC CGCCGTCTCA ATCTGTCGCC GAACAAGGCT ACATGCCGGG GCGGCTGTAC    240
GATCTGGACG CTTCCAAGTA CGGCAACGAG GCGCAGCTCA AGTCGCTGAT CGAGGCGTTC    300
CACGGCAAGG GCGTCCAGGT GATCGCCGAC ATCGTCATCA ACCACCGCAC GGCGGCAGCA    360
AGCACAGGAC GGCCGCGGCA TCTACTGCCT CTTCGAGGGC GGGCAGCGCG ACTCCCGCCT    420
CGACTGGGGC CCGCACATGA TCTGCCGCGG CGACCCCTAC GGCGACGGCA CCGGCAACCG    480
ACACCGCTAG CCGACTTGGC CTGACATCGA CCACCTCAAC AAGCGCGTCA CGAGCTCATC    540
GGCTGGCTCG ACTGGCTCGA CTGGCTCAAG CATAGGAACC AATTGGGCCT TCGACCCTGA    600
CTGGCCTCCT CGACTTCCGC CAACGCGCGC GTTACTCCCG CCGTACGTAT CTGCAAAGAG    660
CTATCATCGA CTGCCACCGA GACCGGACTA TCGCCGATGG CCGAGACTAT AGGACGTACG    720
CTGGCGTAGC GAGCTGCGGG ACGGCTAAAG CCGGACTATG ACCATGAACG CAACGACCGG    780
CAGTAGCTGG TCAACTGGGT CGACCGTGCG GCTGGACCAA CATCATTCTA AATGCTTCGA    840
CTTCACCACC TAATGGGCAT ACTCAACGAA TCGCCAGCTT GGTAGGTGCG AGCTATTGGC    900
GCCTCCTGGG CGTAGAGACG GCCAAGGCGC CACAGGCATG CATTACGGAG TAGTGGCCGG    960
CTAAGGGACG ACCTTTGATC TGACGAACCA CTGACTACCA GGCGTCGATC CGCAGCATCA   1020
TGTGGCTGTT TCCCTCCGAC AAGGTCATGC AGGGTACGCT ACAGTACTCA CCACCCGGCA   1080
ACCCATGCAC TTTCTACGAC CATTTCTTCG ACTGGGGCCA CAAGGAGGAG ATCGAGCGCC   1140
TGGTATCGAC TCAAGAAACC GCAGGGATCC ACCCGGCGAG CGAGCTGCGT ATCATGGAGG   1200
CTGACAGCGA TCTCTACCTC GCCGAGATCG ACGGAAAGGT CATCACGAAG GTCGGACCAA   1260
GATACGACGT CGAGCACCTC ATCCCGAAGC TTCCAGGTCG TCGCGCACGT GACGGCTACC   1320
GTCTGGGAGA AATTGAGCGG TGGAGAGGCC ATTAAAGCAG ATTTATTTCC TGCATTTTCA   1380
CCTCGACGTA TAACATATAC ATGTGATGGC AACGAGTTGT ATGCTGTATC TGATCTGAAC   1440
TATGTACGCG ATTGTCCACA AAGTACTACC TCCGTAAATA AAGTGAGGAT ATGGAACATG   1500
CGTTTGCATG CATGGTTTT                                                1519
```

(2) INFORMATION FOR SEQ ID NO: 8:

(i) SEQUENCE CHARACTERISTICS:
(A) LENGTH: 2938 base pairs
(B) TYPE: nucleic acid
(C) STRANDEDNESS: double
(D) TOPOLOGY: linear (ii) MOLECULE TYPE: DNA (genomic)

(vi) ORIGINAL SOURCE:
(A) ORGANISM: Rice (Oryzae sativa)
(B) STRAIN:

(vii) IMMEDIATE SOURCE:
(A) LIBRARY: (EMBL) genomic
(B) CLONE: alpha-Amy3-C (ix) FEATURE:
(A) NAME/KEY: CDS
(B) LOCATION: join (1081..1170, 1295..2230, 2319..2600)

(ix) FEATURE:
(A) NAME/KEY: mat_peptide
(B) LOCATION: join (1156..1170, 1295..2230, 2319..2600)

(xi) SEQUENCE DESCRIPTION: SEQ ID NO: 8:

-continued

```
GATCTTCAAC CACCTGTGCT AGCTACTCCA CTGCTCCATA GGCAATCATC AATCAGTAAT     60

CCGTTCTGAA AAGAAGATAT AGGTGTGCGC AATCAGGAAC GTTCTAGTTC GTGCTAGAAA    120

TCAGCAGCTC CTAAGTTAGC ATCTCGATGA ACTTAAATGC TCGCTGCGGG CGTCCGGCGG    180

AGATGAAGTT TGTGATAAAC TTGGTCATGA CATTCATATA TGTGCCTGGT GTACGGAGTA    240

GTTCATCAGC AAACATACAC CTACTTCTAC CTTATCCATT TGGATTGCTC ATGGCGGCTT    300

TGATATGGAA TTTGTAATGA ACTTGGTTAT GACTTATGAC ATACTGATAC TCGTAACATT    360

CATAGATACT GACATAAATT CATCAACTAC AATAGATGAG ATGGCTAGTC TTAGTAGAAC    420

AGTAGTCTCT CTTTCCGGCT TGCTCCATTG GCTGATGACG ATGAACAACT CGGACTCATT    480

GATTCCAGCA TTATCTGATT CTCGCATTTC GAGGTCCGGA TTAGGGTCTC ACCGAGATGT    540

GGATAGAATT GCCATGTCAG GAATTGAAGG AGGACGAGCC ATATGTGCAT ATACATGACG    600

GGAGATCAAC CGGCCAGTCA AGAGGCTAAC TGCAACCCTA TTATATACGA TCAGCCTGCT    660

AGAACACGTA GCACTGTCTT TTTTGTCTGA ACTCTGAAGA TGAAAGGTTC AGAGAAATGG    720

CTCGCCTTAT CCAAGCCGGC GATGGATGGA GGAGGAGGTA GCCGGCGCCC GCCTCAGGCA    780

GTCGTCGCGA TCACGCCGCC GCATCCCGTC GCCTTGGAGA CCGGGCCCCG ACGCGGCCGA    840

CGCGGCGCCT ACGTGGCCAT GCTTTATTGC CTTATCCATA TCCACGCCAT TTATTGTGGT    900

CGTCTCTCCT GATCATTCTC ATTCCCCTGC CACGGTGACC GTGCCCCCGG TGTTCTATAT    960

ATGCCCCCCG ACGTCGAGGT CATTCGCCAC GAACACATCG ATCATCCATC ATCTACAAGA   1020

GATCGATCAG TAGTGGTTAG CAGCAACTCA CTATCGAACA CGGTTTCAGC TTACACAGAT   1080

ATG AAG AAC ACC AGC AGC TTG TGT TTG CTG CTC CTC GTG GTG CTC TGC     1128
Met Lys Asn Thr Ser Ser Leu Cys Leu Leu Leu Leu Val Val Leu Cys
-25                 -20                 -15                 -10

AGC TTG ACC TGT AAC TCG GGT CAA GCA CAG GTC CTC TTC CAG             1170
Ser Leu Thr Cys Asn Ser Gly Gln Ala Gln Val Leu Phe Gln
                 -5                   1               5

GTACGTAGTA CTCTACTACC CATCACTTTC TGTGAAGACT TTTGCTGAAG AAACACATTA   1230

GAATTTTGAG ATATTTATGT GTGATCGATT GATCACTTAC CTACTTATAA CATGCATCAT   1290

GCAG GGT TTC AAC TGG GAG TCG TGG AAG CAG CAG GGT GGC TGG TAC AAC    1339
     Gly Phe Asn Trp Glu Ser Trp Lys Gln Gln Gly Gly Trp Tyr Asn
                      10                  15                  20

ATG TTG AAA GGC CAA GTC GAC GAC ATC GCC AAG GCC GGG GTC ACC CAC     1387
Met Leu Lys Gly Gln Val Asp Asp Ile Ala Lys Ala Gly Val Thr His
                 25                  30                  35

GTC TGG CTG CCG CCG CCG TCG CAC TCC GTG GCG CCG CAG GGG TAC ATG     1435
Val Trp Leu Pro Pro Pro Ser His Ser Val Ala Pro Gln Gly Tyr Met
             40                  45                  50

CCG GGG CGT CTC TAC GAC CTG GAC GCG TCC AAG TAC GGC ACG GCG GCG     1483
Pro Gly Arg Leu Tyr Asp Leu Asp Ala Ser Lys Tyr Gly Thr Ala Ala
         55                  60                  65

GAG CTC AAG TCG CTG ATC GCG GCG TTC CAC GGG AAG GGC GTC CAG TGC     1531
Glu Leu Lys Ser Leu Ile Ala Ala Phe His Gly Lys Gly Val Gln Cys
     70                  75                  80

GTC GCC GAC GTC GTG ATC AAC CAC CGG TGC GCC GAG AAG AAG GAC GCC     1579
Val Ala Asp Val Val Ile Asn His Arg Cys Ala Glu Lys Lys Asp Ala
 85                  90                  95                 100

CGC GGC GTG TAC TGC GTG TTC GAG GGC GGG ACG CCC GAC CGC CTC GAC     1627
Arg Gly Val Tyr Cys Val Phe Glu Gly Gly Thr Pro Asp Arg Leu Asp
                105                 110                 115

TGG GGC CCC GGC ATG ATC TGC AGC GAC GAC ACG CAG TAC TCC GAC GGC     1675
Trp Gly Pro Gly Met Ile Cys Ser Asp Asp Thr Gln Tyr Ser Asp Gly
```

-continued

```
            120                 125                 130

ACG GGC CAC CCG GAC ACC GGC GAG GGG TTC GGC GCG GCG CCC GAC ATC     1723
Thr Gly His Pro Asp Thr Gly Glu Gly Phe Gly Ala Ala Pro Asp Ile
        135                 140                 145

GAC CAC CTC AAC CCG CGC GTC CAG CGG GAG CTC ACC GAC TGG CTC AAC     1771
Asp His Leu Asn Pro Arg Val Gln Arg Glu Leu Thr Asp Trp Leu Asn
    150                 155                 160

TGG CTC AAG TCC GAC GTC GGC TTC GAC GGC TGG CGC CTC GAC TTC GCC     1819
Trp Leu Lys Ser Asp Val Gly Phe Asp Gly Trp Arg Leu Asp Phe Ala
165                 170                 175                 180

AAG GGA TAC TCC ACG GAC ATC GCT AAG ATG TAC GTC GAG AGC TGC AAG     1867
Lys Gly Tyr Ser Thr Asp Ile Ala Lys Met Tyr Val Glu Ser Cys Lys
                185                 190                 195

CCG GGC TTC GTC GTC GCC GAG ATA TGG AAC TCG CTG AGC TAC AAC GGC     1915
Pro Gly Phe Val Val Ala Glu Ile Trp Asn Ser Leu Ser Tyr Asn Gly
            200                 205                 210

GAC GGC AAG CCG GCG GCC AAC CAG GAC CAG GGC CGG CAG GAG CTG GTG     1963
Asp Gly Lys Pro Ala Ala Asn Gln Asp Gln Gly Arg Gln Glu Leu Val
        215                 220                 225

AAC TGG GTG AAC GCC GTC GGC GGG CCG GCG ATG ACG TTC GAC TTC ACC     2011
Asn Trp Val Asn Ala Val Gly Gly Pro Ala Met Thr Phe Asp Phe Thr
    230                 235                 240

ACC AAG GGC CTC CTG CAG GCG GGC GTC CAG GGC GAG CTG TGG CGG CTG     2059
Thr Lys Gly Leu Leu Gln Ala Gly Val Gln Gly Glu Leu Trp Arg Leu
245                 250                 255                 260

CGC GAC GGC AAC GGC AAG GCC CCC GGC ATG ATC GGG TGG CTG CCA GAG     2107
Arg Asp Gly Asn Gly Lys Ala Pro Gly Met Ile Gly Trp Leu Pro Glu
                265                 270                 275

AAG GCC GTC ACG TTC GTC GAC AAC CAC GAC ACC GGC TCG ACG CAG AAG     2155
Lys Ala Val Thr Phe Val Asp Asn His Asp Thr Gly Ser Thr Gln Lys
            280                 285                 290

CTT TGG CCG TTC CCC TCC GAC AAG GTC ATG CAG GGC TAC GCC TAC ATC     2203
Leu Trp Pro Phe Pro Ser Asp Lys Val Met Gln Gly Tyr Ala Tyr Ile
        295                 300                 305

CTC ACC CAC CCC GGA GTC CCC TGC ATC GTAAGCAAAC CATGCATTAT           2250
Leu Thr His Pro Gly Val Pro Cys Ile
    310                 315

AGTATTATAT ACCATGTCCT GATTAACCTC CACCGTACAC GTGTCCTGAT GAACGCTTCT   2310

TGTGGCAG TTC TAC GAC CAC ATG TTC GAC TGG AAC CTG AAG CAG GAG ATA    2360
         Phe Tyr Asp His Met Phe Asp Trp Asn Leu Lys Gln Glu Ile
                 320                 325                 330

ACC GCG CTG GCG GCG ATC AGG GAG AGG AAC GGC ATC AAC GCC GGG AGC     2408
Thr Ala Leu Ala Ala Ile Arg Glu Arg Asn Gly Ile Asn Ala Gly Ser
            335                 340                 345

AAG CTC CGG ATC GTC GTC GCC GAC GCC GAC GCA TAC GTC GCC GTC GTC     2456
Lys Leu Arg Ile Val Val Ala Asp Ala Asp Ala Tyr Val Ala Val Val
        350                 355                 360

GAC GAG AAG GTC ATG GTG AAG ATC GGG ACG AGG TAC GAC GTG GGC AAC     2504
Asp Glu Lys Val Met Val Lys Ile Gly Thr Arg Tyr Asp Val Gly Asn
    365                 370                 375

GCG GTG CCG TCG GAT TTC CAT CAG ACG GTG CAC GGC AAG GAC TAC AGC     2552
Ala Val Pro Ser Asp Phe His Gln Thr Val His Gly Lys Asp Tyr Ser
380                 385                 390                 395

GTC TGG GAG AAG GGG TCC CTC CGC GTC CCG GCG GGG CGG CAC CTA TAGCGGGCTC
2607
Val Trp Glu Lys Gly Ser Leu Arg Val Pro Ala Gly Arg His Leu
                400                 405                 410

AAGCCCTAAA CTGAACGGGA TAGTCATGCT CAAACCAGTT TCTACACGGC AAGAATTTAC   2667
```

-continued

```
TGATTCTTAT ACTTTTGCAG TCAATTAAAT TATGGTTTTT ATATATGTAA TTTTGTATCC   2727

GATTGTAGCG TTCGAATAAG TAGGCAGGCT CTCTAGCCTC TAGGTTAATT GCGGGGCATA   2787

TGTAGCTTGC CAGTTAATTG TGTTTGTATC ACGCAGTTTG TAACCGTTGG TGCAATATAT   2847

AATGTCAGGT TCAGGATGCA GTAAAAAATC ATACTGCACC GATCAGTGAG TTTTTATATA   2907

CTCGTTTTAA AAGTGAGCAC AAGTACTAGT T                                  2938
```

(2) INFORMATION FOR SEQ ID NO: 9:

(i) SEQUENCE CHARACTERISTICS:
(A) LENGTH: 435 amino acids
(B) TYPE: amino acid
(D) TOPOLOGY: linear (ii) MOLECULE TYPE: protein (xi) SEQUENCE DESCRIPTION: SEQ ID NO: 9:

```
Met Lys Asn Thr Ser Ser Leu Cys Leu Leu Leu Leu Val Val Leu Cys
-25                 -20                 -15                 -10

Ser Leu Thr Cys Asn Ser Gly Gln Ala Gln Val Leu Phe Gln Gly Phe
                -5                   1               5

Asn Trp Glu Ser Trp Lys Gln Gln Gly Gly Trp Tyr Asn Met Leu Lys
        10                  15                  20

Gly Gln Val Asp Asp Ile Ala Lys Ala Gly Val Thr His Val Trp Leu
    25                  30                  35

Pro Pro Pro Ser His Ser Val Ala Pro Gln Gly Tyr Met Pro Gly Arg
 40                 45                  50                  55

Leu Tyr Asp Leu Asp Ala Ser Lys Tyr Gly Thr Ala Ala Glu Leu Lys
                60                  65                  70

Ser Leu Ile Ala Ala Phe His Gly Lys Gly Val Gln Cys Val Ala Asp
            75                  80                  85

Val Val Ile Asn His Arg Cys Ala Glu Lys Lys Asp Ala Arg Gly Val
        90                  95                  100

Tyr Cys Val Phe Glu Gly Gly Thr Pro Asp Arg Leu Asp Trp Gly Pro
    105                 110                 115

Gly Met Ile Cys Ser Asp Asp Thr Gln Tyr Ser Asp Gly Thr Gly His
120                 125                 130                 135

Pro Asp Thr Gly Glu Gly Phe Gly Ala Ala Pro Asp Ile Asp His Leu
                140                 145                 150

Asn Pro Arg Val Gln Arg Glu Leu Thr Asp Trp Leu Asn Trp Leu Lys
            155                 160                 165

Ser Asp Val Gly Phe Asp Gly Trp Arg Leu Asp Phe Ala Lys Gly Tyr
        170                 175                 180

Ser Thr Asp Ile Ala Lys Met Tyr Val Glu Ser Cys Lys Pro Gly Phe
    185                 190                 195

Val Val Ala Glu Ile Trp Asn Ser Leu Ser Tyr Asn Gly Asp Gly Lys
200                 205                 210                 215

Pro Ala Ala Asn Gln Asp Gln Gly Arg Gln Glu Leu Val Asn Trp Val
                220                 225                 230

Asn Ala Val Gly Gly Pro Ala Met Thr Phe Asp Phe Thr Thr Lys Gly
            235                 240                 245

Leu Leu Gln Ala Gly Val Gln Gly Glu Leu Trp Arg Leu Arg Asp Gly
        250                 255                 260

Asn Gly Lys Ala Pro Gly Met Ile Gly Trp Leu Pro Glu Lys Ala Val
    265                 270                 275
```

-continued

```
Thr Phe Val Asp Asn His Asp Thr Gly Ser Thr Gln Lys Leu Trp Pro
280                 285                 290                 295

Phe Pro Ser Asp Lys Val Met Gln Gly Tyr Ala Tyr Ile Leu Thr His
                300                 305                 310

Pro Gly Val Pro Cys Ile Phe Tyr Asp His Met Phe Asp Trp Asn Leu
            315                 320                 325

Lys Gln Glu Ile Thr Ala Leu Ala Ala Ile Arg Glu Arg Asn Gly Ile
        330                 335                 340

Asn Ala Gly Ser Lys Leu Arg Ile Val Val Ala Asp Ala Asp Ala Tyr
    345                 350                 355

Val Ala Val Val Asp Glu Lys Val Met Val Lys Ile Gly Thr Arg Tyr
360                 365                 370                 375

Asp Val Gly Asn Ala Val Pro Ser Asp Phe His Gln Thr Val His Gly
                380                 385                 390

Lys Asp Tyr Ser Val Trp Glu Lys Gly Ser Leu Arg Val Pro Ala Gly
            395                 400                 405

Arg His Leu
        410
```

(2) INFORMATION FOR SEQ ID NO: 10:

(i) SEQUENCE CHARACTERISTICS:
(A) LENGTH: 11 base pairs
(B) TYPE: nucleic acid
(C) STRANDEDNESS: single
(D) TOPOLOGY: linear (ii) MOLECULE TYPE: cDNA (xi) SEQUENCE DESCRIPTION: SEQ ID NO: 10:

GTTGCGTTTC T 11

(2) INFORMATION FOR SEQ ID NO: 11:

(i) SEQUENCE CHARACTERISTICS:
(A) LENGTH: 20 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO:11:

ACGTCCTGTA GAAACCCCAA 20

(2) INFORMATION FOR SEQ ID NO: 12:

(i) SEQUENCE CHARACTERISTICS:
(A) LENGTH: 22 base pairs
(B) TYPE: nucleic acid
(C) STRANDEDNESS: single
(D) TOPOLOGY: linear (ii) MOLECULE TYPE: other nucleic acid
(A) DESCRIPTION: /desc = "primer"

(xi) SEQUENCE DESCRIPTION: SEQ ID NO: 12:

AGTTCAGTTC GTTGTTCACA CA 22

(2) INFORMATION FOR SEQ ID NO: 13:

(i) SEQUENCE CHARACTERISTICS:
(A) LENGTH: 40 base pairs

-continued

```
        (B) TYPE: nucleic acid
        (C) STRANDEDNESS: single
        (D) TOPOLOGY: linear

   (ii) MOLECULE TYPE: cDNA

   (xi) SEQUENCE DESCRIPTION: SEQ ID NO: 13:

TGGAGCCCAC AACGCTATCC AAGGCTTTAT CTAACTTCCT                          40


(2) INFORMATION FOR SEQ ID NO: 14:

    (i) SEQUENCE CHARACTERISTICS:
        (A) LENGTH: 40 base pairs
        (B) TYPE: nucleic acid
        (C) STRANDEDNESS: single
        (D) TOPOLOGY: linear

   (ii) MOLECULE TYPE: cDNA

   (xi) SEQUENCE DESCRIPTION: SEQ ID NO: 14:

ATTGGCCTCC TTTTTATCCT CTTTTAAATG AGCGCAACTC                          40


(2) INFORMATION FOR SEQ ID NO: 15:

    (i) SEQUENCE CHARACTERISTICS:
        (A) LENGTH: 40 base pairs
        (B) TYPE: nucleic acid
        (C) STRANDEDNESS: single
        (D) TOPOLOGY: linear

   (ii) MOLECULE TYPE: cDNA

   (xi) SEQUENCE DESCRIPTION: SEQ ID NO: 15:

GTCGCCGTGC CGTTGCGTTT CTCGTTAGGA GCAACTGAAC                          40
```

APPLICATION OF α-AMYLASE GENE PROMOTER AND SIGNAL SEQUENCE IN THE PRODUCTION OF RECOMBINANT PROTEINS IN TRANSGENIC PLANTS AND TRANSGENIC PLANT SEEDS

RELATED APPLICATIONS

This application is a continuation of U.S. patent application Ser. No. 08/947,201, filed on Oct. 8, 1997, now abandoned, which is continuation of U.S. patent application Ser. No. 08/509,962, filed Aug. 1, 1995, now abandoned which is a continuation-in-part of U.S. patent application Ser. No. 08/343,380 filed Nov. 22, 1994, now U.S. Pat. No. 5,712,112, which is a continuation application of U.S. patent application Ser. No. 07/973,324 filed Nov. 4, 1992, now U.S. Pat. No. 5,460,952. The predecessor applications are incorporated herein by reference.

FIELD OF THE INVENTION

This invention relates to a method for producing a gene product, in particular to a method for the mass production of a desired gene product by expressing a gene encoding said gene product in plant host cells, whereby said desired gene product can be recovered from the culture medium of said plant host cells. More particularly, a novel gene expression system comprising the promoter region of an alpha-amylase gene is established, enabling the formation of transgenic plant cells, transgenic plants and transgenic plant seeds, as well as recombinant proteins produced thereby. It is also anticipated that the transgenic plant seeds thus formed, when being subject to germination, may find application in the fermentation/brewing industry.

BACKGROUND OF THE INVENTION

The plant cell culture expression system has several advantages over the bacterial, yeast or Baculovirus expression systems. Bacteria do not, and yeasts only limitedly, carry out post-translational modifications of the expressed proteins. Plant cells are eukaryotic and able to perform sophisticated protein modifications which are often necessary for the proper function of proteins.

Although Baculovirus is a potent transformation vehicle for higher eukaryotes and generally performs satisfactory modifications of proteins, the cost for culturing baculovirus is much higher than that for plant cells. In addition, the host cells are eventually lysed by Baculovirus and thousands of host proteins along with the expressed transformation protein are mixed and released into the culture medium, which makes purification of the expressed transformation protein difficult.

The culture medium for plant cells contains mainly salts and vitamins and therefore, it costs much less than that used to culture insect cell lines which are used for the Baculovirus transfection. Moreover, the culture medium for plant cells will not need a supply of serum, whereas almost all animal cell cultures cannot survive without serum. In addition, since plant cells are eukaryotes, the expressed proteins therein will be appropriately post-translationally modified so as to render said proteins capable of functioning and being secreted out of the plant cells. Although no one has yet made a deeper understanding of the mechanism of protein secretion in plant cells, the common belief at present is that it could be similar to the secretory mechanism in animals.

Plant cell cultures are a potential commercial source of medicines, dyes, enzymes, flavoring agents and aromatic oils. Plant cell culture production of such compounds are sought when (1) they are produced by the plant in small quantities or in fleeting or unharvestable developmental stages of the plant's life cycle; (2) when they are produced by plants which are not amenable to agriculture or are native to vanishing or inaccessible environments; and (3) when the compounds cannot be satisfactorily synthesized in vitro or by other biosynthesis systems.

Attempts to produce products by plant cell culture, however, are often commercially unsuccessful due to such factors as insufficient production and secretion of the desired product, poor cell growth, and difficulties in maintaining the appropriate cell type in culture.

The callus alpha-amylase (α-amylase) expression system has features which make it of potential use to plant cell fermentation technology, namely its high level of expression, sustained expression, expression irrespective of either the tissue of origin of the cell culture or tissue formation in the cell culture, and its product secretion. Although rice callus itself may not be an ideal source of commercial α-amylase, the gene regulatory regions responsible for the high expression could be used, with the aid of recombinant DNA technology and plant transformation, to achieve high expression of other valuable proteins (Carl R. Simmons, et al (1991), Biotechnology and Bioengineering, 38: 545–551).

Starch includes straight-chain starch and branched starch, two types of polysacchardies, and is the basic stored nutrient component in cereal grains (T. Akazawa et al (1985), Ann. Rev. Plant Physiol., 36: 441–472). During the initial germinating period of cereal seeds, the aleurone layer cells will synthesize α-amylase. Alpha-amylase, α-glucosidase and enzymes restricting dextrinase are secreted into the endosperm and together hydrolyze starch to form glucose and maltose, so as to provide the nutrients needed for the growth of the germ (J. C. Rogers and C. Milliman, J. Biol. Chem., 259 (19): 12234–12240, 1984; Rogers, J. C., J. Biol. Chem., 260: 3731–3738, 1985). Other enzymes contributing to starch hydrolysis include β-amylase which can hydrolyze starch to form maltose and a small amount of glucose. In a dry seed, β-amylase normally exists in an inactive form in the endosperm due to protein disulfide bonding. When the seed germinates, the aleurone layer cells will be subjected to the induction by gibberellic acid ($GA_3$) to produce protease, which can destroy the disulfide bond and release the active form of β-amylase. The above four enzymes take part in the hydrolysis of starch during the germination of seeds. However, α-amylase is the most active and holds the most important role (Akazawa, T., et al (1985), Ann. Rev. Plant Physiol., 36: 441–472).

It is known that $GA_3$ exerts a direct influence over the expression of α-amylase (Chandler, P. M., et al (1984), Mol. Biol., 3: 401–418). When rice seeds are treated with $GA_3$, the new synthesis of α-amylase mRNA by the aleurone layer cells increases to 50 to 100-fold of the control value (no $GA_3$) (O'Neill, S. D., et al (1990), Mol. Gene. Genet., 221: 235–244). In reality, the regulation of α-amylase gene expression by $GA_3$ has provided a very ideal model for studying the mechanism of hormonal regulation of gene expression in plants (Ho, T. H. D., et al (1987), "Regulation of gene expression in barley aleurone layers," In: *Molecular Biology of Plant Growth Control,* pp.35–49. St. Louis, Mo.: Alan R. Liss, Inc.).

Hitherto, α-amylase genes from rice, barley and wheat have been cloned and subjected to further study and analysis. The results show that these cereal-type α-amylase isozymes or isoforms are all manufactured by several types of α-amylase genes (Baulcombe, D. C., et al (1987) Mol. Gen. Genet., 209: 33–40); Huang, N., et al (1990a), Plant Mol. Biol., 14: 655–668, Knox, C. A. P., et al (1987), Plant Mol. Biol., 9: 3–17).

The α-amylase secreted from the aleurone layer cells during the germinating period of the seed of barley and wheat comprises two classes, the high isoelectric point and low isoelectric point. In barley, there are around 7 α-amylase genes which belong to the high isoelectric point and 3–4 genes which belong to the low isoelectric point (B. Khursheed and J. C. Rogers, J. Biol. Chem., 263: 18593–18960, 1988).

Currently, 7 α-amylase cDNA and 9 α-amylase genomic DNA groups of barley have been cloned (Chandler, P. M., et al (1984), Plant. Mol. Biol., 3: 401–418; J. Deikman and R. L. Jones, Plant Physiol., 78: 192–198, 1985; Khrusheed & Rogers (1988), supra; Knox, C. A. P., et al (1987), supra). The α-amylase genes of wheat are grouped into α-Amyl, α-Amy2 and α-Amy3. Alpha-Amy1 has a high isoelectric point while α-Amy2 has a low isoelectric point, and each has more than 10 genes which are expressed in germinating seeds. Alpha-amylase α-Amy3 includes 3–4 genes which are expressed in immature seeds (Baulcombe et al (1987), supra).

With regard to the study of rice α-amylase genes, the α-amylase genes thereof have not been classified into the high isoelectric point group and the low isoelectric point group as was done in the study of barleys and wheats. In reality, MacGregor, A. W., et al (Cereal Chem., 65: 326, 1988) applied the analytical method of isoelectric point electrophoresis and found that rice α-amylase isomers had a pI value of less than 5.5.

Therefore, it is possible that rice does not have any isoform of high isoelectric point. Huang, N., et al (Nucl. Acids. Res., 18: 7007–7014, 1990b) grouped the 10 rice α-amylase genes into 5 groups by cross hybridization experiment and confirmed their distribution in 5 chromosomes (Ranjhan et al, the original manuscript is still under preparation). O'Neill et al (Mol. Gene. Genet. 221: 235–244, 1990) made the first more detailed study of the cDNA pOS103 and pOS137 of rice α-amylase. The α-amylase manufactured from pOS103 and pOS137 has a precursor protein of a molecular weight of 48 KDa.

When this enzyme is secreted out of the cell, the signal peptide chain of the precursor protein will be cleaved off. Accordingly, the molecular weight of mature α-amylase is about 45–46 KDa and the isoelectric point thereof is predicted to be about 6.0. However, Kumagai, M. H., et al (Gene, 94: 209–216, 1990) subcloned pOS103 into the cells of Saccharomyces, to allow the Saccharomyces to secrete α-amylase into the culture medium, and it was found that the molecular weight of α-amylase is about 44–45 KDa and that the isoelectric point is about 4.7 to 5.0.

On the other hand, transformation of dicotyledonous plants with *Agrobacterium tumefaciens* is well established and widely used. A number of foreign genes carried between the T-DNA borders of the Ti plasmid in Agrobacterium have been delivered to plant cells, integrated into the chromosome, and stably inherited by subsequent generations. This, however, has not been the case for monocotyledonous plants in general. In the past, the monocots and particularly the graminaceous crop species have been considered to be outside the Agrobacterium host range (Bevan, M. W., Nucl. Acids Res., 12: 8711–8721, 1984; Declene, M., Phytopathol. Z. 113: 81–89). Gene transfer methods developed from economically important monocotyledonous species have been restricted to the directed transfer of DNA into protoplasts, or particle discharge methods of direct DNA transfer into intact cells of embryomic callus or suspension cells.

In recent years, more and more data on the transformation of monocots using Agrobacterium have been accumulated. The demonstration of Agrobacterium T-DNA integration into genomic DNA of *Asparagus officinalis* (Bytebier., B., et al (1987), Proc. Natl. Acad. Sci. USA, 84:5345–5349) and *Dioscorea bulbifera* (Schafer, W., et al (1987), Nature, 327: 529–531) first indicated that some monocot species possess the potential to be transformed by Agrobacterium. Later, a report of T-DNA integration into the genomic DNA of rice, *Oryza sativa* (Raineri, D. M., et al (1990), Biotechnology, 8: 33–38), further showed that graminaceous crop plants can be transformed by Agrobacterium. Recently, foreign genes have been successfully transferred into corn, and regeneration of plants and detection of the transferred genes in the F1 progeny have been demonstrated (Gould, J. et al (1991), Plant Physiol., 95: 426–434). Therefore, the Agrobacterium-mediated gene transfer system seems to be applicable for transformation of monocot plants.

Agrobacterium-mediated transformation is a complex process and several factors are involved (for review, see Hooykaas, P. J. J., Plant Mol. Biol., 13: 327–336, 1989). Activation of the virulence system is one of the early important steps in plant tumor induction (Garfinkrl, D. J., J. Bacteriol., 144: 732–743, 1980). The vir genes on the Ti plasmid are silent until they become induced by certain plant factors, which in tobacco have been identified as the phenolic compounds acetosyringone and α-hydroxy-acetosyringone (Stachel, S. E., et al (1985), Nature, 318: 624–629). These compounds are released from plant tissue, especially after wounding, which has long been known to be a prerequisite for plant tumorigenesis via Agrobacterium. Although initially, it was generally thought that monocot species were not susceptible to Agrobacterium, some monocot species (e.g., Asparagus) are prone to tumor formation after T-DNA transfer (Hernalsteens, J. P., et al (1984), EMBO J., 3: 3039–3041). Tumor formation on discs of the monocot Dioscorea (yam) by Agrobacterium requires a pre-incubation with exudates from dicot plants (Schafer, W., et al (1987), Nature, 327: 529–531), indicating that some monocots probably do not produce enough inducers to activate the expression of the vir gene on the Ti plasmid transferred by Agrobacterium.

Toxins or inhibitors which inhibit the growth of *Agrobacterium tumefaciens* and the expresion of vir genes on the Ti plasmid have been shown to be present in wheat (Usami, S., et al (1988), Proc. Natl. Acad. Sci. USA, 85: 3748–3752), and corn (Sahi, S. U., et al (1991), Proc. Natl. Acad. Sci. USA, 87: 3879–3883), and might cause problems during attempts to transform monocots with Agrobacterium. Nevertheless, wheat and oats have been shown to contain substances which induce the expression of the vir locus of the Ti plasmid and the T-DNA processing reaction, although the inducing substance of wheat differs from acetosyringone (Usami, S., et al (1988), supra).

Previously, it was reported that potato suspension culture (PSC) is essential for the Agrobacterium-mediated transformation of Indica type rice (Chan, M. T., et al, "Transformation of Indica rice (*Oryza sativa* L.) mediated by Agrobacterium," Plant Cell Physiol. (1992), 33: 577–583). PSC is rich in the phenolic compounds acetosyringone (AS) and sinapinic acid (SA). Although the role of these two compounds in the success or efficiency of transformation is not yet known, the results imply that transformation of monocots, at least rice, using Agrobacterium can be improved by the addition of certain substances.

The age and physiological states of plant tissues have been shown to be important for Agrobacterium-mediated transformation (An, G. et al (1986), Plant Physiol., 81: 301–305; Chan, M. T., et al (1992), supra); H. H. Chang and M. T. Chan, Bot. Bull. Academia Sinica, 32: 171–178, 1991; Dale, P. J., et al (1989), Plant Sci., 63: 237; Gould, J. et al (1991), supra; Hernalsteens J. P., et al (1984), supra).

These studies suggest that infection with Agrobacterium and T-DNA transfer should take place in monocots if suitable tissues are used for transformation. It was previously shown that young tissues of rice root have a greater potential to be transformed by Agrobacterium if appropriate conditions are applied (Chan, M. T., et al (1992), supra), and it was assumed that young tissues may contain relatively fewer inhibitors or more virulence inducers. Therefore, a combination of immature embryos and PSC for transformation of rice can be used in the present invention.

This invention is based on the inventors' discovery that, in addition to regulation by gibberellic acid ($GA_3$) in germinating seeds of rice, the expression of α-amylase genes in suspension-cultured cells of rice is regulated by the level of carbohydrate present in the culture medium (Yu, Su-May et al. (1991), J. Biol. Chem., 266: 21131–21137).

The synthesis of α-amylases and levels of their mRNA are greatly induced under sucrose starvation. An increase of α-amylase synthesis is assumed to accelerate hydrolysis of cellular starch as an energy source when exogenous carbon source is depleted. Under a normal growth condition with an adequate supply of sugars in the medium, the expression of α-amylase genes is subject to metabolite repression. It was further observed that α-amylases synthesized by the cultured rice cells are secreted into the culture medium and can account for about 15–20% of the total proteins present in the medium during periods of sugar depletion.

It would therefore be advantageous to develop a gene expression system in plant cell culture by constructing a vector expressible in plant host cells utilizing the promoter and the signal peptide sequences of an α-amylase gene. Any foreign gene can be linked downstream of said promoter and signal peptide encoding sequences. This construct would then be used to transform a compatible plant host cell.

Theoretically, the α-amylase promoter would control the expression of foreign genes in said plant cells and the secretion of the proteins into the medium. Such an expression system therefore has a high potential to express and/or secrete large quantities of any important protein into the medium, greatly facilitating purification of the expressed protein.

To aid in the procedure of screening and/or to enhance further the expression efficiency of the gene expression system constructed above, said gene expression system may further comprise a suitable marker gene, a reporter gene, an antibiotic-resistance gene and/or an enhancer gene, all of which can be those well known by an artisan of ordinary skill in the relevant art (Maniatis, T., et al, "Molecular Cloning: A Laboratory Mannual," pressed by Cold Spring Harbor Laboratory, 2nd edi., 1989).

SUMMARY OF THE INVENTION

Accordingly, in one aspect of the present invention, a method is provided for producing a gene product by expressing a gene encoding said gene product in plant host cells, comprising the steps of: constructing a vector expressible in plant host cells, said vector comprising a promoter region derived from an α-amylase gene of a plant, and a gene encoding a desired gene product; transforming a compatible plant host cell with said vector; cultivating the resultant transformant host cell; subjecting said cultivated transformant host cell to a sugar-depleted or sugar-free condition to promote the expression of said gene under the control of said promoter region; and recovering the expressed gene product.

In another aspect of the present invention, a method is provided for producing a gene product by expressing a gene encoding said gene product in plant host cells, comprising the steps of constructing a vector expressible in plant host cells, said vector comprising a promoter region derived from an α-amylase gene of a plant, and a gene encoding a desired gene product, said a promoter region including the promoter and a DNA sequence encoding the signal peptide; transforming a compatible plant host cell with said vector; cultivating the resultant transformant host cell in a suitable culture medium; and directly recovering the expressed gene product from said medium.

The rice α-amylases are encoded by a multigene family which contains at least ten distinct members. To understand how $GA_3$ and sugars regulate α-amylase gene expression in rice, it is important to identify α-amylase cDNA clones representing different α-amylase genes. These clones, in turn, would be used to isolate their corresponding genomic clones.

In this invention, four of the α-amylase cDNA clones showing different restriction patterns were chosen for subcloning into the plasmid vector pBluescript (Invitrogen, San diego, Calif.). The resultant clones were designated as αAmy6-C (Oryza sativa α-amylase cDNA), αAmy7-C, αAmy8-C and αAmy10-C with insert sizes of 0.6, 1.0, 1.4 and 1.5 kb, respectively.

The 3' end regions of these cDNA clones were further subcloned and sequenced. The sequenced 3' regions of αAmy6-C, αAmy7-C and αAmy8-C are found identical to those of the reported rice α-amylase genes RAmy3B (Sutliff et al., 1991), RAmy1A (Huang et al., 1990a), and RAmy3E (Huang et al., 1990b), respectively. The genomic DNA corresponding to αAmy10-C has not yet been reported.

The expression pattern of these four α-amylase genes in cultured suspension cells of rice was determined with the use of the constructed gene-specific probes. Expression of αAmy7-C and αAmy8-C was induced by sugar depletion 6- and 37-fold, respectively, at day 12 and continued to increase at day 14. Expression of αAmy10-C was induced later with a 5-fold increase at day 14. Expression of αAmy6-C also increased 4-fold at day 12, however, it decreased to basal level at day 14. Expression of another α-amylase gene, αAmy3-C, was increased 5-fold after sugar starvation (S. M. Yu, unpublished result).

Therefore, among the five α-amylase genes examined so far, αAmy8-C is the most abundantly expressed gene after sugar depletion. In addition, it is worthwhile noting that αAmy8-C is one of the major genes whose transcripts upon inducement by sugar depletion constitute the 40-fold increase of total amylase transcripts as detected with probe of OSamy-C. The results show that expression of the four α-amylase genes in response to carbohydrate starvation in the cultured cells is temporally and quantitatively regulated.

Consequently, an expression vector containing the promoter region of the rice α-amylase gene (αAmy8) was constructed in order to express β-glucuronidase (GUS) in transformed rice cells. A hygromycin resistance gene hph placed downstream of the CaMV 35S RNA promoter is used as a selectable marker.

Different transformation methods, such as electroporation of protoplasts or intact cells, particle bombardment, micro-injection method, ultrasonic method, polyethylene glycol-mediated protoplast transformation, poly-L ornithine method, calcium phosphate method (Hain, R. et al (1985), Mol. Gen. Genet., 199: 161–168), and Agrobacterium-mediated transformation system can be applied to deliver the plasmid DNA into rice cells. GUS expression was detected in either bombarded or electroporated cells two days after transfection. The results indicate that the α-amylase promoter-GUS chimeric genes are functional in rice cells.

A reporter gene driven by an α-amylase promoter is further transferred and expressed in a Japonica type of rice (*Oryzae sativa* L. cv. Tainung 62) using the Agrobacterium-mediated gene transfer system. Said system comprises a plasmid containing chimeric genes of β-glucuronidase (GUS) and neomycin phosphotransferase (NPTII). The transformation efficieny of said Agrobacterium was improved by co-incubation with potato suspension culture (PSC). The GUS and and NPTII genes, which are under the control of promoters of a rice α-amylase gene (αAmy8) and Agrobacterium nopaline synthase gene (NOS), respectively, were both expressed in transgenic calli and plants. The experimental data demonstrate the successful gene transfer and sexual inheritance of the chimeric genes made in accordance with this invention.

The genetic modification of crops for agricultural, medical and industrial purposes has the potential to yield new processes and products. Production of commerical products by transgenic plants has several advantages over that by the traditional fermentor-based bioreactor. Production of recombinant proteins by transgenic plants also offers a variety of new possibilties for basic research in plant biology as well as for large-scale production of proteins for use in pharmaceutics and industry. The capacity and flexibility of agricultural production suggest that recombinant proteins derived from transgenic plants may be significantly less expensive than recombinant proteins from any other source. For example, if the transgenic plant is capable of expressing an animal vaccine, they may be directely fed to the livestock; if the transgenic plant, e.g. sugar cane, is capable of expressing a recombinant protein, the plant body may be they may be squeezed out for the extraction of such recombinat protein. This aspect becomes increasingly important in cases where large amounts of protein need to be produced. Examples of expression of valuable proteins in plants now includes relatively small peptides (Krebbers and Vandekerckhove, 1990; Vandekerckhove et al., 1989), antibodies (Firek et al., 1993; Hiatt et al., 1989; DÜring et al., 1993), α-amylase (Pen et al., 1992), phytase (Pen et al., 1993), and human serum albumin (Sijmons 1990).

To be of practical application, levels of the foreign protein must accumulate to significant levels in the host plant (e.g. to about 1–10% of the total cellular protein) (Wandelt et al., 1992). However, the yields of foreign proteins produced in the aforementioned reports were lower than 1%.

According to this invention, a protein expression system is developed in which the foreign protein gene will be linked downstream of the α-amylase gene promoter and signal sequence and expressed throughout the whole plant or in the germinating seed of transgenic rice. It is found that expression of the α-Amy8/GUS chimeric protein in transgenic rice is high and in all the plant tissues. It is thus intended to explore the potential of rice plant for producing commercially interesting proteins, e.g. the hepatitis B virus surface antigen S2 and the human interleukin-2.

It has also been found that the α-amylase genes are highly expressed in germinating rice seeds; as such, foreign genes expressed under the control of α-amylase promoter should be packed and enriched in the rice seeds during germination. Such enzyme-enriched seeds can then be directly applied in industrial processes. The use of transgenic enzyme-containing seeds will be most compatible with those processes where plant material is currently employed, as in the case of brewing of cereal plant seeds for alcohol production.

Conventionally, alcoholic fermentation requires a large amount of heat since the starch must first be cooked prior to digestion. The glucoamylase preparation can digest raw starch without prior cooking and so saves energy (Seinosuke Ueda, TIBS March 1981 pp. 89–90).

Glucoamylases (EC 3.2.1.3) hydrolyze α(1,4) and α(1,6)-glycosidic linkages from the nonreducing ends of starch and related malto-oligosaccharides to release glucose. Glucoamylases are important industrially especially in the production of saké (a traditional alcoholic beverage in Japan) and miso (a Japanese seasoning). They are also used commercially to produce glucose from starch.

Glucoamylases have been isolated from the culture fluids of a variety of fungi and yeasts, including Aspergillus and Rhizopus, and their properties and biological significance have been studied. Generally, fungal glucoamylases are known to exist in multiple forms varying in size. The fungus Rhizopus produces large amounts of glucoamylase, which has extremely strong hydrolyzing activity toward raw starch. Transgenic rice seed which can produce glucoamylase will be useful in industrial alcohol production, because it can directly convert the endosperm starch into ethanol. The gene coding for Rhizopus glucoamylase has been cloned and sequenced (Ashikari et al., Agric. Biol. Chem., 50 (4), 957–964, 1986). In this invention, the Rhizopus glucoamylase gene is cloned and to be expressed under the control of α-amylase promoter in transgenic cereal (rice) seeds, so as to shorten the period necessary for the brewing of said cereal (rice) seeds. This approach may lead to a new technology for the production of industrial glucose and ethanol from agricultural sources, e.g. cereal plants seeds including wheat, oat, barley, corn, etc.

Features and advantages of the present invention will become apparent in the following detailed description with references to the accompanying drawings, in which:

BRIEF DESCRIPTION OF THE DRAWINGS

The patent or application file contains at least one drawing executed in color. Copies of this patent or patent application publication with color drawing(s) will be provided by the Patent and Trademark Office upon request and payment of the necessary fee.

FIGS. 1A and 1B show nucleotide sequences of the 3' regions of the rice α-amylase cDNA clones αAmy6-C (SEQ ID NO: 1), αAmy7-C (SEQ ID NO: 3), αAmy8-C (SEQ ID NO: 5), and αAmy10-C (SEQ ID NO: 7).

FIGS. 5A, 5B and 5C show the binding of aleurone protein extract to the 5' specific DNA fragments (SEQ ID NOS: 13–15) of a rice α-amylase gene.

FIGS. 21A and 21B show the nucleotide sequences of the 3' regions of five rice α-amylase cDNA clones αAmy6-C (SEQ ID NO: 1), αAmy7-C (SEQ ID NO: 3), αAmy8-C (SEQ ID NO: 5), αAmy10-C (SEQ ID NO: 7), and αAmy3-C (SEQ ID NO: 8). DNA sequencing was preformed with the dideoxy chain-termination technique. The nucleotide sequence analysis and comparisons were carried out using programs from the Sequence Analysis Software Package of the Genetics computer Group, University of Wisconsin, Version 5.0, June 1987. Sequences are aligned, and gaps (dash lines) are introduced to maximize sequence identity. Identical nucleotides among the five clones are indicated by a star (*). The translation stop codons and polyadenylation signals are marked by double- and single-underlines, respectively. The 5' boundaries of the gene-specific regions are indicated by arrowheads and the restriction enzymes used for DNA truncation are indicated below their corresponding sites. The nucleotide sequence is numbered from the first nucleotide of the sequenced regions.

FIG. 22A: RNA gel blot analysis. FIG. 22B: Levels of mRNA in FIG. 22A were quantified densitometrically and normalized to the actin mRNA level for each time point.

FIG. 23A: RNA gel blot analysis. FIG. 23B: Levels of mRNA in FIG. 23A were quantified densitometrically.

FIGS. 30A and 30B respectively show the construction of plasmids R4T-1 and pYE8-C3. A glucoamylase cDNA excised from pBR322 was subcloned into the yeast expression vector pYE8 and expressed under the control of GAP promoter (FIG. 30A). A cDNA of a rice α-amylase gene, αAmy3, was also subcloned into pYE8 and the derived plasmid was designated as pYE8-C3.

FIGS. 32A and 32B respectively show the construction of the protein expression cassette pA8H(2)-A and the plasmid pGA-2 formed by inserting the glucoamylase (GA) gene into the protein expression cassette pA8H(2)-A.

DETAILED DESCRIPTION OF THE INVENTION

Figure 2:
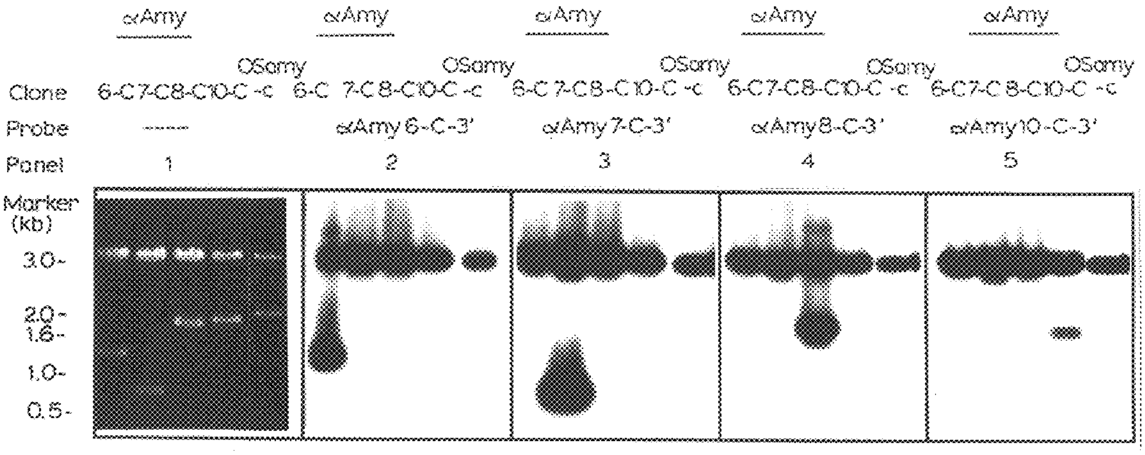
FIG. 2 shows the Southern blot analysis demonstrating specificity of the α-amylase gene-specific probes.

This invention relates to the gene expression regulation of α-amylase promoter, more specifically rice α-amylase promoter, in plant cells and the application thereof.

Alpha-amylases are major amylolytic enzymes for the hydrolysis of stored starch in the endosperm during germination of cereal grains. Previously, we have shown that the expression of α-amylase genes in rice is under two different modes of regulation: I) hormonal regulation in germinating seeds, and II) metabolic repression in cultured cells by available carbohydrate nutrients (Yu, S. M., et al (1991), J. Biol. Chem., 26:21131–21137). Our previous observations suggested a potentially important control mechanism of carbohydrate metabolism in higher plants, which might account for the repression of α-amylase gene expression in the embryo of germinating rice seeds (Karrer, E. E., et al (1991), Plant Mol. Biol., 16: 797–805).

Thus, to understand the molecular mechanisms which regulate the expression of α-amylase genes in rice, we have used transgenic rice carrying a reporter gene under the control of an α-amylase promoter for fuctional analysis of regulatory element in the α-amylase genes.

To do this, four α-amylase cDNA clones were isolated from a cDNA library derived from poly(A)$^+$RNA of giberellic acid ($GA_3$)-treated rice aleurone layers. Nucleotide sequence analysis indicates that the four cDNAs were derived from different α-amylase genes. Expression of the individual α-amylase gene in germinating seeds and suspension-cultured cells of rice was studied using gene-specific probes. Thereafter, a fifth α-amylase cDNA clone αAmy3 is obtained and compared with the foregoing four α-amylase cDNA clones in terms of gene expression and nucleotide sequence.

In germinating seeds, expression of the α-amylase genes is positively regulated by $GA_3$ in a temporally coordinated but quantitatively distinct manner. In cultured suspension cells, in contrast, expression of the α-amylase genes is negatively and differentially regulated by sugars present in medium. In addition, one strong and one weak carbohydrate-starvation responsive α-amylase genes are identified.

The interactions between the promoter region (HS501) of a rice α-amlylase gene and $GA_3$-inducible DNA binding proteins in rice aleurone cells are also studied. DNA mobility-shift assay results showed that aleurone proteins interact with two specific DNA fragments within HS501. One fragment, located between nucleotide residues −131 and −170, contains two imperfect directly-repeated pyrimidine boxes and a putative gibberellin response element. The other fragment, located between residues −92 to −130, contains a putative enhancer sequence. The interactions between aleurone proteins and these two fragments are sequence specific and $GA_3$ responsive.

We further successfully transferred and expressed a reporter gene driven by an α-amylase promoter in a Japonica type of rice (*Oryzae sativa* L. cv. Tainung 62) using the Agrobacterium-mediated gene transfer system. Immature rice embryos (10–12 days post-anthesis) were infected with Agrobacterium strains carrying a plasmid containing chimeric genes of β-glucuronidase (GUS) and neomycin phosphotransferase (NPTII). Co-incubation of potato suspension culture (PSC) with the Agrobacterium inoculum significantly improved the transformation efficiency of rice.

The GUS and NPTII genes, which are under the control of promotors of a rice α-amylase gene (αAmy8) and Agrobacterium nopaline synthase gene (NOS), respectively, were both expressed in transgenic calli and plants. Integration of foreign genes into the genomes of transgenic plants was confirmed by Southern blot analysis. Histochemical localization of GUS activity in one transgenic plant (T1) revealed that the rice α-amylase promoter functions in all cell types of the mature leaves, stems, sheaths and roots, but not in the very young leaves. This transgenic plant grew more slowly and produced less seeds than the wild type plant. GUS activity was also detected in calli derived from progeny (R1) of this plant. The GUS gene fragment was amplified by polymerase chain reaction using DNA isolated from the R1 progeny of the same transgenic plant. These data demonstrate successful gene transfer and sexual inheritance of the chimeric genes.

Accordingly, in the present invention we describe the transformation of rice with Agrobacterium and the successful expression of an α-amylase promoter-driven reporter gene in a regenerated plant and R1 progeny of a japonica type transgenic rice. To our knowledge, this is the first report to show Agrobacterium-mediated transformation of rice and to demonstrate inheritance of the transferred DNA by the progeny of the transgenic rice. It should therefore be comprehended that the chosen foreign gene (GUS) used in the present invention plays two roles in the present gene expression system: as a foreign gene to be inserted into the present gene expression system and as a reporting gene for indicating the successful transformation of said gene expression system.

EXAMPLE I

Methods:

a) Conditions for preparation of aleurone RNA, construction of the cDNA library, and screening for α-amylase cDNA clones were performed as follows:

Rice (*Oryzae sativa* cv. Labelle) seeds were surface sterilized in 2.5% sodium hypochloride for 20 min., washed extensively with sterile distilled $H_2O$, and incubated in sterile 10 μM $GA_3$/20 mM $CaCl_2$/20 mM sodium succinate for different lengths of time. The germinating embryos were cut off and the aleurone layers were peeled off the endosperm. The collected aleurone layers were immediately frozen in liquid $N_2$ and stored at −70° C. until use. Total RNA was isolated from the frozen aleurone layers according to the method of Belanger, F. C., et al (Proc. Natl. Acad. Sci. USA, 83: 1354–1358, 1986). Poly (A) $^+$RNA was purified with HYBOND-mAP affinity paper (Amersham). One microgram of poly (A) +RNA was used to construct a cDNA library in lamda-gt11 using Amersham's cDNA synthesis and cloning systems. The cDNA library consisted of approximately $2\times10^7$ independent recombinant clones. Approximately $2\times10^4$ plaques were screened using the $^{32}$P-labeled 1.5 kb fragment of the rice genomic clone, OSamy-C (J. K. Kim and R. Wu (1992), Plant Mol. Biol., 18: 399–402). The cDNA clones in lamda-gt11 were cleaved with EcoR I and subcloned into EcoR I site of pBluescript and maintained in *E. coil* strain XL1-B (Stratagene).

DNA sequencing was performed with the dideoxy nucleotide chain termination technique. Referring to FIGS. 1A and 1B, nucleotide sequence analysis and comparisons were carried out using programs from the Sequence Analysis Software Package of the Genetics Computer Group, University of Wisconsin, Version 5.0, June 1987. Nucleotide sequences are aligned and gaps (dash lines) are introduced to maximize sequence similarity. The homologous sequences among the four clones are indicated by asterisks (*). The translation stop codons and polyadenylation signals are underlined. The 5' boundaries of the gene-specific regions are indicated by arrows and the restriction enzymes used for DNA truncation are indicated below their corresponding sites. The nucleotide sequence is numbered from the first base of the sequenced regions. Accession number for αAmy10-C in GeneBank, EMBL, and DDBJ is M81143.

b) Conditions for preparation of $^{32}$P-labeled gene-specific probes were performed as follows:

The four α-amylase cDNAs were truncated at the 5' ends of the gene-specific regions using restriction enzymes indicated in FIGS. 1A and 1B. In vitro transcription of the four truncated cDNAs with the T3 RNA polymerase yields antisense-strand transcripts of sizes 210, 112, 119, and 50 nucleotides, representing αAmy6-C-3', αAmy7-C-3', αAmy8-C-3' and αAmy10-C-3', respectively. $^{32}$P-UTP (Amersham, SP-6 tested) was used to label the probe.

Figure 3:
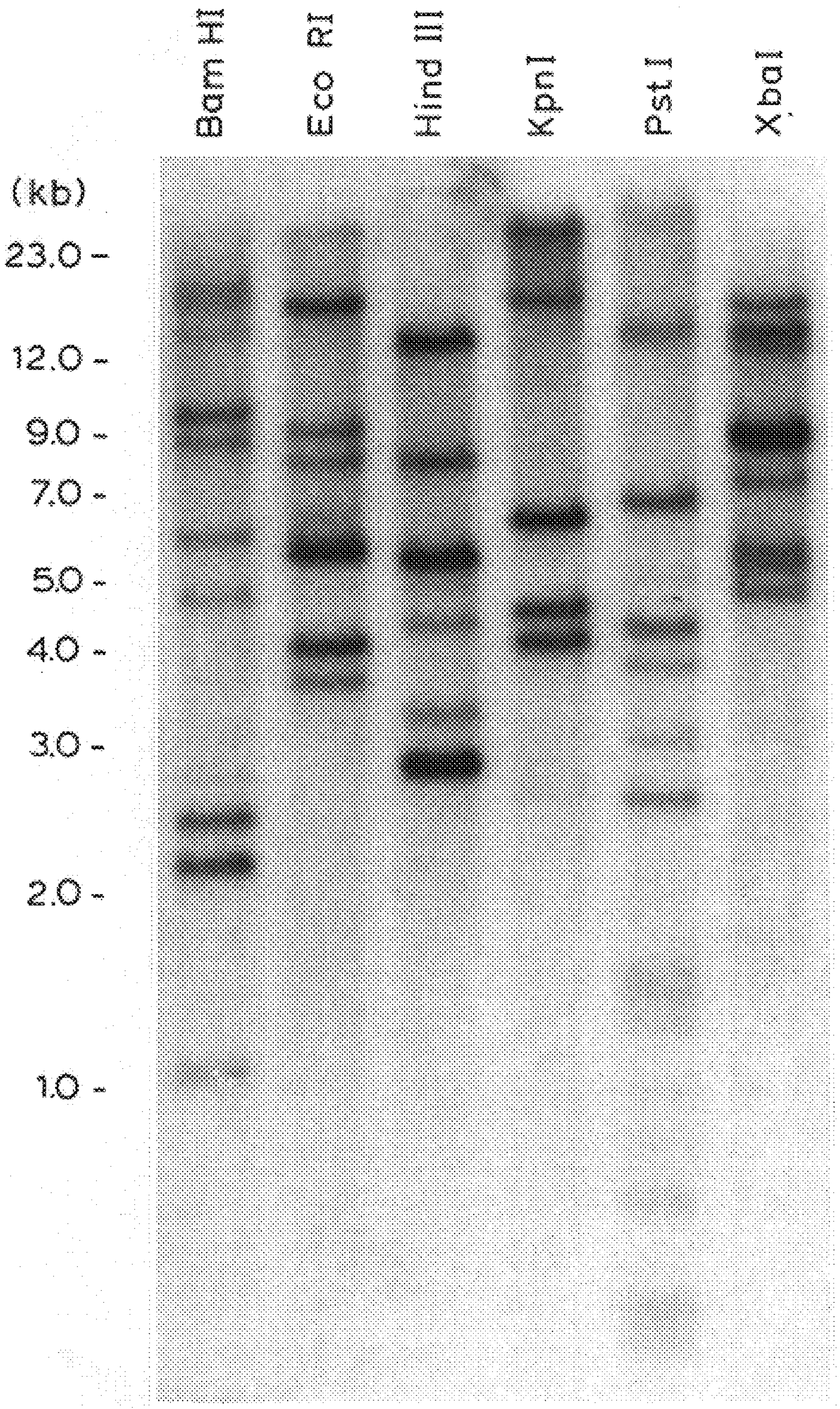
FIG. 3 shows the southern blot analysis of α-amylase genes in rice genome.

Southern blot analysis which demonstrates the specificity of the α-amylase gene-specific probes was carried out as shown in FIG. 2, in which: Panel 1: the α-amylase cDNA was digested with EcoR I and OSamy-c was digested with BamH I and EcoR I, then electrophoresised on 1% agarose gel, and stained with ethidium bromide. Panels 2–5: four replicates of the same gel as shown in Panel 1 were blotted to GeneScreen membranes, a hybridized with the $^{32}$P-labeled gene-specific probes at 42° C. for 12 hr. After hybridization, the membranes were washed in 0.1×SSC and 0.1% SDS at 55° C. for 40 min. The vectors were also hybridized because the antisense RNA probes contained a sketch of 62 bp sequences of the multiple cloning sites of pBluescript between the T3 promoter and EcoR I site where the cDNAs were inserted. Molecular weight markers are shown on the left.

c) Southern blot analysis of α-amylase genes in rice genome was carried out as follows:

With referrence to FIG. 3, total rice genomic DNA was isolated from two month old greenhouse-grown plants. Rice leaves were ground in liquid $N_2$ to fine powder, extracted with urea extraction buffer [42 g/ml urea, 5 M NaCl, 1 M Tris-Cl (pH 8.0), 0.5 M EDTA (pH 8.0), and 20% sarkosine] and equal volumes of phenol-chloroform at room temperature for 15 min. After centrifugation, ammonium acetate (pH 5.2) and isopropanol were added to the supernatant. DNA precipitated immediately and was spooled with a glass hook, rinsed in 75% and 100% ethanol, and air-dried. DNA was resuspended in TE buffer and stored at 4° C. Ten micrograms of genomic DNA was digested with six restriction enzymes, fractionated by electrophoresis using 0.8% agarose gels, and transferred to GeneScreen membrane (DuPont). The membrane was probed with the $^{32}$P-labeled 1.5 kb α-amylase cDNA insert of αAmy10-C. Molecular weight markers are shown on the left.

d) Accumulation of α-amylase mRNA in germinating seeds and suspension cultured cells of rice.

Figure 4A:
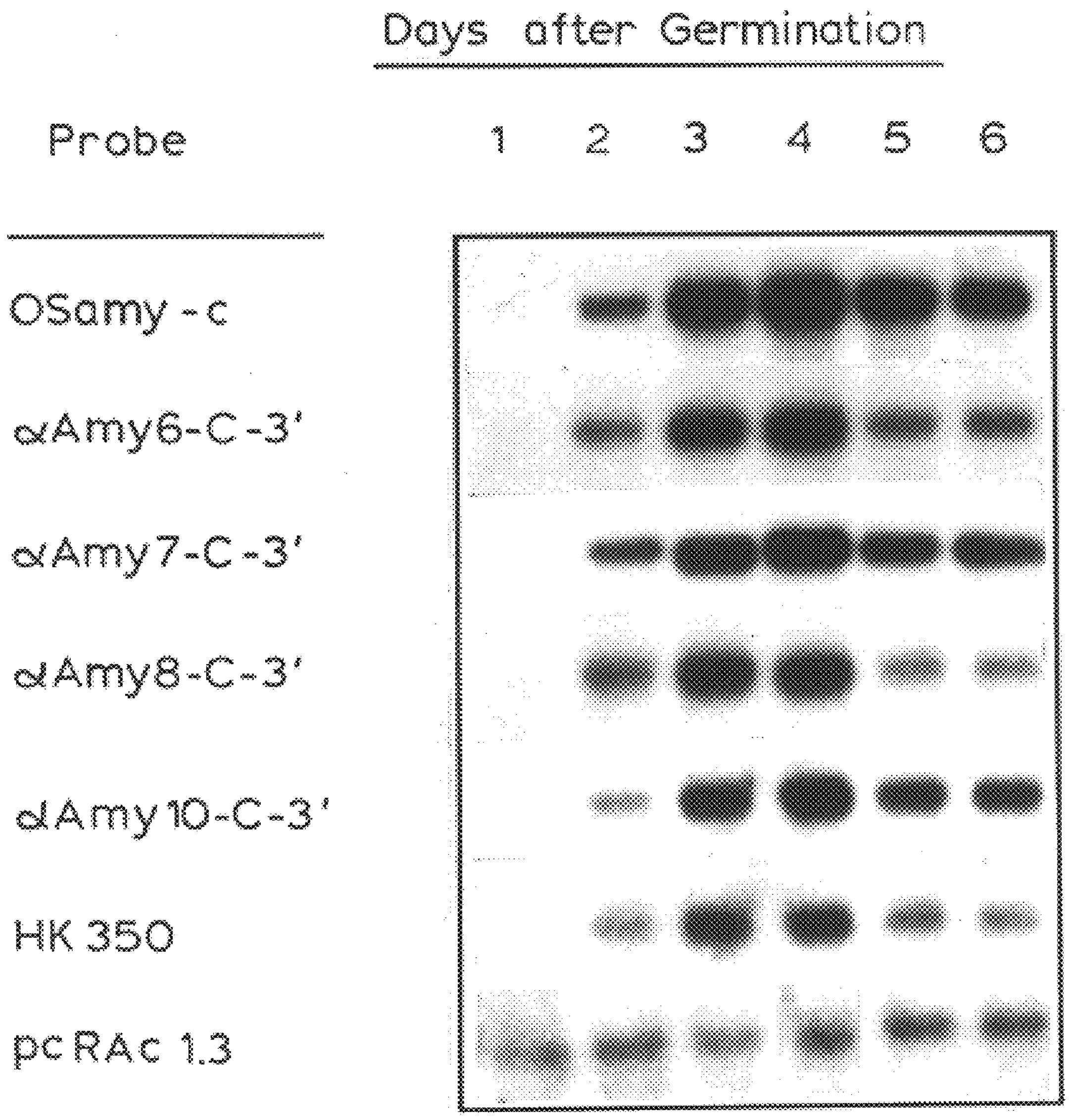
FIGS. 4A and 4B show the accumulation of α-amylase mRNA in germinating seeds and suspension cultured cells of rice. (A) Time course of accumulation of α-amylase mRNA in $GA_3$-treated aleurone cells of rice. (B) Relative mRNA levels of the α-amylase genes in the suspension cultured cells of rice during later growth stage.
Figure 4B:
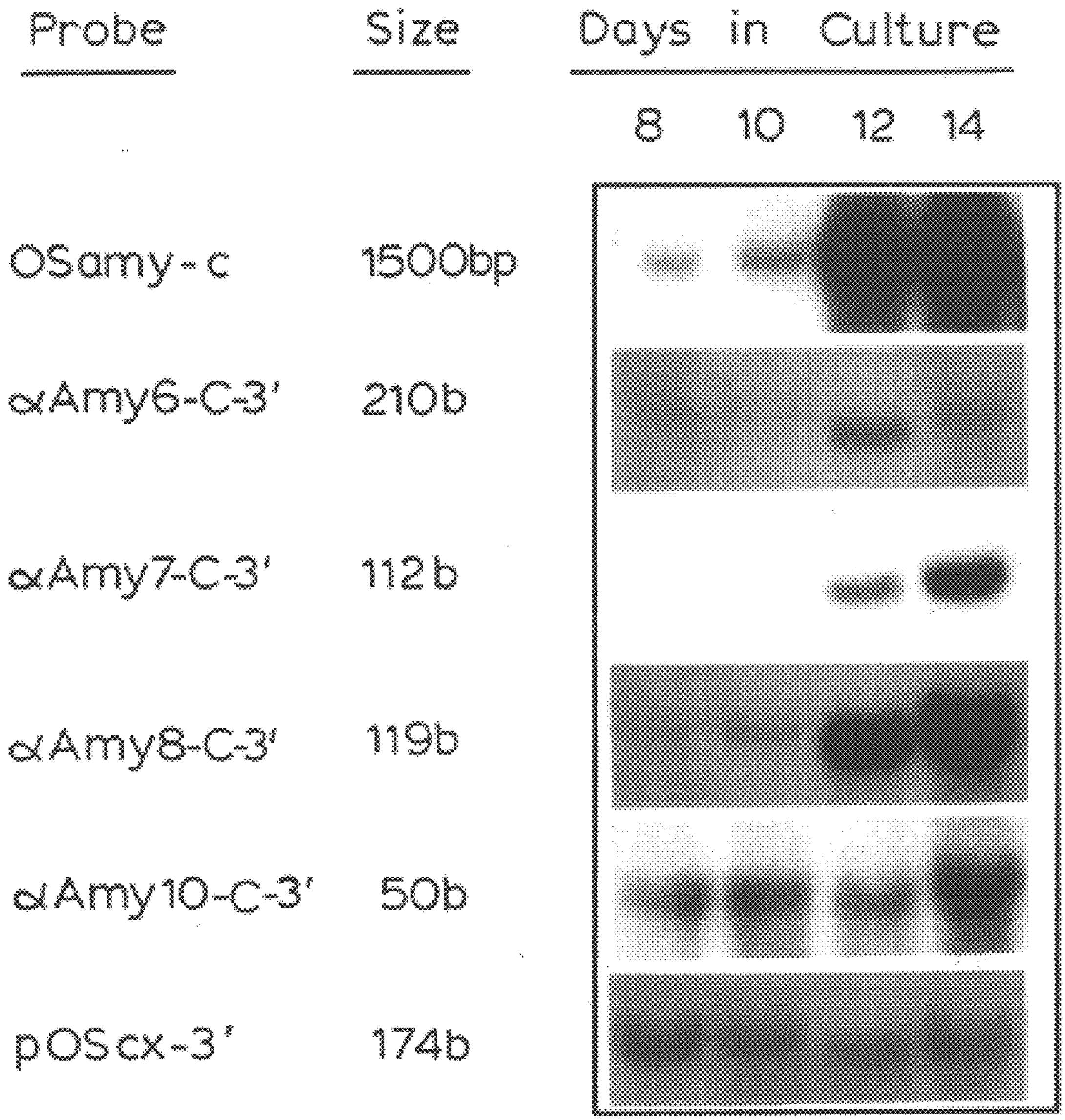

With referrence to FIGS. 4A and 4B, rice seeds were germinated in 10 μM $GA_3$ for different lengths of time. The germinating embryos were cut off and total aleurone RNA was purified from the embryoless seeds according to the method of Belanger, F. C., et al. (Proc. Natl. Acad. Sci. USA, 83: 1354–1358, 1986). Rice suspension cells were cultured as described previously (Yu, S. M., et al (1991), J. Biol. Chem., 266: 21131–21137). RNA was purified from cells grown in the sucrose-containing medium for 8, 10, 12 and 14 days. Five micrograms of total RNA was applied to each lane. The RNA blot analysis was performed according to the method of Thomas P. S. (Methods Enzymol., 100: 255–266, 1983). The plasmid pOSamy-c containing an entire α-amylase coding region in pBluescript was originally subcloned from a rice genomic clone OSamy-c (J. K. Kim and R. Wu (1992), Plant Mol. Biol., 18: 399–402): The 1.5 kb α-amylase DNA insert of OSamy-c was excised from the plasmid vector by restriction enzymes BamH I and EcoR I, gel-purified as described by Maniatis et al. (*Molecular Cloning: A Laboratory Mannual,* pressed by Cold Spring Harbor Laboratory, 1982), and labeled with [α-$_{32}$P]dCTP using the random primer method (A. P. Feinberg and B. Vogelstein (1983), Anal. Biochem., 132: 6–13). The gene-specific probes corresponding to each of the four rice α-amylase cDNAs were prepared and labeled as described above with referrence to FIGS. 1A and 1B and FIG. 2. Size of mRNA detected by all of of the probes is 1.6 kb.

e) Binding of aleurone protein extract to the 5' specific DNA fragments of a rice α-amylase gene, in which methods for preparation of aleurone layer extract and DNA mobility-shift (gel retardation) assay were as described previously (Yu., S. M., et al (1990), supra).

The results were shown in FIG. 5, in which:

(A) Fragments A, B and C were three consecutive 40 bp synthetic DNA fragments at the 5' end of HS501. Filled box indicates the position of two imperfect directly-repeated pyrimidine boxes and a GARE-like element. Open box indicates the position of the 11 bp putative enhancer like element.

(B) Interaction of aleurone proteins to fragments A, B, and C. The symbols (+) and (−) indicate reactions with or without protein extracts respectively. B1, B2, and B3 indicate positions of the three protein-DNA complexes. F indicates position of the free DNA probe.

(C) The nucleotide sequences of fragments A, B, and C. Numbers indicate positions of the three fragments relative to the transcription start site. Underlines indicate positions of the pyrimidine boxes. Asterisks (*) indicate position of the GARE-like element. Dash line indicates position of the enhancer-like element.

Results:

(A) Cloning and characterization of the rice cDNA

The rice cDNA library was screened with the α-amylase gene OSamy-c (J. K. Kim and R. Wu (1992), Plant Mol. Biol., 18: 399–402) as the probe. Four of the α-amylase cDNA clones showing different restriction patterns were chosen for subcloning into the plasmid vector pBluescript. The resultant clones were designated as αAmy6-C (*Oryzae sativa* α-amylase cDNA), αAmy7-C, αAmy8-C and αAmy10-C with insert sizes of 0.6, 1.0, 1.4, and 1.5 Kb, respectively. The 3' end regions of these cDNA clones were further subcloned and sequenced (FIGS. 1A and 1B). The sequenced 3' regions of αAmy6-C, αAmy7-C and αAmy8-C are found identical to those of the reported rice α-amylase genes RAmy3B (Sutliff, T. D., et al (1991), Plant Mol. Biol., 16: 579–591), RAmy1A (Huang, N., et al (1990a) Plant Mol. Biol., 14: 655–668), and RAmy3E (Huang, N., et al (1990b), Nucl. Acids Res., 18: 7007–7014), respectively. The genomic DNA corresponding to αAmy10-C has not yet been reported. The DNA and deduced amino acid sequence of genomic rice α-amylase genes corresponding to αAmy6-C, αAmy7-C, αAmy8-C and αAmy10-C are respectively set out in detail in SEQ. ID. NO's.: 1 and 2, 3 and 4, and 5 and 6, respectively. The DNA sequence of αAmy10-C is set out in SEQ. ID. NO:7, in which αAmy10-C was sequenced once only.

(B) Construction of the rice α-amylase gene-specific probes

Comparison of nucleotide sequences of the 3' untranslated regions shows very low identity (23–27%) among the four α-amylase cDNA clones (FIG. 1), except αAmy7-C and αAmy10-C which showed 69% identity. Restriction sites were selected for separation of the nonhomologous (gene-specific) regions from the homologous regions of these four cDNA clones and for the preparation of antisense RNA probes. The restriction enzymes used and the nucleotide sequences of the gene-specific regions are shown in FIGS. 1A–1B.

The gene-specific sequences corresponding to each of the four cDNAs are designated as αAmy6-C-3', αAmy7-C-3', αAmy8-C-3' and αAmy10-C-3'. Appropriate regions were selected for αAmy10-C-3' in which there is very low homology with αAmy7-C-3'. Cross-hybridizations were then performed to determine the gene-specificity and the results showed that each probe only hybridized to their respective parental cDNA (FIG. 2). None of these gene-specific probes hybridized to OSamy-c, which was originally used as the probe to screen the cDNA library. The results demonstrated that the four gene-specific probes are able to discriminate different α-amylase genes.

(C) The rice α-amylases are encoded by a gene family

Identification of the four distinct α-amylase cDNAs indicates that the rice α-amylases are encoded by a gene family. To determine the number of α-amylase genes in rice, total genomic DNA isolated from rice leaves was digested with various restriction enzymes and probed with the entire αAmy10-C sequences at low stringency (FIG. 3). Eight or nine restriction fragments were observed when total DNA was digested with EcoR I. The result generally is in agreement with the reported restriction maps of the rice α-amylase genes (Huang, N., et al (1990a), supra). Since two α-amylase genes were shown to be linked on one EcoR I fragment (Huang, N., et al (1990b), supra), the entire rice genome is estimated to contain at least 10 genes. Parallel genomic DNA blots were also hybridized with the four rice α-amylase gene-specific probes. Each gene-specific probe hybridized specifically to only one restriction fragment (data not shown) further confirming that each probe is derived from one α-amylase gene.

(D) Expression of α-amylase genes in rice germinating seeds.

To determine whether the expression of different members of a α-amylase gene family are regulated in a same manner during seed germination, gene-specific probes were used to study the expression of individual α-amylase genes in $GA_3$-treated germinating seeds. The accumulation of α-amylase mRNA in aleurones as a function of time after $GA_3$ addition was determined by RNA blot analysis (FIG. 4A). Probe made from pOSamy-c containing the coding region of a rice α-amylase gene was expected to hybridize to mRNAs of most, if not all, α-amylase genes. The α-amylase mRNA was barely detectable at day 1, rapidly accumulated and reached their maximal levels at day 4, then rapidly turned over between day 4 and day 5. A rice actin cDNA clone, pcRAc1.3 (McElroy, D., et al (1990), Plant Mol. Biol., 14: 163–171), whose expression was not affected by $GA_3$ was used as an internal control.

Level of mRNA showm in FIG. 4A was quantified by measuring the signal intensity of the autoradiogram using a densitometer. The relative mRNA accumulation of each α-amylase gene at each day was determined by comparison of mRNA levels with their peak level at day 4 (Table 1). The mRNA of each α-amylase gene accumulated at a similar rate, except that of αAmy8-C, which almost reached peak level at day 3. However, the mRNAs of αAmy6-C and αAmy8-C were turned over at higher (2-fold) rates than those of αAmy7-C and αAmy10-C. The mRNA levels of αAmy7-C and αAmy10-C were reduced to ½, in contrast, those of αAmy6-C and αAmy8-C were reduced to ¼, of their highest levels at day 5. Afterward all the mRNA levels were reduced at similar low rates. The results show that expression of the four α-amylase geens in germinating seeds are temporally coordinated but quantitively distinct.

(E) Expression of α-amylase genes in cultured suspension cells of rice.

Previously, we have shown that the expression of α-amylase genes in cultured suspension cells of rice is induced by the deprivation of carbohydrate nutrient (Yu, S. M., et al (1991), supra). In that report, OSamy-c was used as a probe to study the expression of the entire α-amylase gene family in suspension-cultured cells. Here, gene-specific probes were used to determine the expression pattern of different α-amylase genes. We have shown that the sugars (analyzed by the anthrone reaction) in the sucrose-containing medium were depleted to almost undetectable levels at day 12. A concomitant increase in α-amylase mRNA was observed at day 12 (Yu, S. M., et al (1991), supra). Therefore, RNA's purified from cells grown in the surcrose-containing medium for 8, 10, 12, and 14 days were used for the RNA blot analysis (FIG. 4B). A cDNA clone, pOScx, which was randomly chosen from the same cDNA library, and whose expression was not affected by sugar depletion, was used as an internal control.

Level of mRNA shown in FIG. 4B was also quantified and the relative mRNA accumulation of each α-amylase gene at each day was determined by comparison of mRNA levels with their basal level at day 8 (Table 2). Expression of αAmy7-C and αAmy8-C was induced 6- and 37-fold, respectively, at day 12 and continued to increase at day 14. Expression of αAmy10-C was induced later with a 5-fold increase at day 14. Expression of αAmy6-C also increase 4-fold at day 12, however, it decreased to basal level at day 14. Expression of another α-amylase gene, αAmy3-C, was increased 5-fold after sugar starvation (Yu, S. M., unpublished result). Therefore, among the five α-amylase genes examined so far, αAmy8-C is the most abundantly expressed gene after sugar depletion.

In addition, it is worthwhile noting that αAmy8-C is one of the major genes whose transcripts constitute the 40-fold increase of total α-amylase transcripts as detected with probe of OSamy-c. The results show that expression of the four α-amylase genes in response to carbohydrate starvation in the cultured cells is temporally and quantitatively regulated.

(F) Specific regions of the promoter of a rice α-amylase gene interacting with protein factors in the GA-treated aleurone layer.

HS501 is a DNA fragment which is located at the 5' end promoter region of a rice α-amylase gene, OSAmy-b (Ou-Lee, T. M., et al. (1988), supra), and its DNA sequences have been presented (Yu, S. M., et al. (1990), supra). Nucleotide sequence of HS501 was later found identical to that of RAmy3C which encodes a complete rice α-amylase isozyme (Sutliff, T. D., et al. (1991), supra). DNA sequence of HS501 includes 260 nucleotides of the 5' non-coding region, and 270 nucleotides in the first and part of the second exons. HK350 is a 3' end-deleted derivative of HS501 and contains the entire 5' non-coding (260 bp) and the first exon regions (90 bp) of HS501. RNA blot analysis showed that α-amylase mRNA of aleurone cells, detected by probing with HK350, was also increased after $GA_3$ treatment (FIG. 4A).

Figure 5A:
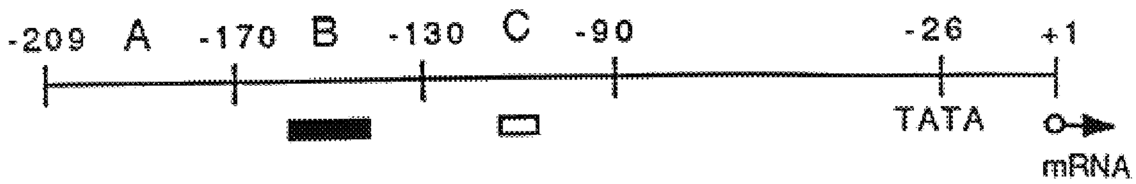
Figure 5B:
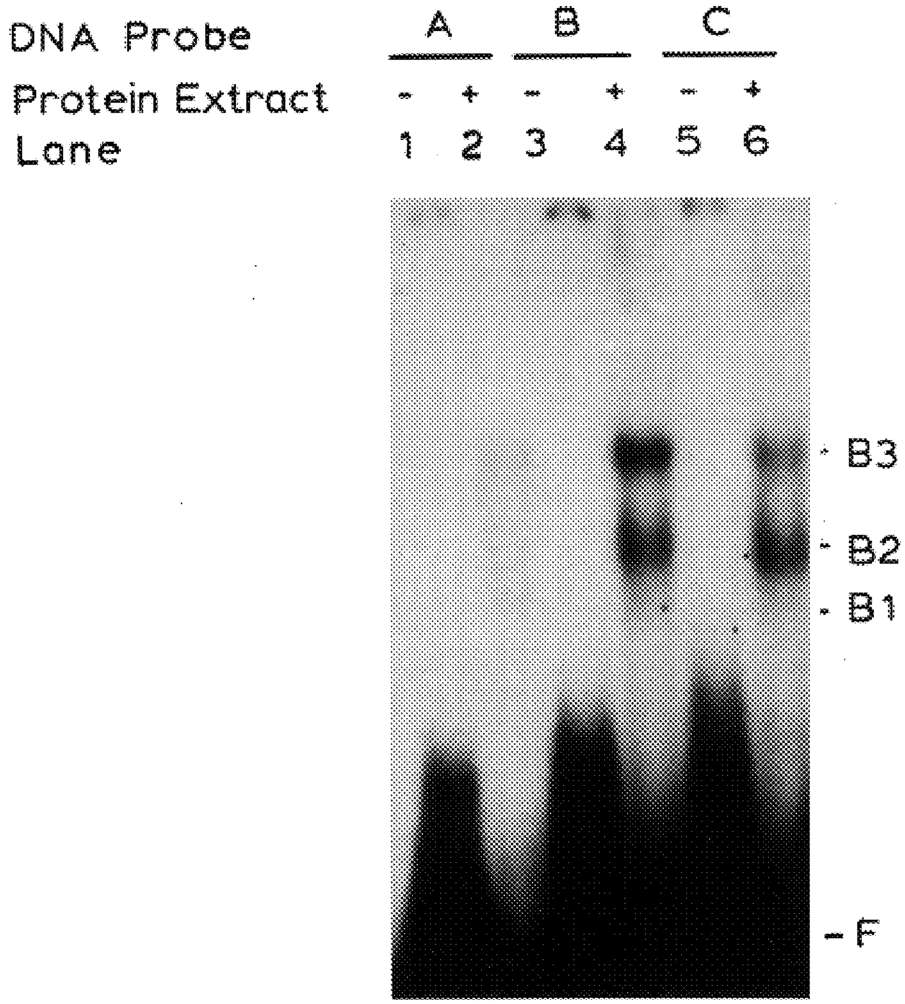

Previously, we have shown that the 5 end of HS501 is important for stable formation of a protein-DNA complex (Ou-Lee, T. M., et al. (1988), supra; Yu, S. M., et al. (1990), supra). To more precisely localize the protein binding sites in HS501, we synthesized three consecutive double-stranded 40 bp oligonucleotides (SEQ ID NOS: 13–15), designated as A, B and C, corresponding to the 5' end of HS501 (FIG. 5A). Proteins were extracted from the aleurone tissues of $GA_3$-treated germinating seeds and interactions between aleurone proteins and the synthetic DNA fragments were detected by the gel retardation assay (FIG. 5B). Interaction of the extract with fragments B and C resulted in the formation of complexes B1, B2 and B3 (FIG. 5B, lanes 4 and 6). Very weak, if any, binding could be detected between the protein extract and fragment A (FIG. 5B, lane 2). Comparison of DNA fragments A, B and C reveals that the three fragments shared some similarity (FIG. 5C). It is not clear whether the weak binding of fragment A to the proteins was due to low affinity or non-specific binding. Nevertheless, the result indicates that there are protein binding sites within fragments B and C.

(G) $GA_3$-dependent and sequence-specific protein factors which bind to HS501.

Figure 6:
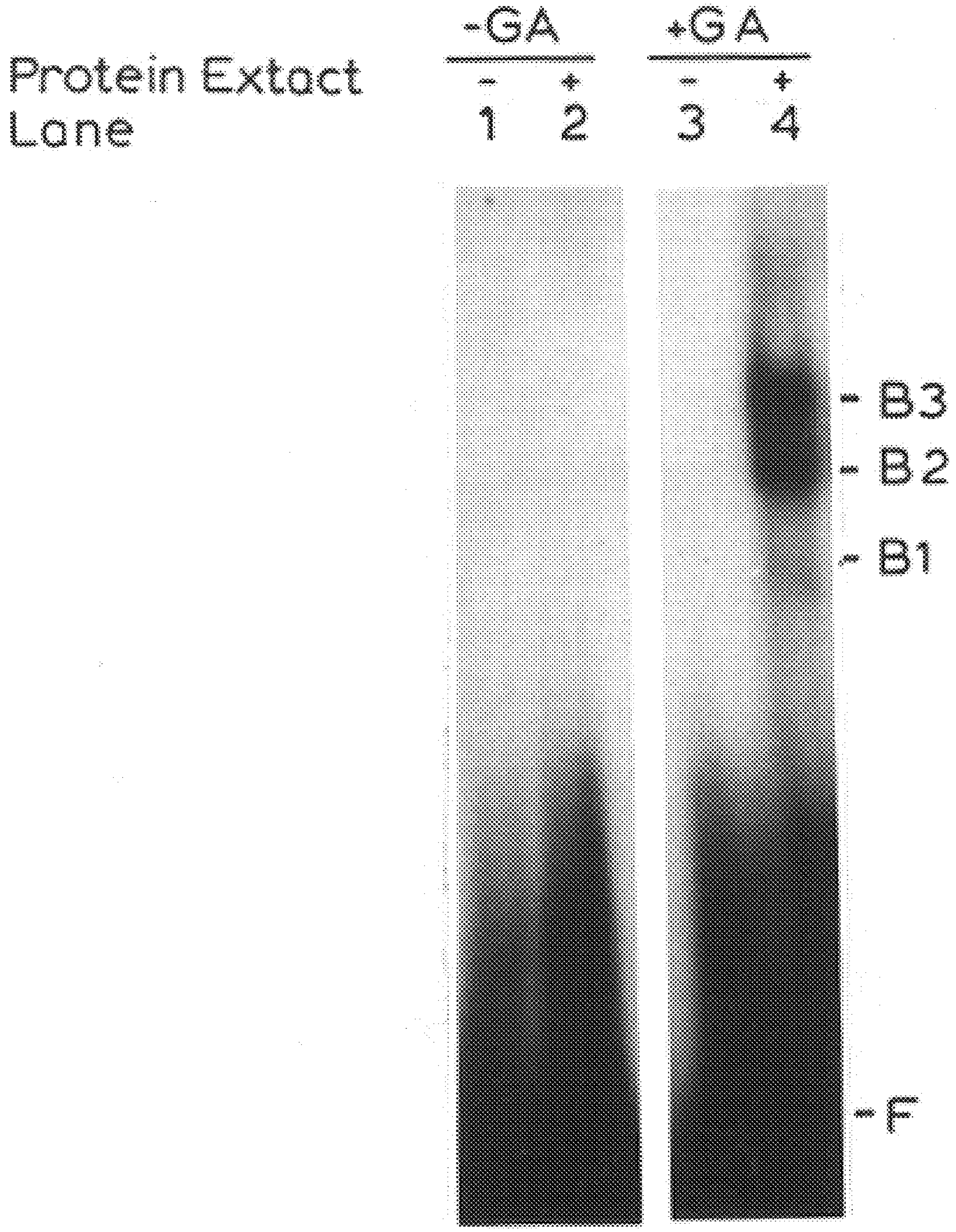
FIG. 6 shows the Binding of the $GA_3$-inducible aleurone proteins to the specific DNA fragment of HS501. +GA and −GA: protein extracts prepared from deembryoed rice seeds after 3 days of imbibition with or without $GA_3$, respectively.

We carried out another protein/DNA binding assay to determine whether or not the DNA-binding protein is $GA_3$-inducible. Proteins were extracted from the aleurone tissues of de-embryoed seeds which had been treated either with or without $GA_3$ for three days. Only the aleurone extract from $GA_3$-treated seeds gave rise to three complexes using fragment B (FIG. 6, lane 4) or C (data not shown). The aleurone extract did not bind to fragment A (data not shown). No DNA/protein interaction was detected between the aleurone extract from seeds untreated with $GA_3$ and fragment B (FIG. 6, lane 2). The results indicate that the aleurone proteins which bind to fragments B and C are $GA_3$ dependent.

Conclusions:

(1) The availability of gene-specific probes corresponding to each of the four α-amylase cDNAs has enabled us to examine the abundance of mRNA encoding specific α-amylase isozymes. Expression of the individual α-amylase gene was found to be coordinately regulated and their mRNAs were accumulated at similar rates and levels in the aleurone layer of germinating seeds of rice. However, differences in the turnover rates of mRNA of different α-amylase genes indicate a possible differential regulation on the expression of different α-amylase genes in germinating seeds. The a:four α-amylase genes expressed in germinating seeds were expressed constitutively at low levels in cultured cells when sugars were still present in medium. Expression of three of the four α-amylase genes were induced after sugars are depleted from the medium, and only αAmy6-C displays a different expression pattern from the other three genes. It is not known whether different α-amylase isozymes perform different functions in the starch hydrolysis in rice, or whether the regulatory machinery is differentially acting on a set of α-amylase genes which have similar structures and/or functions. Further investigations on the regulation and expression of different members of the α-amylase gene family in different tissues, and their structural and functional relationships, should help us to better understand the physiological roles of α-amylases in rice.

(2) $GA_3$ and sugars regulate expression of the same α-amylase genes. Whether the two modes of regulation operate through an identical or different molecular mechanism is not known. As expression of αAmy8-C was $GA_3$ regulated in germinating seeds and is one of the major metabolite-regulated genes in suspension-cultured cells, it would be a good model gene for such studies. Molecular mechanisms underlying the two different modes of regulation and interactions between them will be the focus for further studies.

(3) Aleurone tissues contain proteins that interact with fragments B and C of HS501 only in the presence of $GA_3$. Fragment C contains an 11 bp fragment (GTTGCGTTTCT) (SEQ ID NO: 10) from positions −108 to −118 which is similar to the animal core enhancer

```
[GTGGTTT(T)G]
     AAA
```

(Gillies, S. D., et al., Cell (1983), 33: 717–728; Weiher, H., et al (1983) Science, 219: 629–631). Fragment B contains two pyrimidine boxes

```
(CCTCCTTT)
    T
```

from positions −145 to −152 and positions −157 to −164 which are similar to the consensus sequences (CCTTTTC)
T T found in several α-amylase genes of rice, wheat, barley and other GA-inducible genes such as β-glucanase, carboxypeptidase and aleurain (Huang, N., et al (1990a), supra). Promoter deletion analysis demonstrated that sequences encompassing two of the three pyrimidine boxes in the promoter region of a wheat α-amylase gene, αAmy2/54, are required for high level expression and $GA_3$ regulation of this gene (A. K. Huttly and D. C. Baulcombe (1989), supra). Mutation of the pyrimidine box in the promoter region of a barley α-amylase gene, Amy32b, significantly decrease both the absolute level of expression and the effect of $GA_3$ on expression (Lanahan, M. V., et al (1992), Plant Cell, 4: 203–211). In addition, sequence immediately 3' to the second pyrimidine box in fragment B of HS501, reads TAAATGAG from positions −138 to −145, sharing conservation with the putative GARE element TAACAGAG (Huang, N., et al (1990a), supra; Lanahan, M. V., et al (1992), supra) which is shown to mediate hormonal regulation of the α-amylase gene (Lanahan, M. V., et al (1992), supra; Skriver, K., et al (1991), supra). Whether or not the GA-responsive proteins, the pyrimidine boxes, and the putative GARE element represent the trans- and cis-regulatory elements responsible for GA stimulation of the rice α-amylase genes remain to be determined.

EXAMPLE II

In this experiment, the αAmy8 gene was selected from the foregoing four α-amylase genes for further studying the construction of a chimeric gene containing GUS/NPTII, the expression of which was under the control of the promoter region of said αAmy8 gene, and nopaline synthase gene (NOS), respectively.

A) Materials and Methods

1) Plant Materials

The rice variety used for transformation was *Oryzae sativa* L. cv. Tainung 62. At 10–12 days post-anthesis, seeds were dehulled, sterilized with 1% NaOCl and 1 drop of Tween-20 for 90 min., and washed extensively with sterile distilled water. Immature embryos were excised aseptically in a lamina flow bench. Excised embryos were placed on N6RD medium (Chan, M. T., et al (1992), supra) containing N6 salts (Chu, C. C., et al, Scientia Sinica 18: 659–668, 1975), N6 vitamins, 3% sucrose, 0.8% agarose (w/v), 2 μg/l 2,4-D, and cultured at 25° C. for 16 hours under light (1000 lux). Two days later, the immature embryos were inoculated with Agrobacterium.

2) Bacterial Strain and Plasmid

Figure 7:
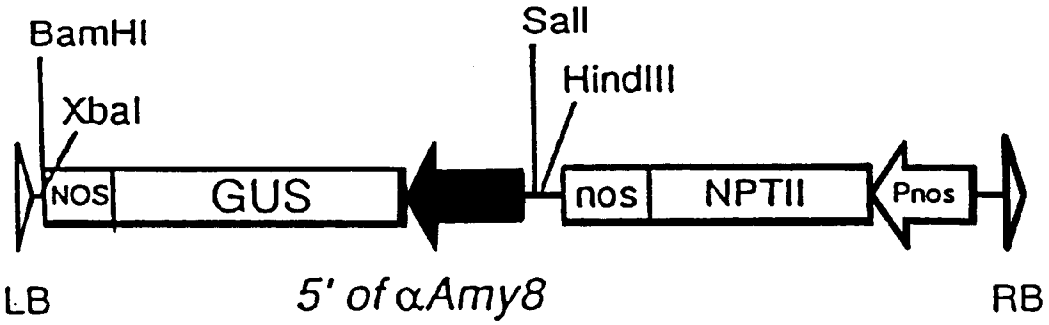
FIG. 7 shows the structure of the binary vector pAG8 containing the αAmy8 (1.2 kb)/GUS chimeric gene. The 1.2 kb 5'-upstream fragment of the α-amylase gene αAmy8 was joined to the coding region of the *E. coli* β-glucuronidase gene (GUS) with the polyadenylation signals of nopaline synthase gene (NOS). This chimeric gene was inserted between the left border and the selectable marker gene of pBIN19. Abbreviations: RB and LB, right- and left-border of T-DNA, respectively; NPTII, neomycin phosphotransferase II gene; Pnos, promoter of NOS gene.

An isolated 1.2 kb fragment, just upstream of the coding region of a rice α-amylase gene αAmy8, was joined to the *E. coli* β-glucuronidase (GUS) (Jefferson, R. A., Plant Mol. Biol. Rptr., 5: 387–405, 1987) with a nopaline synthase (NOS) gene terminator to test the promoter's activity. This chimeric gene [αAmy8 (1.2 kb)/GUS] was inserted between restriction sites Xba I and Sal I of multicloning regions of the binary vector plasmid pBIN19 (Bevan, M. W., Nucl. Acids Res., 12: 8711–8721, 1984) to generate a new plasmid pAG8 (FIG. 7). Plasmid pAG8 was transfected into *Agrobacterium tumefaciens* strain A281 (Hood, E. F., Bio/technology 2: 702–709, 1984) using the freeze-thaw method (Holster, M., et al (1978), Mol. Gen. Genet., 163: 181–187). *Agrobacterium tumefaciens* was grown overnight at 28° C. in YEB medium (Zaenen, J., J. Mo. Biol., 86: 109–127, 1974) containing 100 mg/l kanamycin.

B) Transformation

Twenty-five immature embryos were wounded by sterilized forceps and scalpels and co-cultivated overnight with 25 μl of overnight Agrobacterium culture in a petri dish containing 10 ml of potato suspension culture (PSC), then incubated at 26° C. in the dark for 3 days. For the control, 10 ml of fresh potato suspension culture medium (Chang, H. H., (1991), supra) without addition of potato suspension cells was used. Conditions for potato suspension culture have been described previously (Chang, H. H., (1991), supra).

The infected immature embryos were washed once with potato suspension culture medium containing 500 μg/ml cefotaxime to kill the Agrobacterium and then transferred to N6RF medium containing N6 salts, N6 vitamins, 42.5 μg/ml 4-fluorophenoxyacetic acid (4-FPA), 3% sucrose, 0.8% (w/v) agarose, 40 μg/ml G-418, and 500 μg/ml cefotaxime. The pH of the medium was adjusted to 5.7 before autoclaving. The embryos were cultured at 25° C. for 16 hours under light (2000 lux) and subcultured at weekly intervals.

C) Selection and Regeneration of Transformants

Calli were formed from the cultured embryos 3 weeks after Agrobacterium inoculation. The calli were transferred to N6RFB medium (similar to N6RF but containing 13 μg/ml 4-FPA, 1 μg/ml 6-benzylamino-purine (6-BAP), 40 μg/ml G-418 and 200 mg/ml cefotaxime) for selection of transformants. After selection for 3 weeks, calli were transferred to N6 medium for shoot regeneration and root development. Regenerated plants were eventually transferred to pot soil in the green-house and grown to self-pollination. Segregation of the kanamycin resistant phenotype in the progeny was analysed by germinating the R1 seeds on MS medium containing 300 μg/ml kanamycin.

D) DNA Isolation and Analysis of Gene Incorporation

DNA from transgenic plants was isolated according to the CTAB method (M. G. Murry and W. F. Thompson, Nucl. Acids Res., 8: 4321–4325, 1980). DNA bolt analysis was performed as described by Maniatis et al (*Molecular Cloning: A Laboratory Mannual,* pressed by Cold Spring Harbor Laboratory, 1982). The probe for GUS was made from the BamH I-Sst I restriction fragment of the pBI221 plasmid (Clontech, Palo Alto, Calif.). The DNA probe was labeled with $[\alpha^{32}P]$dCTP using the random primer method (A. P. Feinberg and B. Vogelstein, Anal. Biochem., 132: 6–13, 1983).

To demonstrate the absence of any Agrobacterium contamination in the transformed plants, the same nylon filters hybridized with GUS DNA were stripped and rehybridized with the probe made from the Hind III 18 and Hind III 27 DNA fragment containing the vir B and vir D regions of pTiC58 (Depicker, A., et al (1980), Plasmid, 3: 193–211; Janssens, A., et al (1986), Plant Sci., 47: 185–193).

E) Assay for Neomycin Phosphotransferase II (NPTII) Activity

The NPTII activity in the putatively transformed calli and plants was assayed in at least four replicates using a modification of a method described by Radke, S. E., et al (Theor. Appl. Genet., 75: 685–694, 1988). Leaf tissue (100 mg fresh weight) was ground in a 1.5 ml Eppendorf tube with an equal volume (100 μl) of extraction buffer (2.5 mM Tris (pH 6.8), 0.143 mM β-mercaptoethanol, 0.27 mM leupeptin), and centrifuged for 15 min. at 4° C. Thirty μg protein were mixed with 10 ml of reaction buffer A (67 mM Tris-maleate, 42 mM $MgCl_2$, 400 mM $NH_4Cl$, 1.7 mM dithiothreitol, and 0.4 mg/ml kanamycin sulfate) or reaction buffer B (identical to reaction buffer A but without kanamycin).

Five μl of ATP solution (1.0 uCi $[\Gamma\text{-}^{32}P]$ATP and 0.75 mM ATP in reaction buffer B) was added. The samples were incubated in a 30° C. water bath for 30 min., then blotted onto three layers of Whatman P81 ion exchange paper placed on top of one piece of Whatman 3 MM paper using a "Hybri-Dot" blotting apparatus (BRL). All the ion exchange papers were washed twice with distilled water for a total of 4 min. and incubated in a 10 ml solution containing 1 mg/ml) proteinase K and 1% SDS at 65° C. for 60 min. The papers were then washed once with distilled water at room temperature for 4 min. and three times with distilled water at 85° C. for 4 min. The 3 pieces of paper were air-dried, stacked in their original positions, and exposed to X-ray film (Kodak) with an intensifying screen.

F) Assay of β-glucuronidase (GUS) Activity

To measure GUS activity in the putatively transformed calli and plants, at least two replicates of each sample were assayed according to R. A. Jefferson's method ("Analysis of gene organization and expression in plants," In: Plant Genetic Transformation and Gene Expression, A Laboratory Manual, Blackwell Scientific Publications, Oxford, Draper, J., et al (eds) pp. 263–339, 1988). Samples were homogenized with GUS extraction buffer (50 nM sodium phosphate (pH 7.0), 10 mM EDTA, 10 mM Triton X-100, 0.1% sarkosyl, and 10 mM β-mercaptoethanol). Twenty μg protein with an. equal volume of SDS sample buffer (62.5% mM Tris-HCl, 0.23% SDS, 10% glycerol, 50 mM β-mercaptoethanol, and 0.001% bromophenol blue) were incubated at room temperature for 15 min. Electrophoresis was run overnight at room temperature at 3 V/cm.

The gel was washed with 100 ml of GUS extraction buffer four times within 2 hours, incubated with GUS fluorometric buffer (1 mM methyl umbelli-ferylglucuronide in GUS extraction buffer) on ice for 30 min., and incubated at 37° C. in the dark for 30 min. The reaction was stopped with 0.2 M $Na_2CO_3$. The gel was illuminated by a 365 nm UV lamp with a Kodak 2E Wratten filter and photographed.

Localization of GUS expression in the transformed plants was evaluated by 5-bromo-4-chloro-3-indolyl glucuronide (X-gluc) histochemical assay (Benfey, P. N., et al (1989), EMBO J., 8: 2195–2202). Sections of leaf blade, sheath, stem or root of non-transformed or transformed 4-month-old plants were cut with a Vibratome (Oxford) sectioning device. Sections of 100 to 200 microns were incubated in a solution containing 1 mM X-gluc, 10 mM EDTA, 100 nM $NaH_2PO_4.H_2O$ (pH 7.0), and 0.1% Triton X-100 at 37° C. for 12 to 17 hrs. After staining, sections were rinsed in 70% ethanol for 5 min and chlorophyll in the sections was cleared by incubation for 10 min. in a solution of 5% formaldehyde, 5% acetic acid and 20% ethanol, followed by incubation for 2 min. in 50% ethanol, 2 min. in 100% ethanol, and two washings in distilled water. The sections were examined under a microscope. GUS activity in the R1 progeny was assayed by staining.

The R1 seeds were first germinated in MS medium containing 2 μg/ml 2,4-D and 300 μg/ml kanamycin to induce callus formation. Calli were formed from the germinating seeds after 1 week. A portion of each callus was removed and subjected to a modified GUS histochemical staining assay (Benfey, P. N., et al (1989), supra). Briefly, calli of the R1 progeny or control were incubated at 37° C. for 12 to 17 hrs. in a solution containing 1 mM X-gluc, 10 mM EDTA, 100 mM $NaH_2PO_4.H_2O$ (pH 7.0), and 0.1% Triton X-100. Photographs were taken with a Kodacolor 64 film under a dissecting Microscope (Olympus).

G) PCR

Two sequences in the GUS coding region were chosen to amplify a 410 bp fragment within the gene: The 5' primer (ACGTCCTGTAGAAACCCCAA) (SEQ ID NO: 11) and the 3' primer (AGTTCAGTTCGTTGTTCACACA) (SEQ ID NO: 12) located in the GUS coding region 3 bp and 417 bp downstream of the translation initiation site (ATG), respectively. One hundred μg of pAG8 were used as positive control; 100 ng of total rice DNA from young leaves of the R1 progeny were used. PCR was carried out in a 50 μl solution containing 50 mM KCl, 10 mM Tris-HCl, 15 mM $MgCl_2$, 0.1% gelatin (w/v), 1% Triton X-100, 0.2 mM of each deoxynucleoside triphosphate (dATP, dCTP, dGTP, dTTP), 2.5 units of Taq DNA polymerase (Promega), and 0.25 mM of each primer.

The sample was preheated at 94° C. for 5 min. and subjected to PCR amplification for 27 cycles. Cycling was controlled by a programmable thermal cycler (MJ Research, Inc.) programmed with the following conditions: denaturation, 94° C. for 1 min.; annealing, 58° C. for 2 min.; extension, 72° C. for 3 min. The sample was then incubated at 58° C. for 2 min. and 72° C. for 10 min. Five μl of the PCR product was electrophoresed in a 1% agarose gel and detected by staining with ethidium bromide. Southern blots of PCR products were hybridized with a probe made from the BamH I-Sst I GUS restriction fragment.

Results:

A) Transformation of Immature Rice Embryos by *Agrobacterium tumefaciens*

Figure 8A:
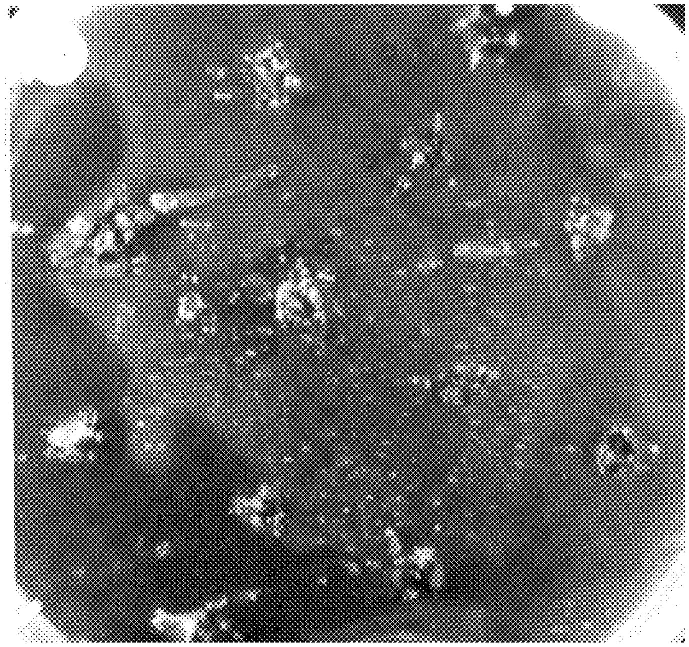
FIGS. 8A, 8B, 8C, 8D, 8E and 8F show the selection and regeneration of a transgenic rice plant. (8A) Nontransformed control calli on the selective medium (N6RF) containing 40 g/ml G418 three weeks after plating; (8B) Regeneration of shoot and roots from G418-resistant calli 8 weeks after inoculation with Agrobacterium; (8C) Transgenic plant grown on N6/G418 medium 9 weeks after inoculation; (8D) The transgenic plant grown in pot soil in greenhouse 16 weeks after inoculation; (8E) Tillering of the transgenic plant 18 weeks after inoculation; (8F) Seed-setting of the transgenic plant 24 weeks after inoculation.

Previously, we have shown that transformation of rice using Agrobacterium can be improved by the addition of PSC (Chan, M. T., et al (1992), supra). Here, presence of PSC with the Agrobacterium inoculum increased the transformation efficiency almost 3-fold (Table 3). Approximately 6.8% of immature rice embryos inoculated with Agrobacterium formed calli and proliferated on selective medium. The uninoculated or inoculated but non-transformed immature embryos turned brown and died within 3 weeks (FIG. 8A).

Figure 8B:
Figure 8C:
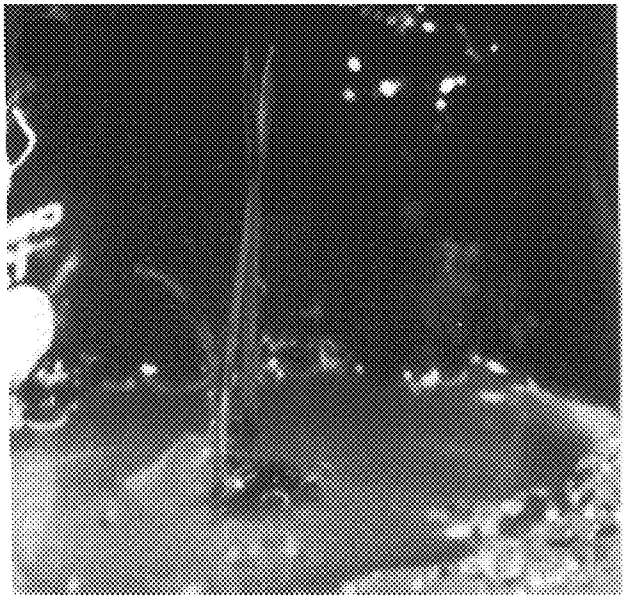
Figure 8D:
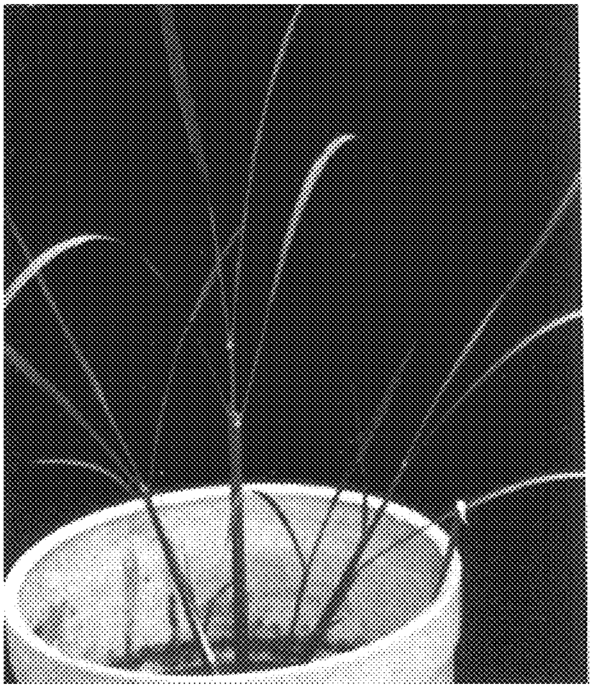
Figure 8E:
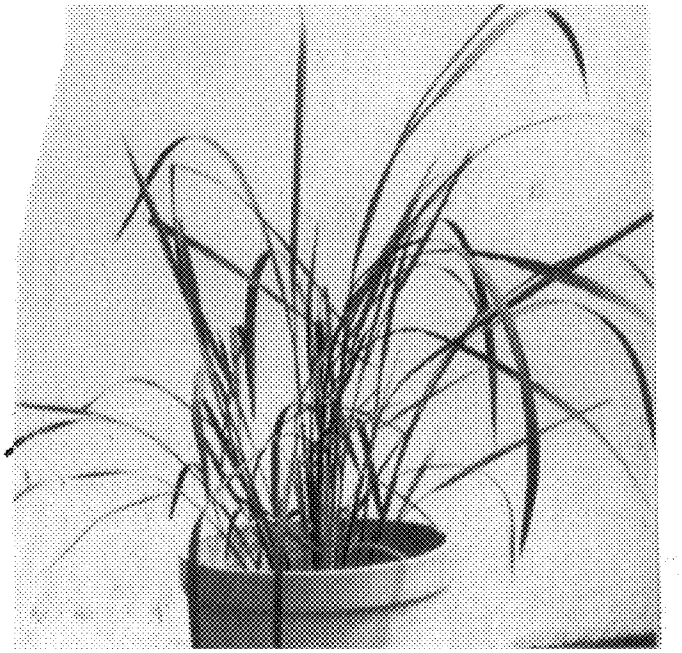
Figure 8F:

After culture of calli, shoots developed rapidly and roots formed spontaneously after 4 weeks (FIG. 8B). Among the 250 immature embryos inoculated, 17 calli and 4 plants were recovered from culture. The four transgenic plants were designated T1, T2, T3 and T4. These plants were ready to be transplanted into soil after 9 weeks of culture (FIG. 8C). Only one plant, T1, survived to flower and produce progeny (FIG. 8D–F). This transgenic plant exhibited normal phenotype and was fertile, except that it grew more slowly (about 14 weeks from being a 121 cm long plant to flowering) and produced less seeds (total 75 seeds) than a wild type plant. The other three transgenic plants were also transplanted into soil but did not survive.

B) DNA Analysis of Transformants

Figure 9:
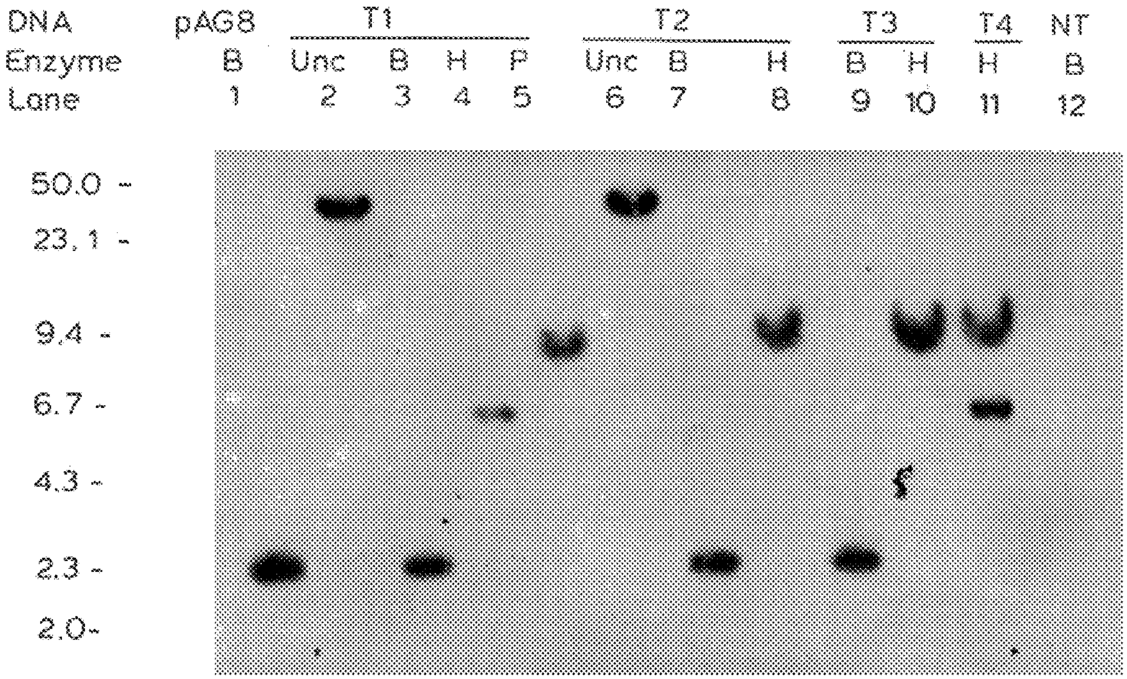
FIG. 9 shows a DNA blot analysis for detection of GUS gene in the transgenic rice plants. Genomic DNA was isolated from young leaves of wild type and transgenic plants. Five μg of DNA digested with various restriction enzymes were loaded on each lane. The Sst I/BamH I fragment containing GUS gene in pBI221 was used as the probe. Lane 1: pAG8 digested with BamH I; Lanes 2 to 5: DNA from transgenic plant T1; Lanes 6 to 8: DNA from transgenic plant T2; Lanes 9 to 10: DNA from transgenic plant T3; Lane 11: DNA from transgenic plant T4; and Lane 12: DNA from a non-transformed control plant. Abbreviations of restriction enzymes: B. BamH I; H. Hind III; P, Pst I; Unc, undigested.

To provide physical evidence for the integration of foreign DNA into the genome, Southern blot analysis of restriction digests of genomic DNA from leaves of the 4 transgenic plants (T1, T2, T3 and T4) was performed using the GUS DNA from pBI221 as a probe (FIG. 9). The size of the undigested rice genomic DNA (Unc) was about 50 kb (FIG. 9, lanes 2 and 6). After digestion with BamH I (B), GUS DNA was detected as a fragment of the expected size 2.3 kb (FIG. 9, lanes 3, 7 and 9), the same size as that present in pAG8 (FIG. 9, lane 1). After digestion with Hind III (H) or Pst I (P), the 50 kb band disappeared and the lower molecular weight DNA fragments appeared (FIG. 9, lanes 4, 5, 8, 10 and 11).

Transgenic plant T4 appeared to have two integration sites for the GUS gene as two hybridization bands were detected when DNA was digested with Hind III (FIG. 9, lane 11). Since the GUS DNA probe only hybridized to DNA from the 4 transgenic plants but not to the non-transformed control plant (NT) (FIG. 9, lane 12), this indicates that the GUS gene was integrated into the rice genome.

To prove that the GUS DNA detected in FIG. 9 did not result from contamination with Agrobacterium in the transgenic plants, the same nylon filter was reprobed with vir B and vir D DNA. As the vir genes are not located on the Ti-plasmid, Southern blot analysis using vir DNA as a probe should provide a reliable way to detect Agrobacterium contamination. The Agrobacterium strain A281 used in this experiment was derived from strain C58 which carries pTiC58. A probe made from the Hind III 18 and Hind III 27 DNA fragments containing the vir B and vir D regions of pTiC58 should thus hybridize to DNA of Agrobacterium. However, no hybridization band was observed when using the vir DNA as a probe (data not shown), clearly demonstrating that the GUS DNA detected in the genome of the transgenic plants was not due to persisting Agrobacterium cells in the rice tissues.

C) Expression of GUS and NPTII in the Transgenic Calli and Plants

The GUS coding sequence in pAG8 was placed downstream of the putative 5' promoter region of an α-amylase gene (αAmy8) so as to make a transcriptional fusion. To investigate the promoter function of the 1.2 kb long 5' region of this α-amylase gene, expression of the GUS gene was determined by the presence of GUS activity in the transgenic calli and plants.

Figure 10A:
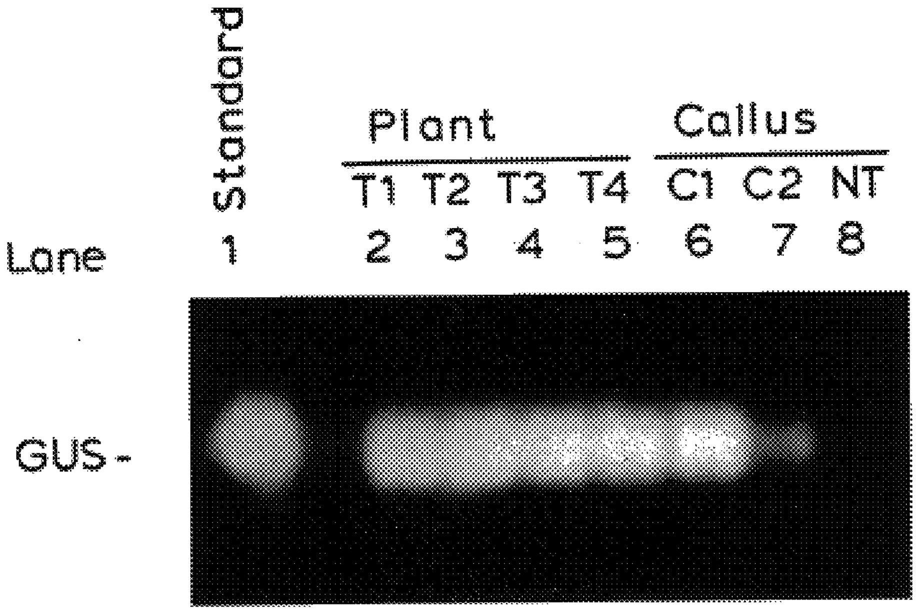
FIGS. 10A and 10B show the analysis of GUS and NPTII activities in the transgenic calli and plants. (10A) Analysis of GUS activity in transgenic rice. Protein extracts from transformed and non-transformed rice plants and calli were separated using 7.5% SDS-PAGE. The gel was reacted with 1 mM methyl umbelliferyl glucuronide (MUG) and photographed as described in "Materials and methods." Lane 1: standard *E. coli* β-glucuronidase; Lanes 2–5: protein extract from transformed plants; Lanes 6–7: protein extract from transformed calli; Lane 8: protein extract from non-transformed callus. Twenty μg per lane of protein was loaded in lanes 2 to 8. (10B) Analysis of neomycin phosphotransferase II activity in transgenic rice. Thirty μg protein extracts from transformed or non-transformed rice plants and calli were reacted with [Γ-$^{32}$P]-ATP, dot blotted on Whatman P81 papers and autoradiographed as described in "Materials and methods." Row A: reactions with kanamycin; Row B: reactions without kanamycin; Lanes 1–3: protein extracts from transgenic plants; Lanes 5–6: protein extracts from transformed calli; Lane 4 and 7: protein extracts from non-transformed plants and callus, respectively.

GUS present in the cell extracts migrated in an SDS-polyacrylamide gel with an apparent molecular weight of 69 kDa (FIG. 10A). The levels of GUS activity that could be detected in the four transgenic plants and callus C1 were similar (FIG. 1A, lanes 2–6). The lower level of GUS activity in transgenic callus C2 (FIG. 10A, lane 7) seems to be coupled with its lower level of NPTII activity (FIG. 10B, lane 6. No GUS activity was detected in the non-transformed callus (NT) (FIG. 10A, lane 8). The results suggest that the 1.2 kb 5' region of αAmy8 contains an efficient promoter for regulating GUS gene expression.

Figure 10B:
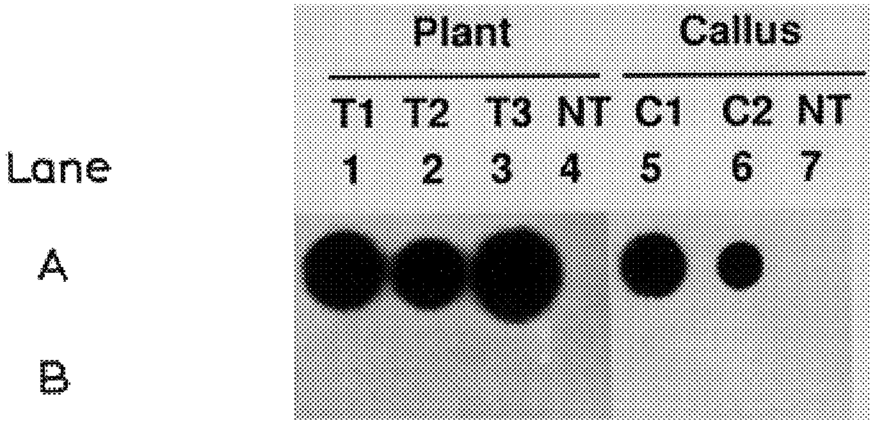

Plasmid pAG8 contains the NPTII coding region driven by the nopaline synthase promoter. Consequently, selection for plants carrying foreign genes should be achieved using media containing G418. The NPTII activity was further determined in 8 randomly chosen transformed calli (R0) and 3 transgenic plants (T1, T2, and T3). All of the 8 transgenic calli expressed NPTII activity and data for 2 of them (C1 and C2) are presented (FIG. 10B, lanes 5 and 6). NPTII activity was also detected in the 3 transgenic plants (FIG. 10B, lanes 1, 2, and 3). No activity was observed in the non-transformed callus (FIG. 10B, lane 7) and plant (FIG. 10B, lane 4).

D) Histochemical Localization of GUS in Transgenic Rice Plant

Figure 11A:
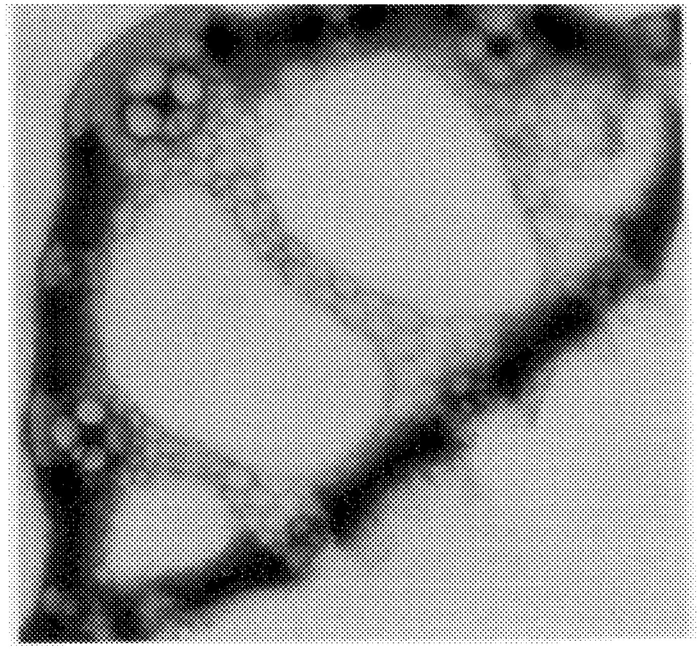
FIGS. 11A–11J. Expression of the αAmy8 (1.2 kb)/GUS gene in various tissues of transgenic rice plant T1. Thin sections of each organ from transformed or non-transformed plants of 100 cm in height were stained with X-gluc as described in Materials and methods. (11A) Cross section of a leaf blade from a non-transformed plant; (11B) Cross section of a leaf blade from transgenic plant T1; (11C) Higher magnification of the boxed area in (11B); (11D) Cross section of stem of one of the tillers from a non-transformed plant; (11E) Cross section of stem of one the tillers from transgenic plant T1; (11F) Higher magnification of the boxed area in (11E); (11G) Cross section of a leaf sheath from transgenic plant T1; (11H) Cross section of young leaves embedded inside the leaf sheaths of one of the tillers from transgenic plant T1; (11I) Cross section of a root of transgenic plant T1; (11J) Unsectioned root hair from transgenic plant T1. Abbreviations: ph, phloem; mx, metaxylem tracheary element; sc, sclerenchyma; par, parenchyma.
Figure 11B:
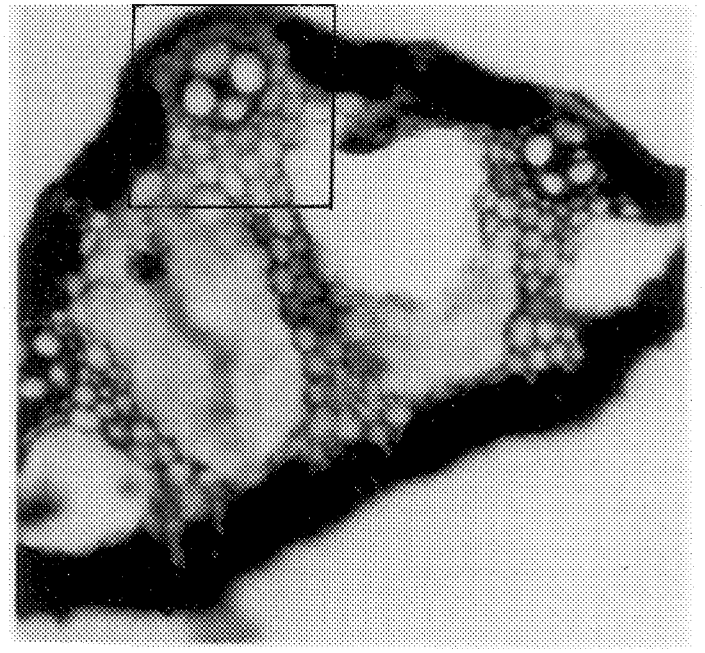
Figure 11C:
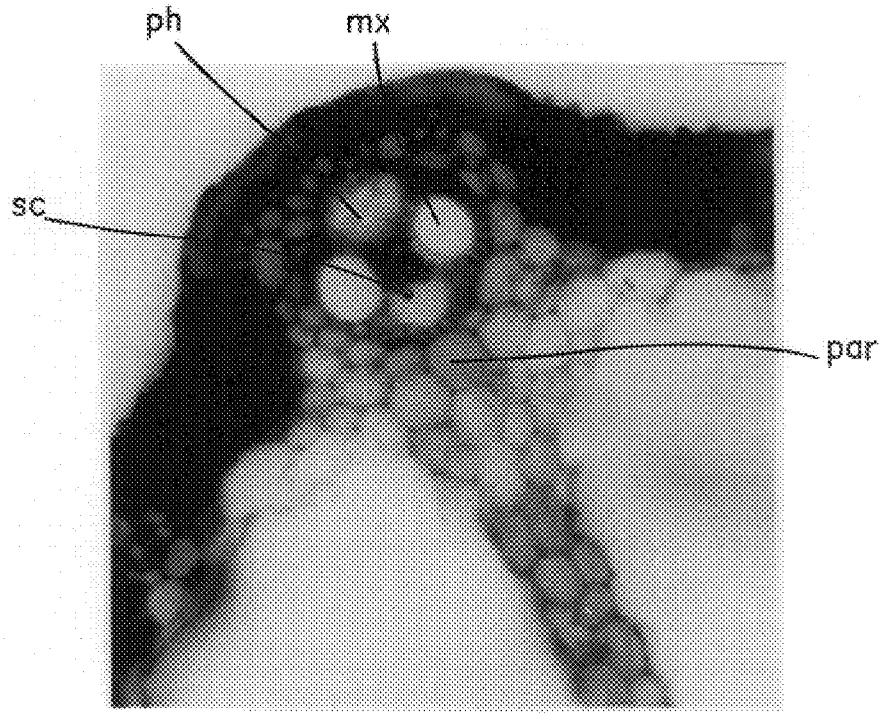
Figure 11D:
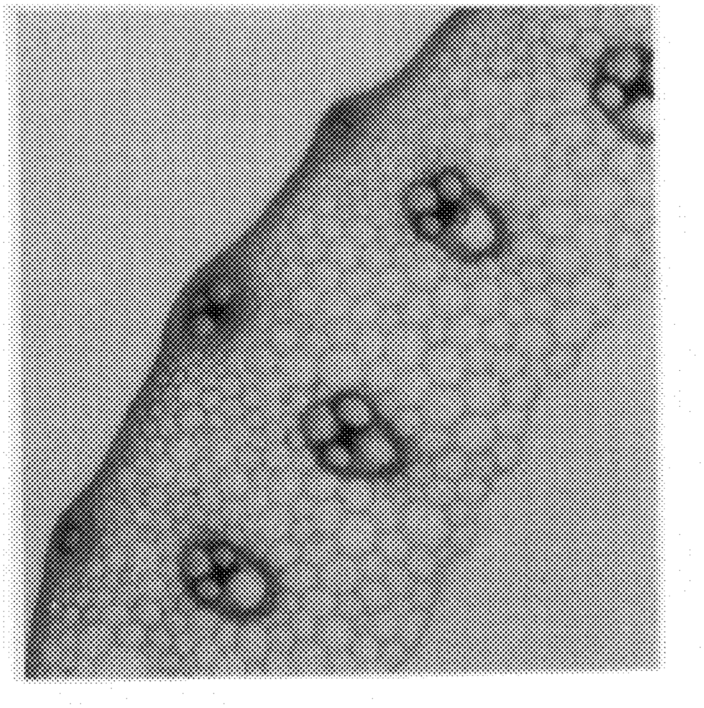
Figure 11E:
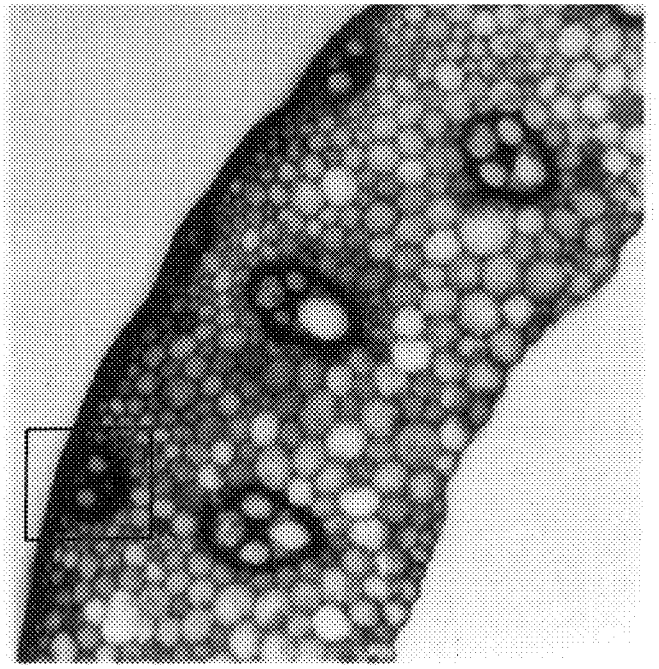
Figure 11F:
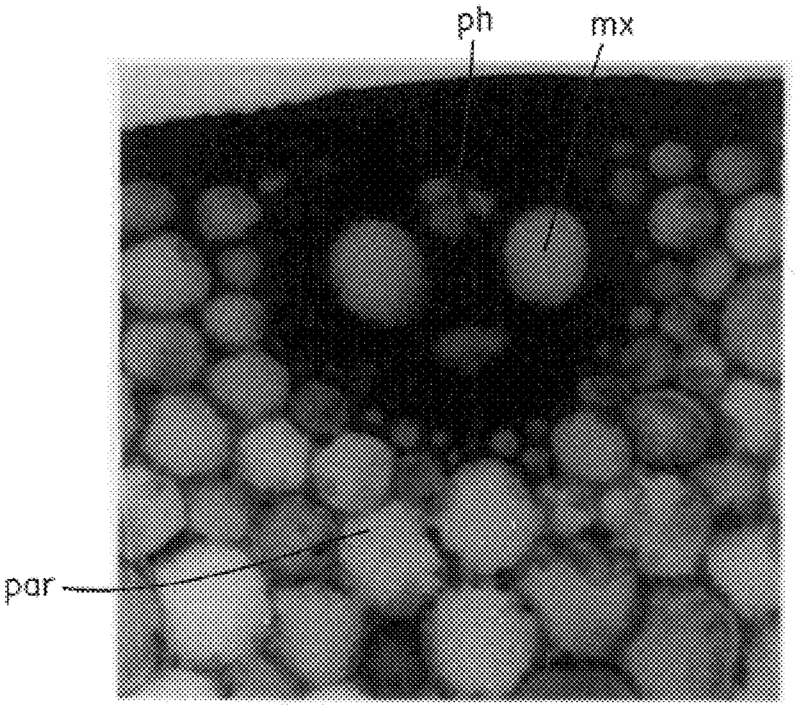
Figure 11G:
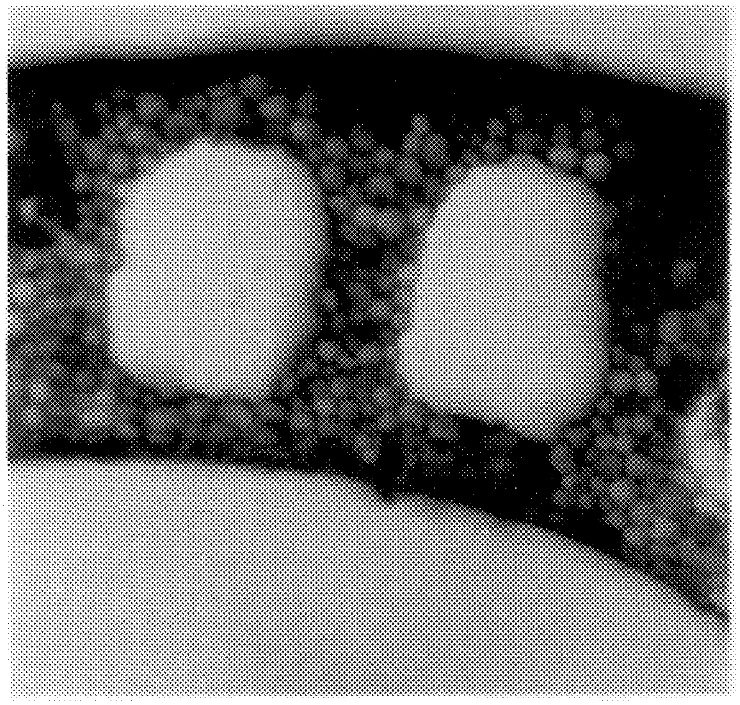
Figure 11H:
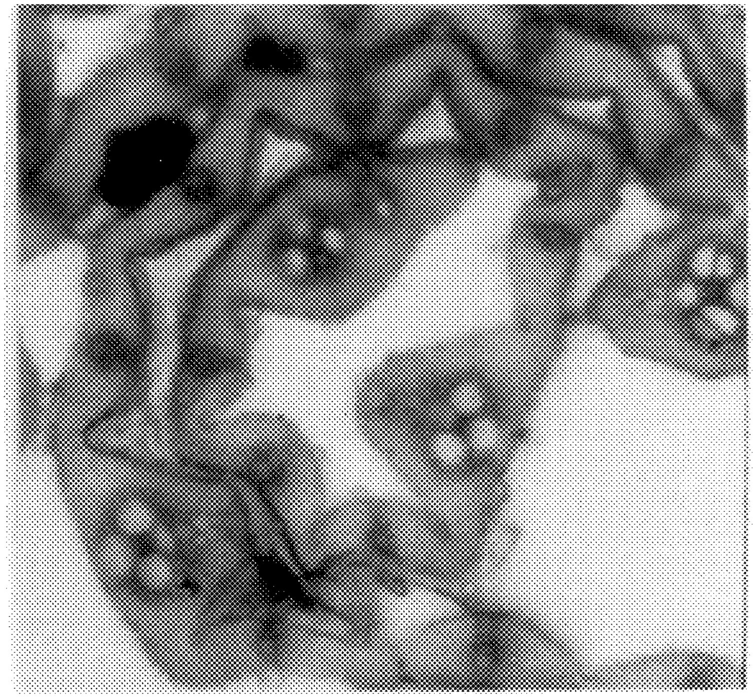
Figure 11I:
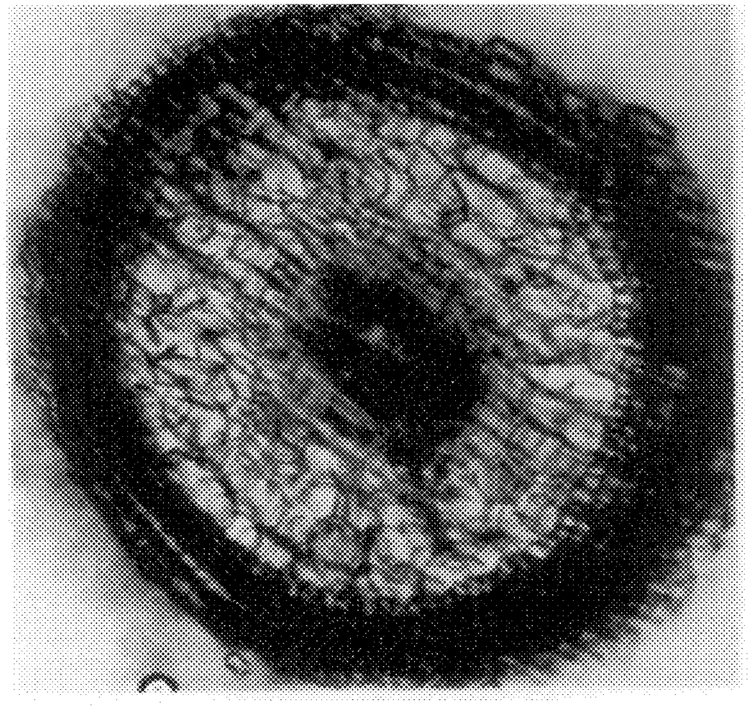
Figure 11J:
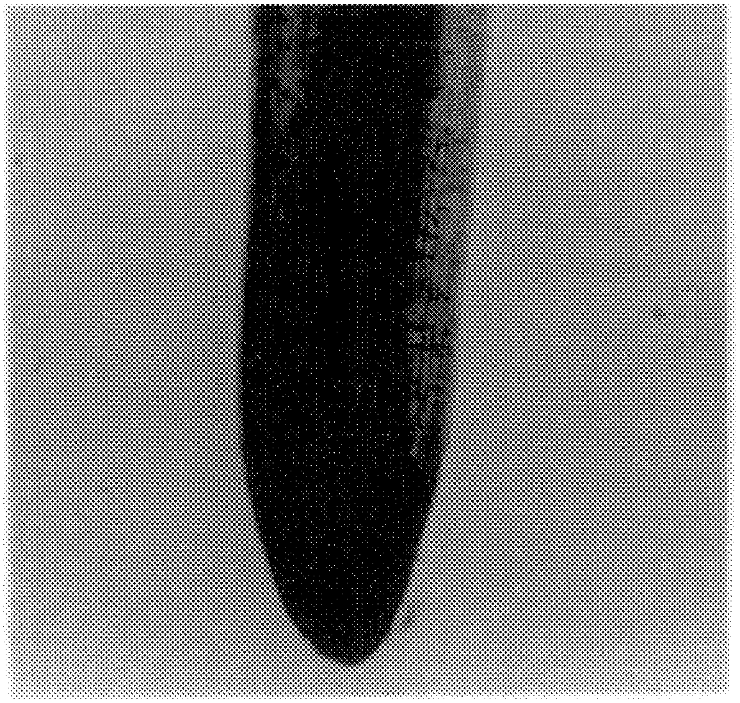

To localize the cellular expression pattern of the GUS gene driven by the 5' region of αAmy8, various tissues of the transgenic plant (T1) were sectioned and subjected to histochemical staining (FIGS. 11A–11J). Blue staining of sections appeared 17 hr after incubation in the substrate. GUS expression was observed in all cell types of leaf blade (FIGS. 11B and 11C), stem (FIGS. 11E and 11F), and sheath (FIG. 11G). Tissue sections of leaf blade and stem from non-transformed control plants displayed no staining (FIGS. 11A and 11D). Transverse sections of root revealed that the epidermal cells were stained blue and the cortex cells were stained lightly (FIG. 11I). Unsectioned root hairs showed intense staining in the vascular cylinder and light staining in the cortex cells (FIG. 11J). No GUS expression was found in the sections of very young leaf blades which were embedded inside sheaths (FIG. 11H).

E) Analysis of R1 Progeny

Of the 75 seeds harvested from the transgenic plant T1, 36 seeds were germinated on selective media (containing 300 μg/ml kanamycin) to induce callus formation. Within 10 days, 32 germinating seeds formed calli and continued to grow and were identified as resistant. The other 4 germinating seeds also formed calli, but turned brown and died later. About half of each kanamycin resistant callus was removed and assayed for GUS activity.

Figure 12:
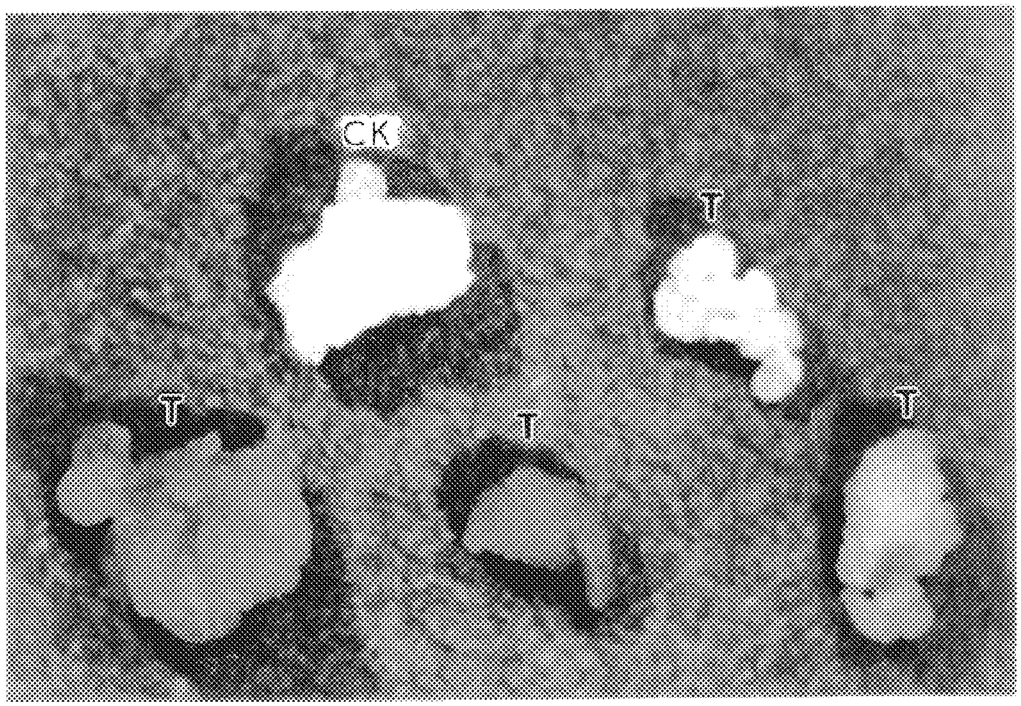
FIG. 12 shows the analysis of GUS activity in R1 seeds of transgenic plant T1. The seeds were germinated in MS medium containing kanamycin and 2,4-D to induce callus formation. The calli were subjected to GUS histochemical staining assay as described in "Materials and methods." CK: callus derived from a seed of non-transformed plant; T: calli derived from seeds of transgenic plant T1.

Of the 32 calli assayed, 28 showed blue staining and 4 calli remained yellow, similar to the non-transformed control (data for 4 of them are presented in FIG. 12). Calli derived from different transgenic R1 seeds showed considerabie variation in GUS activity, as revealed by different degrees of blue staining (FIG. 12).

Figure 13A:
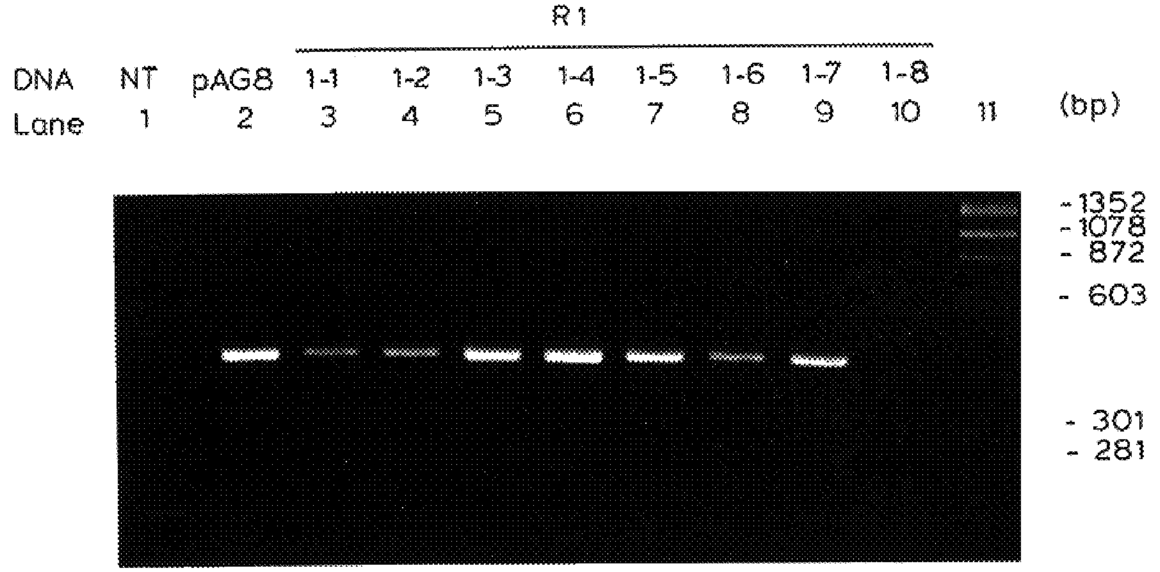
FIGS. 13A and 13B show the PCR amplification of a 410 bp GUS DNA fragment from R1 progeny of transgenic rice plant T1. DNA was isolated from young leaves of R1 progeny of transgenic plant T1. PCR was performed as described in "Materials and methods." (13A) Amplified DNAs were electrophoresed in 1% agarose gel and detected by ethidium bromide staining. (13B) Same DNAs as in (A) were blotted on Gene Screen membrane (Du Pont, Wilmington, Del.), hybridized with a $^{32}$P-labeled GUS DNA probe, and autoradiographed. Lane 1: DNA template from non-transformed plant (NT) was used as a negative control; Lane 2: DNA template from plasmid pAG8; Lanes 3–10: DNA template from R1 progenies (no. 1-1 to 1-8) of transgenic rice plant T1.
Figure 13B:
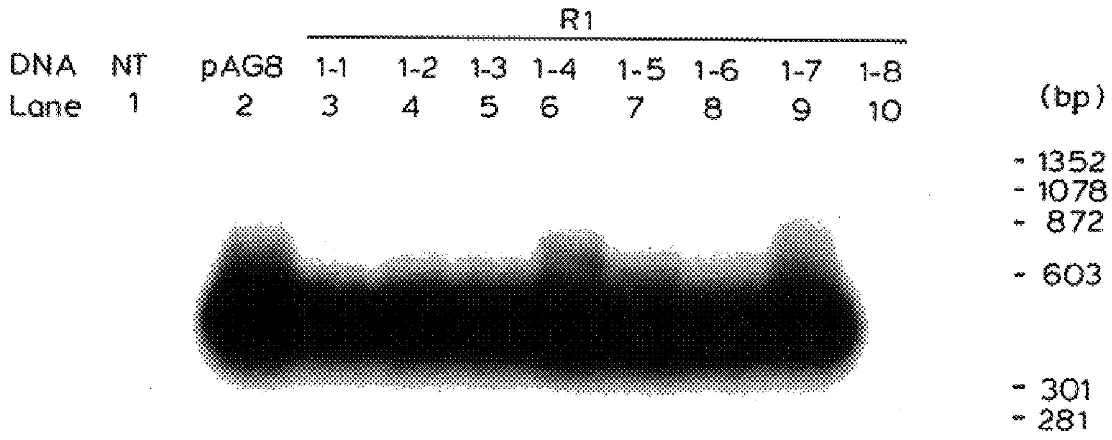

Among the remaining 39 seeds of T1, 18 seeds were germinated and grown in a greenhouse. DNA was isolated from young leaves of 13 of these R1 plants when they were 10 cm tall. The DNA was subjected to PCR amplification of a 410 bp fragment within the GUS coding region (FIG. 13A). Identification of the amplified DNA was established by blot hybridization to a $^{32}P$-labeled GUS DNA probe (FIG. 13B). These results further confirmed the presence of GUS genes in the R1 progeny of the original transformant.

Discussion

Although several methods for the transformation of rice using protoplasts or suspension cells are available at present, attempts to regenerate mature plants from the transformed protoplasts or suspension cells of many rice varieties have been unsuccessful. Methods based on the use of the soil bacterium *Agrobacterium tumefaciens* are still preferred in many instances, as Agrobacterium-mediated transformation does not require protoplasts and, in general, results in higher transformation efficiency and a more predictable pattern of foreign DNA integration than other transformation techniques (Czernilofsky, A. P., et al (1986), DNA, 5: 101–113). Here we show that transgenic rice plants are successfully produced using an Agrobacterium-mediated DNA transfer system.

Two factors may have contributed to the success in rice transformation and regeneration. The first factor is the addition of PSC during the co-cultivation of Agrobacterium with the immature rice embryos. PSC probably contains substances which enhance the Agrobacterium-mediated T-DNA transfer process, since PSC induced the formation of calli one week earlier and enhanced the frequency of transformation about 3-fold (Table 3). PSC is rich in acetosyringone and sinapinic acid (Chang, H. H., et al (1991), supra), which are generally believed to enhance transformation-of various plant species (Stafer, W., et al (1985), supra). However, the role of these two compounds in the success or efficiency of transformation is not clear at this time. The transformation percentage of 1.6% that we obtained for producing transgenic plants would render the use of Agrobacterium to transfer genes into rice more feasible.

The second factor for successful transformation and regeneration is the use of immature rice embryos (10 to 12 days after pollination) as the transformation materials, since they may contain less inhibitors or more virulence inducers than mature embryos to T-DNA transfer. Immature embryos of maize have also been shown to be competent for Agrobacterium-mediated gene transfer and that competence depends on genotype and developmental stage. Meristematic tissue of the immature embryo becomes competent at developmental stages that correlate with the differentiation of the first one to two leaf initials (M. Schlappi and B. Horn (1992), Plant Cell, 4: 7–16).

Therefore, the immature embryos at some developmental stages may produce conditions which increase the success of T-DNA transfer, such as (a) the availability of vir gene-inducing substances, (b) low production of bacteriotoxic substances, (c) favorable endogenous hormone levels, and (d) the availability of receptors for attachment of Agrobacterium (M. Schlappi and B. Horn (1992), supra).

Although only four plants could be regenerated from the transformed calli in this experiment, all these plants were proved to be real transformants. Integration of chimeric genes into the genomes of the four transgenic plants was confirmed by hybridization of the restricted genomic DNA. In addition, our experiments ruled out the possibility of Agrobacterium contamination of the rice tissues as a possible source of the hybridization bands.

Detection of NPTII and GUS activities in the transgenic plants indicates that the integrated foreign genes were expressed. Our results also indicate that kanamycin can be used to select transformed rice cells from a mixed population of transformed and non-transformed cells. To avoid the occurrence of kanamycin escapees, it is important that selection be applied immediately after the co-cultivation.

Of the 4 regenerated transgenic plants, only one plant (T1) survived to flower and produce progeny. Transgenic plant T1 flowered in December, when the room temperature in the greenhouse was below 20° C., but we don't know whether this was one of the reasons for its low yield (75 seeds). The transgenic R1 progeny inherited and expressed the NPTII and GUS genes, as shown by their resistance to kanamycin and expression of GUS activity. A 3:1 ratio was expected in the progeny from self-pollination, assuming that the gene was transmitted as a single dominant locus.

In the GUS staining assay in conjunction with kanamycin selection of calli derived from immature embryos of 32 R1 progeny, 28 were GUS positive and kanamycin resistant, 4 were GUS negative but kanamycin resistant, and 4 were GUS negative and kanamycin sensitive. This 28:8 or 3.5:1 ratio indicates that GUS segregation in the R1 progeny of transgenic plant T1 is consistent with the predicted 3:1 Mendelian inheritance pattern in a heterozygous× heterozygeous cross.

The lack of GUS activity in the 4 kanamycin-selected R1 may indicate that the GUS gene was either absent or present but nonfunctional. Absence of the GUS gene in the kanamycin-resistant R1 could be due to deletion of the GUS gene via DNA rearrangement. PCR amplification of GUS DNA fragments was achieved from DNA of 13 out of 18 R1 plants tested. The 13:5 or 2.6:1 ratio is also close to the theoretical Mendelian segregation pattern.

The rice α-amylases are encoded by a multigene family which contains at least ten distinct members (Huang, N. et al (1990), Plant Mol. Biol., 14: 655–668). Genomic and cDNA clones representing different members of the α-amylase gene family have been isolated in our laboratory. Expression of the α-amylase gene, αAmy8, is $GA_3$-regulated in germinating seeds. This gene is also one of the major metabolite-regulated genes in cultured suspension cells of rice (Yu, S. M., et al., unpublished result). In our experiments, the DNA resulting from fusion of the 1.2 kb 5' flanking region of αAmy8 to the reporter gene GUS was transformed into rice. Expression of GUS in the transgenic rice indicates that this 1.2 kb fragment contains a functional promoter.

Thus, use of transgenic rice carrying a reporter gene under the control of an α-amylase promoter has provided a new tool for analyzing the regulatory elements in the α-amylase promoters. Such studies should lead to an understanding of the regulation of α-amylase gene expression in rice.

To our surprise, the histochemical localization of GUS activity indicated that the αAmy8 promoter was functional in all cell types of the mature leaves, stems, sheaths and roots of the transgenic rice plants. The only tissues which did not express GUS were the very young leaves embedded inside the sheaths. GUS was active in cells of the epidermis, mesophyll and vascular bundles of leaves. It was also active in the epidermis, cortex, and vascular cylinder of the roots. Therefore, the expression of αAmy8/GUS is not tissue-specific. Rather, it is temporally regulated in the transgenic plant, though it is not known at which growth stage of leaves αAmy8 begins its expression. Our histochemical studies were performed only with T1, the single transgenic plant that survived after being transferred to soil.

The possibility that αAmy8/GUS was inserted close to a very active enhancer in the rice genome, which could render high-level expression or loss of tissue-specific expression of the foreign gene cannot be ruled out. However, αAmy8 is apparently one of the major metabolite-regulated genes in cultured suspension cells (Yu, S. M., et al. (1992), Gene, inpress) and thus probably plays an important role in the carbohydrate metabolism of the vegetative tissues of rice.

Therefore, it is not totally surprising that the GUS gene driven by αAmy8 promoter is constitutively expressed in every cell type of different tissues of the transgenic plant. If this is also true for the naturally existing α-amylase gene in wild type plants, it would be interesting to know the physiological function of αAmy8 promoter in rice. The general distribution and levels of GUS activity obtained in different tissues of stably transformed rice plants indicate the potential of αAmy8 promoter as a positive control for studies in gene activity in transgenic rice.

In conclusion, this experiment demonstrates that immature rice embryos are susceptible to Agrobacterium-mediated transformation and that the foreign genes transferred are inherited by the next generation of the transformant.

In addition to the rice variety Tainung 62 (Japonica type) used in this experiment, T-DNA has also been successfully transferred into genomes of other rice varieties including Tainan 5 (Japonica type) and Taichung Native no. 1 (Indica type) using the same approach (M. T. Chan, H. H. Chang and S. M. Yu, unpublished result). Therefore, it is proposed that this simple approach can be applied to transform other rice varieties and, with modification, other monocot species.

EXAMPLE III

As noted from the beginning, an objective of the present invention is to provide a new gene expression system functional in plant host cells, thereby rendering the expressed gene product capable of being directly recovered from medium. To achieve this purpose, based upon the results obtained in Example II, further experiments were carried out to investigate the regulation of the promoter region of αAmy8 with respect to the expression of the foreign gene GUS in the present transgenic rice cells.

More specifically, it was studied whether or not the expression of said GUS gene under the control of said promoter will be influenced by a sugar-depleted or sugar-free condition. The following experiments adopted the materials and methods described in Example II.

Figure 14:
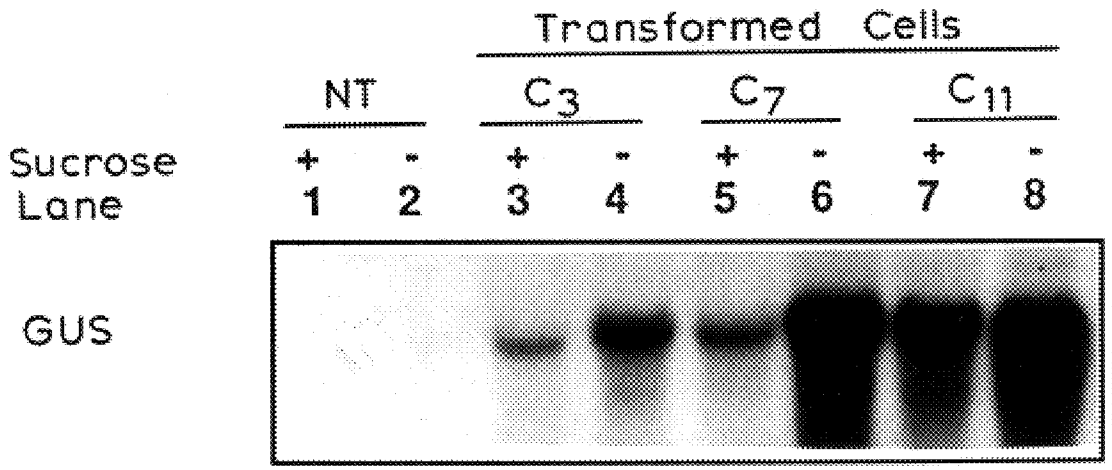
FIG. 14 shows the expression of GUS in transgenic rice calli.

Immature embryos of rice were transformed with *Agrobacterium tumefaciens* which carried the αAmy8/GUS chimeric gene (pAG8). Calli derived from the transformed embryos were then grown in liquid MS medium containing 2 μM 2,4-D to establish a suspension culture of rice. The cell cultures were subcloned every 5 days. For this experiment, suspension cells were transferred to medium with (+) or without (−) sucrose for two days. RNA was purified from the treated cells and the GUS mRNA was detected by Northern blot analysis using $^{32}$P-labeled GUS DNA as probe. 10 μg of total RNA was loaded in each lane. The results are shown in FIG. 14. To detect whether the expressed GUS protein was maintained in the transformed cells or secreted into the culture medium, rice suspension cells were grown and treated under conditions identical to the above experiment. Proteins were extracted from the treated cells or collected from the medium, subjected to Western blot analysis and detected with the GUS antibody. 20 μg of total proteins were loaded in each lane. The results are shown in FIG. 15.

Results and Discussions

Referring to FIG. 14, NT indicates the non-transformed cells; C3, C7 and C11 are three independent transformed cell lines. The C11 cell line was deposited in the Fermentation Research Institute Agency of Industrial Science and Technology (FERM, now renamed as National Institute of Bioscience and Human-Technology), Japan on Nov. 4, 1992, with the accession number of FERM BP-4064 under the Budapest Treaty. No GUS mRNA was detected in the non-transformed cells, either in the presence or absence of sucrose (lane 1 and 2). GUS mRNA was detected in cells of the three cell lines grown in medium containing sucrose (lanes 3, 5 and 7). The mRNA levels increased in cells grown in sucrose-free medium (lanes 4, 6 and 8).

Figure 15:
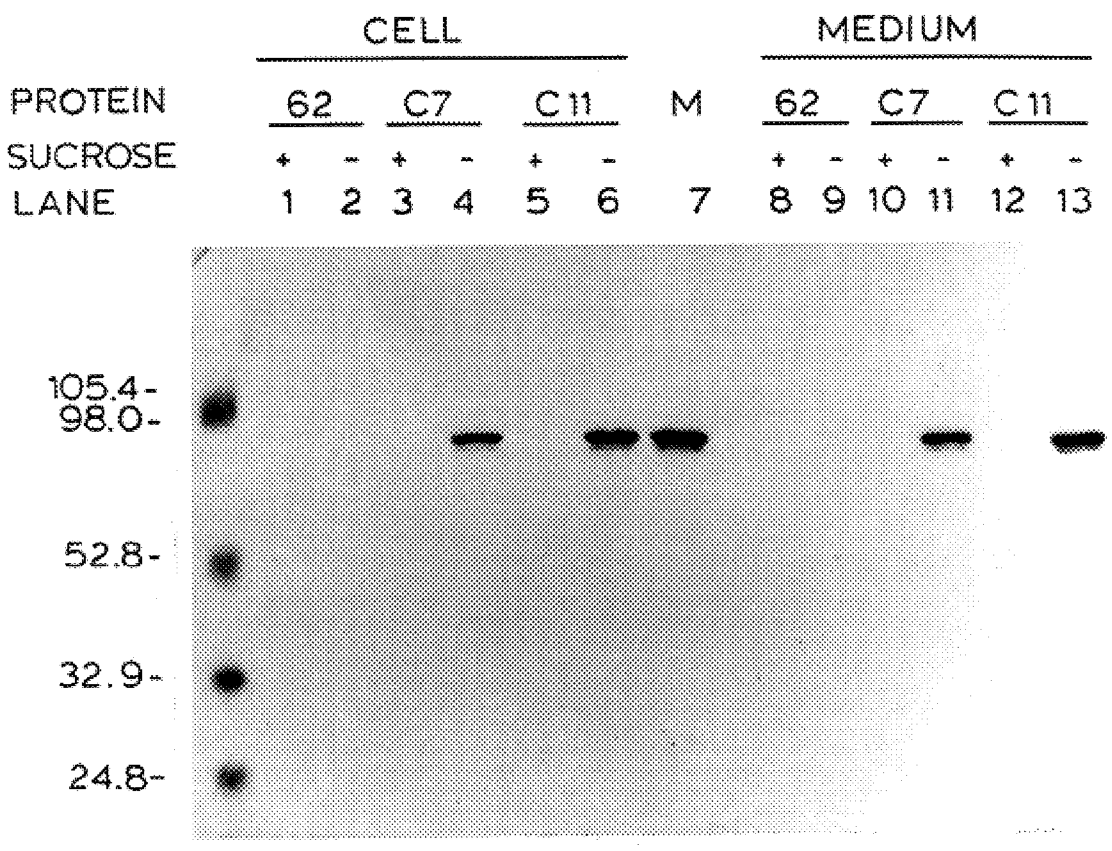
FIG. 15 shows the accumulation of GUS protein in transgenic rice cells and medium.

In FIG. 15, arrow (—) indicates the position of GUS protein. No GUS protein was detected in the non-transformed cells or their culture media, either in the presence or absence of sucrose (lanes 1, 2, 8 and 9). No GUS protein could be detected in the transformed cells or media in the presence of sucrose (lanes 3, 5, 10 and 12), either. As expected, the GUS protein could be easily detected in the transformed cells and media in the absence of sucrose (lanes 4, 6, 11 and 13).

Accordingly, it can be confirmed from the above obtained results that the present gene expression system can achieve at least two main advantages. First, the expression of the αAmy8/GUS chimeric gene is well controlled by the promoter region of αAmy8, especially under the sugar-depleted or sugar-free condition of the culture medium. Hence, the present gene expression system comprising the promoter of an α-amylase gene can promote the quantitative production, under sugar-depleted or sugar-free condition, of a desired gene product, such as the GUS protein exemplified here. Second, inasmuch as the promoter region of said chimeric gene also includes a DNA sequence encoding the signal sequence of α-amylase, the expressed gene product (GUS) will be secreted into the culture medium, rendering said gene product recoverable from the culture medium. As a result, the procedures for recovery and purification of the desired gene product can be simplified, and the contamination therein can also be diminished.

EXAMPLE IV

Further experiments were carried out to investigate whether or not the regulation of the promoter region of α-amylase gene with respect to the expression of a foregin gene, such as the GUS reporter gene, will still work well in transgenic plant hosts other than rice crop, e.g., the dicotyledous plants. For this purpose, tobacco and potato were chosen as plant hosts and tested in the following examples, and the obtained experimental results well demonstrate that the expression system established per this invention, which comprises a 1.2 kb promoter region from rice αAmy8 gene as obtained in Example I, provides a simple and convenient means for large-scale production of a desired foreign protein in plant host cells transformed thereby.

Experimental Procedures

I. Plasmids and Bacterial Strains

Plasmids used herein were constructed as previously described in Example II. Plasmid αAmy8-C which carries a 1.4 kb α-amylase cDNA insert in pBluescript KS$^+$ (Stratagene) was originally subcloned from a rice genomic clone OSAmy8C as detailed in Example I. The generation of *Agrobacterium tumefaciens* strain A281 (pTiBO542+pAG8) was described in Example II.

II. Plant Material

Potato variety *Solanum tuberosum* L cv. ADH69 and tobacco variety *Nicotiana tabacum* L. cv. Petit Havana SR1 were used in this study. Tobacco cell lines TO1 and TO2 were obtained by transformation of leaf disk with Agrobacterium (Horsch et al., in "Plant Molecular Biology Manual," pp. 1–9, Kluwer Academic Publishers, Dordrecht, 1988). Potato cell lines P1 and P2 were obtained by transformation of microtuber with Agrobacterium (Chang and Chan, *Bot. Bull. Acad. Sin.,* 32: 63–70, 1991). In addition, rice cell lines C7 and C11 of Example III and rice cell lines C51 and C52 from *Oryza sativa* L. cv. Tainan 5, which were obtained by transformation of immature rice embryos with Agrobacterium in a same manner as described in Example II, were also detected in this experiment for the purpose of comparison. Suspension cell cultures were propagated as described previously (Yu et al., J. Biol. Chem., 266: 21131–21137, 1991). Suspension cells were collected by filtration through a 400-mesh nylon sieve, blot-dried on paper towels-and weighed. Medium was collected by filtration through the Whatman No. 1 filter papers. The collected cells or medium were quick-frozen in liquid nitrogen and stored at −70° C. until use.

III. Southern Blot Analysis

Total DNA was isolated from suspension cells of putative transgenic cell lines. Five μg DNA was digested with Hind III, fractioned by agarose gel (0.8%) electrophoresis, and transferred to a GeneScreen membrane (Du Pont). The GUS DNA used as a probe was made from the BamHI-SstI restriction fragment of plasmid pBI221 (Clontech) and labeled with [α-$^{32}$P]dCTP using the random primer method (Feinberg and Vogelstein, Anal. Biochem., 132: 6–13, 1983).

IV. Northern Blot Analysis

Total RNA was purified from suspension cells according to the method of Belanger et al (Proc. Natl. Acad. Sci. USA, 83: 1354–1358, 1986). RNA blot analysis was performed as described by Thomas (Methods Enzymol., 100: 255–266, 1983). The 1.4 kb α-amylase cDNA insert used as the probe was excised from the plasmid vectors by restriction enzyme EcoRI and labeled with [α-$^{32}$P]dCTP using the random primer method (Feinberg and Vogelstein, Anal. Biochem., 132: 6–13, 1983).

V. GUS Activity Assay and Western Blot Analysis

Total proteins were extracted by grinding 0.1–0.2 g of cells in 500 ml of GUS extraction buffer (50 mM sodium phosphate buffer, pH 7.0, 10 mM EDTA, 0.20% Triton X-100, 0.1% Sarkosyl, 10 mM β-mercaptoethanol). The GUS activity assay was done as described by R. A. Jefferson (1988) in "Plant Genetic Transformation and Gene Expression, A Laboratory Manual," pp. 263–339, Blackwell Scientific Publications, Oxford.

For immunoblotting use, the α-amylase polyclonal antibodies were raised in rabbit against the rice α-amylases purified from the culture medium and the GUS polyclonal antibodies were purchased from Molecular Probes, Inc.

Results of Experiment

I. Expression of α-Amy8/GUS in Other Rice Cultivar and Plant Species

Figure 16:
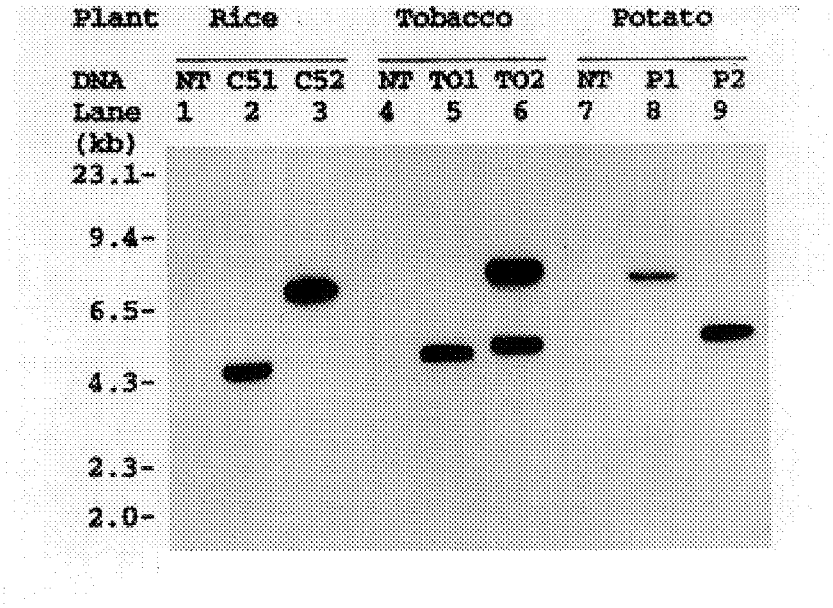
FIG. 16. Southern blot analysis for detection of GUS DNA in the transgenic plants. Genomic DNA was isolated from calli of the putative transgenic plants. Five μg of DNA was digested with HindIII and hybridized with the $^{32}$P-labeled GUS DNA probe. DNA from putative trangenic cell lines of rice cv. Tainan 5 (C51 and C52), tobacco (TO1 and TO2), and potato. (P1 and P2). NT indicates DNA of the non-transformed control cell lines.

To study whether the expression of α-Amy8/GUS can be regulated by sugars in a similar mannner in different rice cultivar and plant species, plasmid pAG8 was introduced into rice cv. Tainan 5, tobacco and potato cells via the Agrobacterium-mediated transformation. Integration of the chimeric α-Amy8/GUS gene into the randomly selected putative transgenic cell lines was demonstrated by Southern blot analysis (FIG. 16). The GUS DNA was detected in the genome of rice cell lines C51 and C52 (FIG. 16, lanes 2 and 3), tobacco cell lines TO1 and TO2 (FIG. 16, lanes 5 and 6), and potato cell lines P1 and P2 (FIG. 16, lanes 8 and 9).

Figure 17:
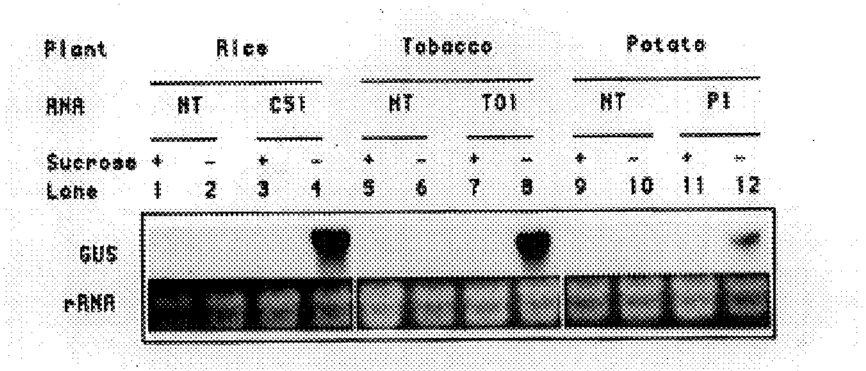
FIG. 17. Sucrose suppression of the GUS gene expression in suspension cells of transgenic plants. Suspension cells of transgenic rice cv. Tainan 5 (C51), tobacco (TO1) and potato (P1) were grown in the sucrose-containing or sucrose-free medium for 2 days. Total RNA was isolated from the suspension cells, subjected to Northern blot analysis, and hybridized with the $^{32}$P-labeled GUS DNA probe. Five μg of total RNA was loaded on each lane. The equivalence of RNA loading among lanes was demonstrated by ethidium bromide staining of rRNA. NT indicates RNA from the non-transformed control cell line.

Northern blot analysis was then performed with total RNA isolated from cultured suspension cells of each plant species using the GUS DNA as a probe (data for each of them was presented in FIG. 17). Results showed that no GUS mRNA was detectable in cells grown in medium containing sucrose (FIG. 17, lanes 3, 7 and 11), whereas GUS mRNA was abundantly accumulated in cells grown in medium lacking sucrose (FIG. 17, lanes 4, 8 and 12). No GUS mRNA was detected in the non-transformed cells either grown in the surcrose-containing or sucrose-free medium (FIG. 17, lanes 1, 2, 5, 6, 9 and 10). These results indicate that the rice α-amylase promoter is functional and regulated by sugar nutrient not only in rice cells but also in tobacco and potato cells.

Figure 18A:
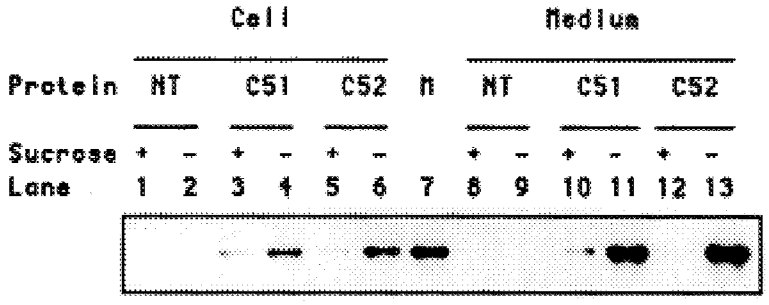
FIG. 18. Accumulation of GUS in suspension cells and culture medium of transgenic plants. Suspension cells were grown in the sucrose-containing or sucrose-free medium for 2 days. Proteins were extracted from cells or collected from the culture medium. GUS was detected by western blot analysis using the GUS antibodies. Twenty μg total cellular proteins were loaded on each lane of lanes 1–6. Five μg total protein from medium were loaded on each lane of lanes 8–13. NT indicates proteins from the non-transformed control cell line. + and − indicates presence of absence of sucrose in the medium. Panel A: Proteins from two transgenic rice (cv. Tainan 5) cell lines (C51 and C52). Lane 7 (M) contains 1 μg purified *E. coli* GUS. Panel B: Proteins from two transgenic tobacco cell lines (TO1 and TO2). Lane 7 (M) contains 400 ng purified *E. coli* GUS. Panel C: Proteins from two transgenic potato cell lines (P1 and P2). Lane 7 (M) contains 400 ng purified *E. coli* GUS.
Figure 18B:
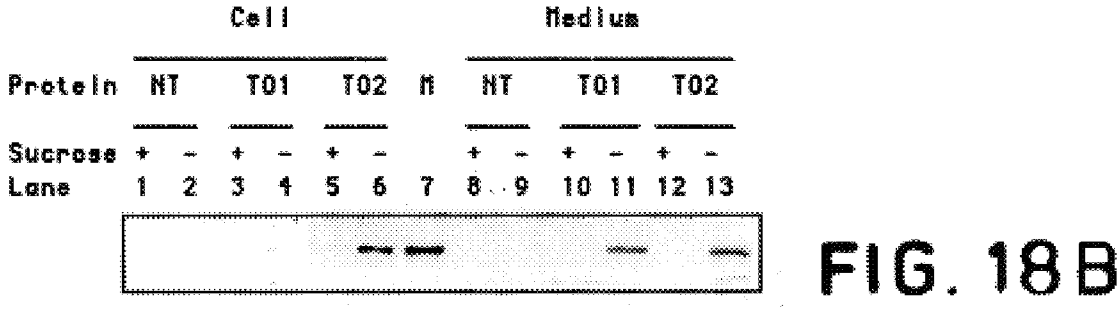
Figure 18C:
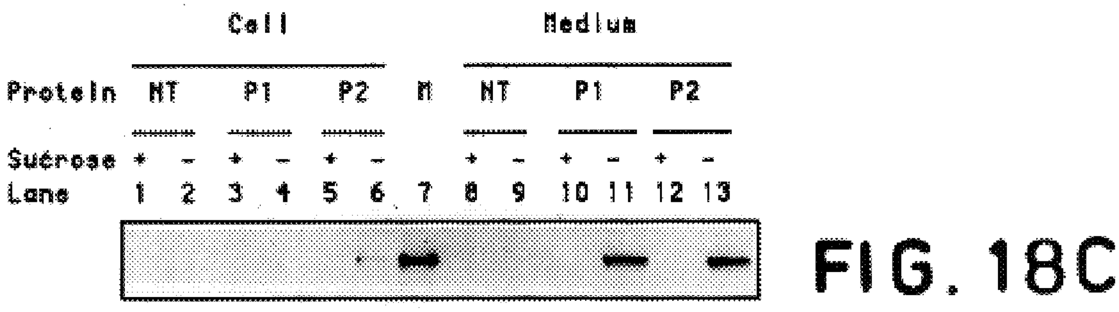

Expression of GUS protein in the suspension cells of different transgenic cell lines and in their culture media was also determined by Western blot analysis (FIG. 18). Results showed that concentrations of GUS was low in cells of transgenic rice C51 and C52 when cells were grown in medium containing sucrose (FIG. 18, panel A, lanes 3 and 5) but increased 5 to 7-fold when cells were grown in medium lacking sucrose (FIG. 18, panel A, lanes 4 and 6). Similar pattern of accumulation of GUS in the culture media was observed; concentrations of GUS in the sucrose-free medium (FIG. 18, panel A, lanes 11 and 13) were 15 to 20 times greater than those in the sucrose-containing medium (FIG. 18, panel A, lanes 10 and 12). Expression of GUS in transgenic tobacco (FIG. 18, panel B) and potato (FIG. 18, panel C) were similar as in transgenic rice. The quantity of GUS accumulated in cells or medium under sucrose starvation varied between different transgenic cell lines or plant species. No GUS was detected in cells or media of all the non-transformed cells (lanes 1, 2, 8 and 9 of panels A–C of FIG. 18).

II. ER Targeting and Glycosylation of GUS in Transgenic Plants

Figure 19A:
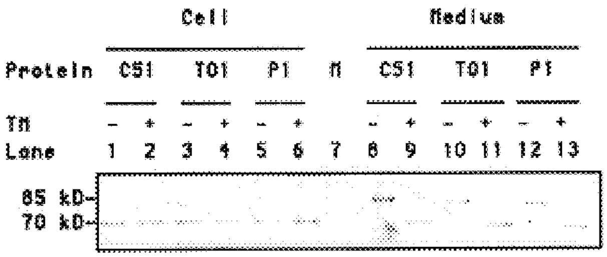
FIGS. 19A, 19B and 19C show analysis of αAmy8/GUS fusion protein in suspension cells treated with TM. Suspension cells of transgenic rice (C51), tobacco (TO1) and potato (P1) were grown in sucrose-free medium containing 10 μg/ml TM for 24 hr. The control cells were grown in sucrose-free medium containing equivalent volume of solvent used for dissolving TM. Proteins were extracted from cells or collected from the culture medium. (A) Western blot analysis of GUS using the GUS antibodies, wherein a 8–15% gradient gel is employed. Twenty μg total proteins from cells were loaded on each lane of lanes 1–6. Five μg total proteins from medium were loaded on each lane of lanes 8–13. Lane 7 (M) contains 200 ng purified *E. coli* GUS. + and − indicate presence or absence of TM in medium. (B) and (C) represent assay of GUS-activity in tobacco (TO1) and rice (C51), respectively.

Two potential sites for N-linked glycosylation (Kornfeld and Kornfeld, Annu. Rev. Biochem., 54: 631–664, 1985) are present in the deduced amino acid sequence of *E. coli* GUS (Jefferson et al., Proc. Natl. Acad. Sci. USA, 83: 8447–8451, 1986). Target of GUS to Endoplasmic Reticulum (ER) of transgenic tobacco cells resulting in glycosylation of GUS have been reported (Iturriaga et al., Plant Cell, 1: 381–390, 1989; Denecke et al., Plant Cell, 2: 51–59, 1990; Pang et al., Gene, 112: 229–234, 1992). To determine whether the signal peptide sequence of αAmy8 could target GUS to the ER and within which the N-linked glycosylation of GUS could occur, proteins were extracted from suspension cells of the transgenic cell lines or collected from their culture media and subjected to Western blot analysis (FIG. 19A). GUS present in the cell extract of transgenic rice, tobacco and potato (FIG. 19A, lanes 1, 3 and 5) was detected to have molecular mass of 70 kD, which was identical to that of the purified native GUS from *E. coli* (FIG. 19A, lane 7). On the other hand, GUS collected from the culture medium of these cells (FIG. 19A, lanes 8, 10 and 12) was found to have molecular mass of 85 kD. The increase of molecular mass of the secreted GUS was probably due to the addition of oligosaccharides by Oligosaccharide transferase which is found on the lumenal side of the ER (Hirschberg and Snider, Annu. Rev. Biochem., 56: 63–87, 1987).

Tunicamycin (TM) is known to inhibit the transfer of oligosaccharide side chain to the NXS/T residues of proteins by oligosaccharide transferase in the lumen of the ER (Elbein, Annu. Rev. Biochem., 56: 1987). Treating cells with TM should block the glycosylation of GUS and consequently decrease the molecular mass of the secreted GUS. Such a possibility was examined by treating the suspension cells of the present transgenic cell lines with 10 $\mu$g/ml TM for 24 h. Proteins were then extracted from the treated cells or collected from their culture media and analyzed. Results showed that molecular mass of GUS remained as 70 kD in the cell extract of the present transgenic rice, tobacco, and potato (FIG. 19A, lanes 2, 4 and 6), whereas the molecular mass of GUS collected from medium was reduced from 85 to 70 kD after TM treatment of these cells (FIG. 19A, lanes 9, 11 and 13). These results indicate that GUS fused to the signal peptide sequence of αAMY8 could be transported to the ER, glycosylated in the lumen of the ER, and secreted outsides the cells.

Figure 19B:
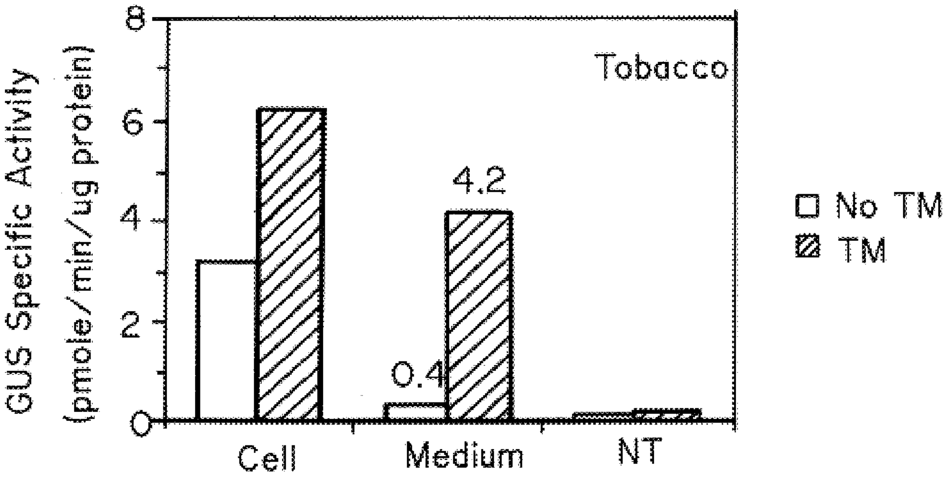
Figure 19C:
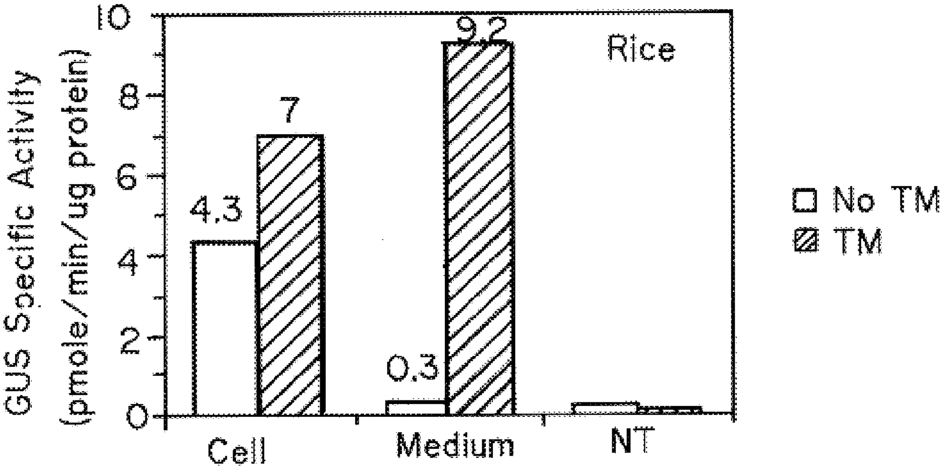

It has been reported that glycosylation of GUS inhibits the enzyme's catalytic activity and TM treatment allows the synthesis of active GUS in transgenic tobacco (Iturriaga et al. (1989), supra; Pang et al. (1992), supra). To understand whether same phenomenon also occurs in rice as well as in tobacco, the GUS activity in the aforementioned TM-treated cells or their culture media was determined. With reference to FIG. 19B, the GUS activity in the suspension cells of tobacco was increased 2-fold after TM treatment, whereas the GUS activity in the culture media thereof was increased 10-fold after TM treatment. Effect of TM treatment on the GUS activity was even more striking for rice cells. It is noted that the GUS activity in the suspension cells of rice was increased 1.6-fold after TM treatment, while the activity in the culture medium was increased 30-fold after TM treatment (FIG. 19C). The GUS activity was at background level in the non-transformed cells or their culture medium. These experiments suggested that the low activity of GUS in medium was due to glycosylation of the protein and the secreted GUS could be active if it was not glycosylated. In addition, glycosylation and inactivation of GUS also occured in the ER of rice cells.

III. Potentiality as a Secreted Protein Expression System

The observation that active GUS is formed after TM treatment means that GUS has been assembled into an active tetramer in the lumen of the ER. This is critical because several important foreign proteins that are currently being expressed in plants need to be modified and assembled into active molecules in the ER. The observed results indicate that the signal peptide of αAmy8 will be useful for obtaining active translocated proteins. To evaluate the potential as a secreted protein expression system, the efficiency of GUS secretion from the cultured cells of different plant species was determined and compared. Total proteins were collected from the culture medium and subjected to Western blot analysis (data not shown). Different amount of the purified *E. coli* GUS was used as standard for estimating the yield of GUS secreted by different transgenic cell lines and the results were summarized in Table 4.

The percentage of GUS in total proteins collected from the culture medium ranged from 10 to 40%. The yield of GUS varied between different transgenic cell lines of the same plant species as well as among different plant species. The yield was highest for rice cv. Tainan 5 (ca. 303–370 μg/g of cells) and was lowest for potato (ca. 30–33 μg/g of cells). The yield for rice cv. Tainung 62 (ca. 135–150 μg/g of cells) was similar to that for tobacco (ca. 150–163 μg/g of cells). The order of yield in these transgenic cell lines is as follows:

rice (Tainan 5)>rice (Tainung 62)>tobacco>potato.

These results suggest that the promoter and signal peptide sequence of αAmy8 can be used for developing a protein expression system for expression and secretion of foreign proteins in different plant cell cultures. However, different plant species and/or different transgenic cell lines could be different in efficiency for the expression and secretion of foreign proteins.

Discussion

The obtained experimental results demonstrates that the expression of the αAmy8/GUS chimeric gene is similarly regulated in transgenic potato and tobacco, indicating that the regulatory sequences in the rice α-amylase promoter can be identified in these two plant species. It also suggests that the pathway for transducing signals of sugar starvation and the regulatory mechanism of sugar suppression on the α-amylase promoter are conserved and retain common features between the monocots and the dicots during the divergence of the two angiosperm lines.

The inducibility of α-amylase promoter in cultured cells by sugar starvation makes it potentially useful for the design of inducible gene expression systems for transfected genes. An ideal promoter for conditional expression of genes in plant should fulfill several criteria: 1) a low level of expression under the uninduced condition, 2) a high level of expression under the induced condition, 3) induction that is readily reversible, 4) proper regulation in a number of heterologous system. Here the present invention shows that very low level of the αAmy8/GUS expression occurs when cells are grown in medium containing sucrose, however, high level of expression can be achieved after cells are incubated in medium lacking sucrose (FIGS. 17 and 18). It is therefore possible that the induction or suppression of the α-amylase promotor can be readily reversed by manipulation of sugar level in the medium. In addition, as mentioned above, the rice α-amylase promoter can be expressed and likely regulated in rice, tobacco and potato, and probably in most of plant species. Therefore, the present rice α-amylase promoter seems to satisfy all these criteria and can be used for establishing an inducible expression system in tissue cultures. Such an expression system offers opportunities not only to study the physiological functions of certain gene products but also to control important steps in plant metabolism and development.

The 1.2-kb 5' region of αAmy8 contains a putative 25-amino-acid signal peptide sequence (see SEQ. ID. NO:5 and SEQ. ID. NO:6) which is shown to facilitate targeting of GUS outside the transgenic rice, tobacco or potato cells. Evidence for translocation of GUS to the cell membrane via the ER of the plant cells is based on the observation that cells transformed with the αAmy8/GUS chimeric gene secreted an 85 kD GUS into the culture medium (FIG. 19A) and activity of the secreted GUS was significantly reduced (FIGS. 19B and 19C). Treatment of these cells with TM caused a decrease of molecular mass (70 kD) (FIG. 19A) and increase of activity of GUS secreted into the culture medium (FIGS. 19B and 19C), suggesting that GUS is transported to the ER, glycosylated in the lumen of the ER, and secreted outside the cells. Therefore, the signal peptide sequence of αAmy8 allows secretion of the expressed passenger proteins which need to be modified and assembled into active molecules in the ER. The GUS activity in the suspension cells of tobacco or rice was slightly increased (FIGS. 19B and 19C), indicating that some intracellular GUS was glycosylated, however, which was not detectable by the Western blot analysis (FIG. 19A). Alternatively, the TM treatment may somehow stabilize the intracellular GUS.

In conclusion, the experiments described above demonstrate that expression of the rice α-amylase promoter/GUS reporter gene in different species of transgenic plants can be controlled by sugar level in the medium, which allowing the functional analysis of promoter sequence important for response to sugar regulation. The α-amylase promoter can be engineered into an inducible expression cassette for basic studies of the cell biological effects of a given gene product by controlling the levels of expression of this transfected gene. In conjunction with the signal peptide sequence of α-amylase, this expression cassette can also be used for production of secreted recombinant proteins. This expression system offers new possibilities for basic research in plant biology as well as for large-scale production of genetic engineered proteins.

EXAMPLE V

Figure 20:
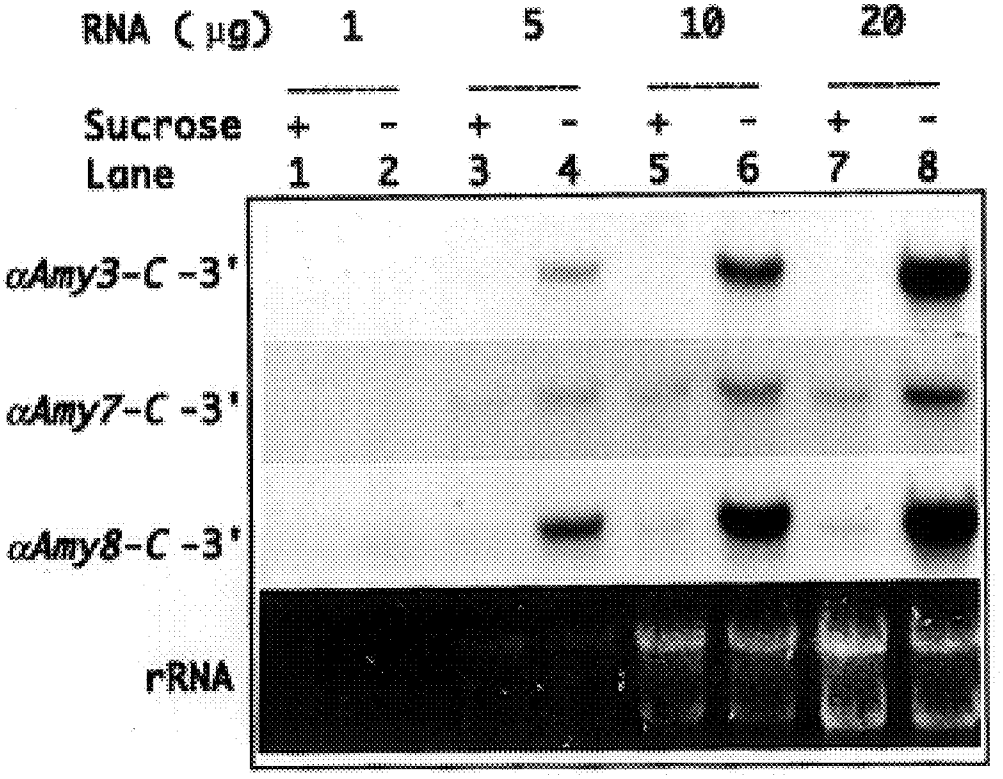
FIG. 20. Sugar suppression of α-amylase gene expression in cultured suspension cells of rice. Rice suspension cells were cultured as described previously (Yu et al (1991), supra). Suspension cells were grown in sucrose-containing medium for 5 days and transferred to sucrose-containing or sucrose-free medium for 2 days. Total RNA was isolated from the suspension cells, subjected to Northern blot analysis, and hybridized with the [α-32P]dCTP labeled α-amylase gene specific antisense RNA probes as described in Example I. The cDNA corresponding to αAmy3 was cloned from a cDNA library derived from poly($A^+$) RNA of gibberellic acid ($GA_3$)-treated rice aleurone layers using αAmy8 cDNA as a probe. Gene-specific regions among αAmy3, αAmy6, αAmy7, αAmy8, and αAmy10 were compared (FIGS. 21A and 21B). The gene-specific probes corresponding to αAmy3, αAmy7, and αAmy8 were prepared and labeled as described in Example I. The equivalence of RNA loading among lanes was demonstrated by ethidium bromide staining of rRNA. + and − indicate presence or absence of sucrose in medium. Lanes 1 and 2 each contains 1 μg RNA; lanes 3 and 4 each contains 5 μg RNA; lanes 5 and 6 each contains 10 μg RNA; lanes 7 and 8 each contains 20 μg RNA.

Basically following the experimental procedures detailed in Example I (also see Yu et al., Gene, 122: 247–253, 1992), our research team has successfully obtained a fifth rice α-amylase cDNA clone, which is named αAmy3, from a cDNA library derived from poly ($A^+$) RNA of gibberellic acid ($GA_3$)-treated rice aleurone layers using αAmy8 as a probe. The initial experiments were conducted with a gene-specific probe corresponding to the newly cloned and isolated αAmy3 cDNA to study the expression of the αAmy3 gene in rice cells. It was found that expression of the αAmy3 gene exhibits a metabolite repression in the same manner as previously reported for αAmy6, αAmy7 αAmy8 and αAmy10. FIG. 20 summarizes the currently collected data.

Comparative data regarding the nucleotide sequences of the 3 regions of these five rice α-amylase cDNA clones is given in the annexed FIG. 21. The DNA and deduced amino acid sequences of αAmy3 are respectively set out in SEQ. ID. NO's: 8 and 9.

Since it has been found to date that expression of at least five α-amylase genes are regulated by carbohydrates and it has not yet been found that expression of any α-amylase gene whose expression is not regulated by carbohydrates, we believe that most, if not all, of the α-amylase genes are regulated by carbohydrates and, as a consequence, a promoter region derived from most, if not all, α-amylase genes is useful for the practice of the present invention.

EXAMPLE VI

The molecular mechanisms that initiate and control the metabolic activities of seed germination are largely unknown. Sugars may play important roles in regulating such metabolic activities in addition to providing an essential carbon source for the growth of young seedlings and maintaining turgor pressure for the expansion of tissues during germination. To test this hypothesis, the physiological role of sugars in the regulation of α-amylase gene expression and carbohydrate metabolism in embryo and endosperm of germinating rice seeds is investigated. RNA blot analysis revealed that in the embryo and aleurone cells, expression of four α-amylase genes was differentially regulated by sugars via mechanisms beyond the well-known hormonal control mechanism. In the aleurone cells, expression of these α-amylase genes was regulated by gibberellins produced in the embryo and by osmotically active sugars. In the embryo, expression of two α-amylase genes and production of gibberellins were transient, and were probably induced by depletion of sugars in the embryo endosperm as germination proceeded. The differential expression of the four α-amylase genes in the embryo and aleurone cells was probably due to their markedly different sensitivities to changes in tissue sugar levels. This study supports a model in which sugars regulate the expression of α-amylase genes in a tissue-specific manner: via a feedback control mechanism in the embryo and via an osmotic control mechanism in the aleurone cells. An interactive loop among sugars, gibberellins, and α-amylase genes in the germinating cereal grain is presented based on the experimental results gathered from the present example.

Specifically, sugars are important in regulating the expression of various genes in diverse organisms. In higher plants, sugar regulation of gene expression provides a mechanism for interactions between source and sink for carbohydrate allocation and utilization. Sugars upregulate the expression of genes in connection with storage processes in potato (Rocha-Sosa et al., EMBO J. 8: 23–29, 1989; Salanoubat and Belliard, Gene 84: 181–185, 1989; MÜller-Rober et al., Mol. Gen. Genet. 224: 136–146, 1990), sweet potato (Hattori et al., Plant Mol. Biol. 14: 595–604, 1990; Nakamura et al., Plant Physiol. 43: 1898–1905, 1991), and maize (Koch et al., Plant Cell 4: 59–69, 1992).

On the other hand, sugar metabolites can feedback regulate the expression of enzymes involved in carbohydrate metabolism (J. Sheen, Photosysth. Res. 39: 427–438, 1994). For example, expression of seven maize photosynthetic genes (J. Sheen, Plant Cell 2: 1027–1038, 1990) and tobacco chlorophyll a/b binding protein and Rubisco small subunit genes (Criqui et al., Plant Physiol. Biochem. 30: 597–601, 1992) in mesophyll protoplasts is repressed by the photosynthetic end-products sucrose and glucose.

Previously, It has been found that the expression of α-amylase genes in cultured rice suspension cells is repressed by sugars in the medium (Yu et al. (1991), supra). Recently, phosphorylation of hexose sugars by hexokinase has been proposed to act as a key signal transmitter in initiating the sugar repression responses of photosynthetic genes (Jang and Sheen, Plant Cell 6: 1665–1679, 1994) and malate synthase and isocitrate lyase genes involved in the glyoxylate cycle (Graham et al., Plant Cell 6: 761–772, 1994).

The amylolytic breakdown of stored starch is one of the central biochemical events in the germination of cereal grains. The principle enzymes involved in this breakdown are α-amylases which hydrolyze α-1,4 linked a glucose polymers and release fragments that can be further broken down by other amylolytic enzymes (Sun and Henson, Arch. Biochem. Biophys. 284: 298–305, 1991). Studies of α-amylases have mostly focused on the hormonal regulation of their synthesis and secretion in the endosperms of germinating cereal grains. In these tissues gibberellic acid ($GA_3$, one of the gibberellins) stimulates and abscisic acid (ABA) represses α-amylase gene expression.

Previously, it has been found that the expression of several α-amylase genes in rice is under two different modes of tissue-dependent regulation; the genes are activated by hormones in the aleurone of germinating seeds and suppressed by sugars in cultured suspension cells (Yu et al., 1991, 1992, supra). Later, expression of one α-amylase gene in the embryo of germinating rice seed was also reported to be suppressed by sugars (Karrer and Rodriguez, Plant J. 2: 517–523, 1992). In cultured rice suspension cells, α-amylase expression, carbohydrate metabolism, and vacuolar autophagy are coordinately regulated by sugar nutrients in the medium (Chen et al., Plant J. 6: 625–636, 1994). Both the transcription rate and mRNA stability of α-amylase genes in cultured cells increase in response to sucrose depletion in the culture medium (Sheu et al., Plant J. 5: 655–664, 1994). Use of transgenic rice carrying an α-amylase gene promoter/reporter gene further proved that the regulation of α-amylase gene expression by sugars involves a transcriptional control mechanism (see Examples II and IV, also Chan et al., Plant Mol. Biol. 22: 491–506, 1993, J. Biol. Chem. 269: 17635–17641, 1994; Huang et al., Plant Mol. Biol. 23: 737–747, 1993).

To date, little is known of the molecular mechanisms that initiate and control the metabolic activities of seeds, particularly in the embryo, following uptake of water. The reserves used to support the growth and development of the embryo and seedling during germination of maize kernel is initially drawn from the embryo itself, and later from the starchy endosperm. Studies on the physiological role of sugars in the regulation of α-amylase gene expression and carbohydrate metabolism in embryo and endosperm of germinating cereal grains may ultimately lead us to a better understanding of the molecular mechanisms controlling germination of higher plants. Here, it is demonstrated that the expression of various members of the rice α-amylase gene family is differentially regulated by sugar levels in a tissue-specific manner, and propose that repression of α-amylase gene expression and gibberellin production in embryos by low concentrations of glucose operates via a feedback control mechanism. In contrast, repression of α-amylase gene expression in aleurone cells by higher concentrations of glucose operates via an osmotic regulatory mechanism.

A. Methods

I. Plant Materials

The rice variety used for germination was *Oryza sativa* L. cv. Taipei 309. Intact embryos were mechanically isolated from dehulled seeds and examined by light microscopy to verify the presence of intact scutellum. The isolated embryos or intact dehulled seeds were sterilized with 1% NaOCl and 2 drops of Tween-20 for 20 and 30 min, respectively, washed extensively with sterile distilled water, and placed on two pieces of sterile Whatman No. 1 filter papers within a petri dish. Ten ml of sterile water was applied to the filter papers to imbibe the embryos or seeds. The petri dishes were placed in an incubator incubated at 27° C. in the dark for various lengths of time. Seedlings were removed at various time points and the shoots, roots, embryos containing scutella, and endosperms were separated by dissection. The aleurone layers were peeled off from the starchy endosperms. The various collected plant materials were inmediately frozen in liquid N2 and stored at −70° C. until use.

II. Plasmids

Plasmids αAmy3-C, αAmy6-C, αAmy7-C, and αAmy8-C carry four different rice α-amylase cDNA in pBluescript $KS^+$ (Stratagene) (see Example I). Plasmid pcRAc.1.3 containing a rice actin cDNA insert in pBluescriptII-KS (McElroy et al., Plant Mol. Biol. 14: 163–171, 1990) was kindly provided by Dr. Ray Wu (Cornell University, Ithaca).

III. RNA Gel Blot Analysis

Total RNA was purified from cultured cells by the method of Verwoerd et al. (Nucl. Acids Res. 17: 2362, 1989). RNA blot analysis was performed as described by Chao et al. (J. Virol. 66: 1442–1448, 1992). The 1.4-kb αAmy8-C and pcRAc1.3 cDNA inserts used as probes were excised from the plasmid vectors by restriction enzyme EcoRI and labelled with [$\alpha$-$^{32}$P]dCTP using the random primer method (Feinberg and Vogelstein, Anal. Biochem. 132: 6–13, 1983). Probe αAmy8-C containing the coding region of αAmy8 will hybridize to mRNA of all α-amylase genes. The four α-amylase gene-specific probes were prepared from αAmy3-C, αAmy6-C, αAmy7-C, and αAmy8-C and labeled as anti-sense RNA probes as described in Example I. In each experiment the hybridized probes on the Gene-Screen (DuPont) membrane were stripped off by incubating twice (30 min each) in washing solution containing 0.1×SSC and 0.1% SDS at 90° C. The membrane was re-hybridized with different α-amylase gene-specific probes and the actin cDNA probe. The equivalence of RNA loading among lanes in each experiment was demonstrated by ethidium bromide staining of rRNA.

IV. Bioassay for Gibberellins

The method used for determination of gibberellin levels was a modified nondwarf rice seedling bioassay method (Nishijima et al., Plant Physiol. 98: 962–965, 1992). Rice seeds (*Oryza sativa* L. cv. Taipei 309) were sterilized with 1% NaOCl for 15 min, washed extensively with distilled water, and soaked in water containing 80 μM uniconazole [S-3307, (±)-(E)-1-(4-chlorophenyl)-4,4-dimethyl-2-(1,2,4-triazole-1-yl)-1-penten-3-ol, AGROS Co., Osaka City, Osaka, Japan) at 26° C. in the dark for 48 h.

The seeds were then washed with water and incubated in water under the same growth conditions. When the coleoptiles were 2 to 5 mm in length, 20 germinated. seeds were planted in a vial (28 mm in diameter×58 mm in height) which contained 30 ml of 0.8% (w/v) agar. Ten μl of the embryo gibberellin extracts (see below) were applied with a microsyringe to the region between the coleoptile and the first leaf of a seedling. The germinating seeds were then incubated at 26° C. under 16/8 h irradiation. Three days later, the length of the second leaf sheath was measured.

For preparation of gibberellin extracts from embryos, rice seeds were sterilized and placed on filter papers within petri dishes. Five ml of water or glucose solution was applied to the filter papers and seeds were germinated for various lengths of time. Embryos were separated from endosperms and stored at −70° C. until extraction. Twenty embryos from each time point were grounded in liquid N2 with mortar and pestle and gibberellins in the embryos were extracted with 200 μl solution containing 50% aqueous acetone and 50% TBS buffer (each liter contains 800 mg Tris, 20 mg $MgCl_2$.6H2O, 60 mg NaCl, and 10 mg $NaN_3$). The gibberellin extracts were clarified by centrifugation at 14000×g for 5 min at 4° C. and ready for use.

Results

I. Differential Expression of α-Amylase Genes in Various Tissues of Germinating Seed The expression of individual α-amylase genes in various tissues of germinating rice seeds was analyzed. Four α-amylase gene-specific probes corresponding to αAmy3, αAmy6, αAmy7, and αAmy8 were used for RNA gel blot analysis of RNA purified from aleurone cells, embryos, shoots, and roots during a 9-day period of seed germination. The amount of mRNA shown in the RNA gel blot analysis was quantified densitometrically as well. In the aleurone cells, RNA gel blots (FIG. 22A) and quantitation of mRNA concentrations (FIG. 22B) show that mRNA levels of the four α-amylase genes fluctuated during germination. The mRNA levels of αAmy3, αAmy6, and αAmy8 reached their first peaks at day 5, declined significantly at day 6, then rose again and reached their second peaks at day 8. The expression pattern for αAmy7 was somewhat different; its mRNA level remained at a plateau between day 5 and day 7, then increased and reached its only peak at day 8.

After imbibition of rice seeds with water, the shoots and roots emerged from the embryos and became distinct at day 2. Growth continued until the germination was terminated at day 9. The scutellar epithelium of embryo is the initial and major site of α-amylase gene expression in the germinating rice grains (Ranjhan et al., Plant Cell Physiol. 33: 73–79, 1992). To avoid dilution of α-amylase mEUfA in the embryos by the large amounts of mRNA synthesized in the growing shoots and roots, we removed the shoots and roots from the germinating embryos beginning at day 2 before purification of mRNA. Total RNA was purified from the embryos (including epithelium but lacking shoots and roots) and subjected to RNA gel blot analysis. The RNA gel blots (FIG. 23A) and quantitation of mRNA concentrations (FIG. 23B) show that the temporal expression patterns of different α-amylase genes in the germinating embryos varied. Accumulation of αAmy3, αAmy7, and αAmy8 mRNA was detectable as early as 12 h after the beginning of germination. The levels of αAmy3 and αAmy8 mRNA reached their peaks at day 1, declined rapidly at day 2, and remained at low levels throughout the rest of incubation time. The levels of αAmy6 mRNA were high between day 1 and day 3, declined at day 4, and increased again afterwards. In contrast, the level of αAmy7 mRNA started off low then increased with incubation time. Levels of the actin mRNA were high only between 12 hr and 3 days after germination. Thus quantitation of the amount of α-amylase mRNA was not normalized to the amount of actin mRNA.

Expression of α-amylase genes in the excised shoots and roots between days 2 and 9 after seed germination was also analyzed by RNA gel blot analysis. Accumulation of total α-amylase mRNA was either low or undetectable in both shoots and roots (data not shown), so expression of individual α-amylase genes was not further studied.

Figure 23A:
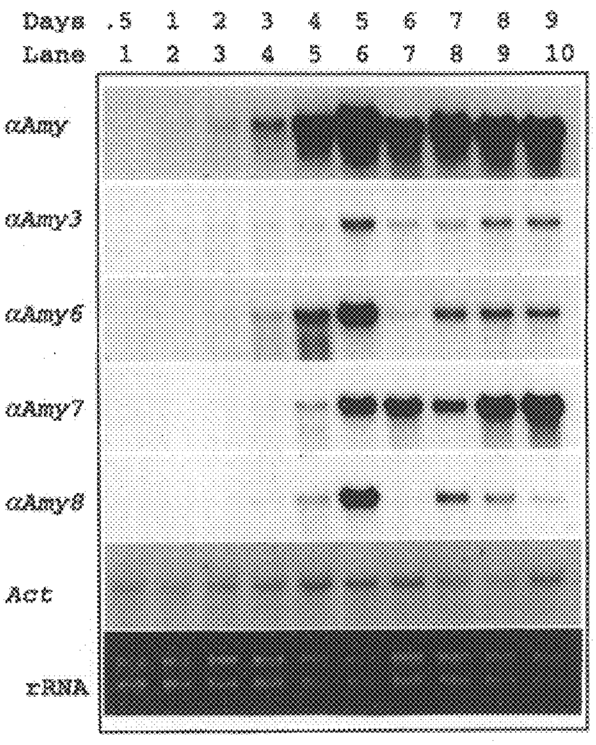
FIGS. 23A and 23B are RNA gel blot analysis showing time course of expression of α-amylase genes in embryo of germinating rice seed. The embryos of seeds germinated in experiment of FIGS. 22A and 22B were collected and total RNA was purified. RNA was subjected to RNA gel blot analysis using the same probes as in FIGS. 22A and 22B. Ten μg of total RNA was loaded in each lane. Denomination of gene names is as described in the legend of FIG. 22A.
Figure 23B:
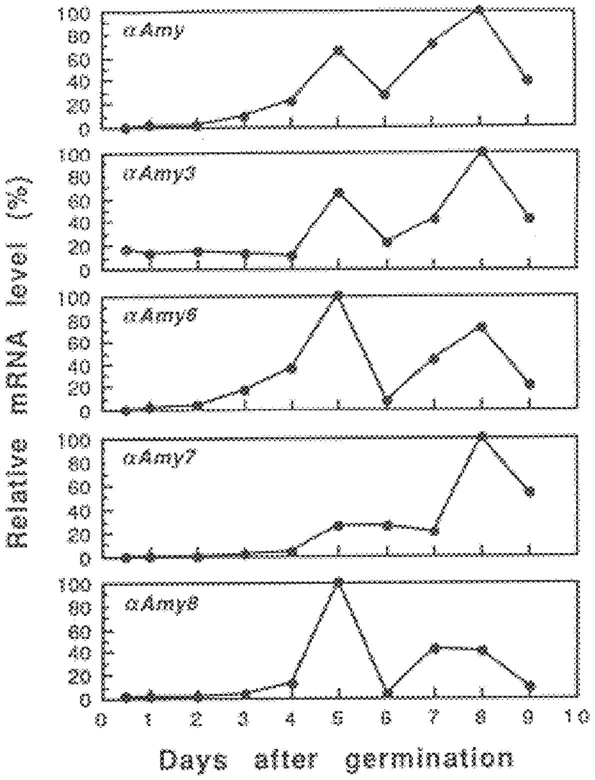

II. Suppression of αAmy3 and αAmy8 Expression Occurs When Sugar Levels in the Germinating Embryos Increase FIG. 23A shows that in the germinating embryo, αAmy3 and αAmy8 were expressed mainly at day 1 and this expression declined rapidly at day 2 after germination. The suppression of αAmy3 and αAmy8 expression in the germinating embryo might be due to increased amounts of hydrolysis products of starch being transported from the endosperm to the embryo during germination.

Figure 24A:
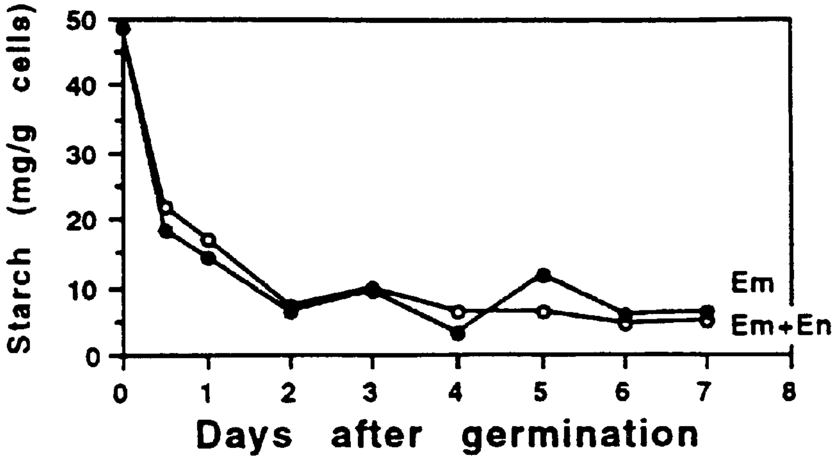
FIG. 24 shows measurement of soluble sugar and starch contents in embryo and endosperm during the time course of germination. Intact seeds or isolated embryos were germinated in water for various lengths of time. Embryos and endosperms were separated from intact seeds after germination. Starch and soluble sugar contents of the embryos of intact seeds (Em+En), isolated embryos (Em), or endosperms were determined using a method described in Example IV. Fifty intact seeds, isolated embryos, or endosperms were used for each time point and the experiment was done in triplicate. Panel (A) Starch content in embryos. Panel (B) Soluble sugar content in embryos. Panel (C) Soluble sugar contents (O—O) and fresh weight of endosperms (O—O).
Figure 24B:
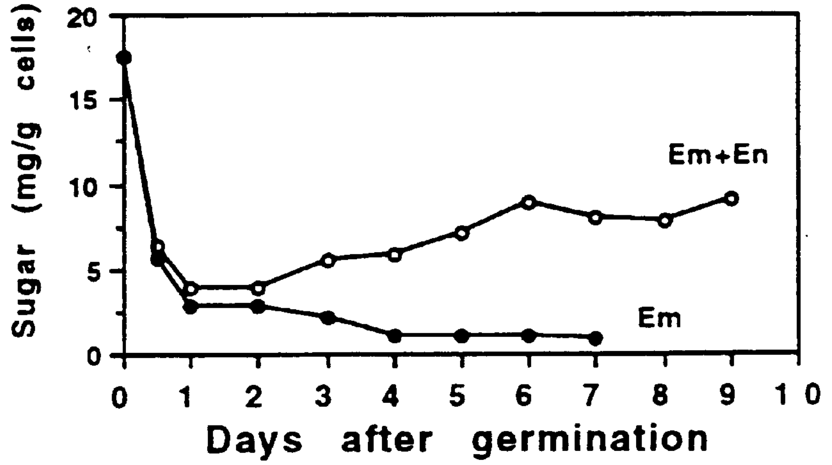
Figure 24C:
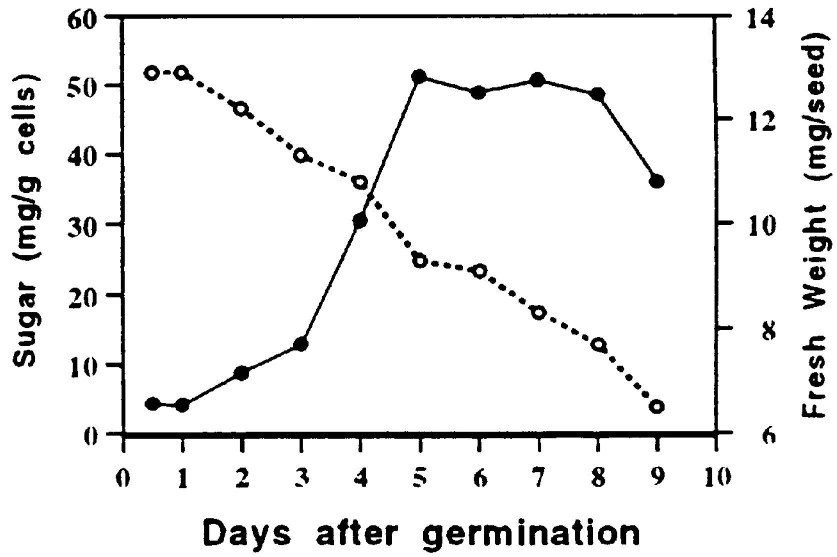

To test this possibility, sugar concentration in the embryo during germination was analyzed. Embryos of intact seeds (Em+En) or embryos isolated from dry intact seeds (Em) were both germinated in water for various lengths of time, and the starch and soluble sugar levels in the germinating embryos determined (FIG. 24). Levels of both starch and sugars declined rapidly in both types of embryos. Approximately 70% of the starch disappeared during the first two days of germination and then remained at the same low level thereafter (FIG. 24, panel A). Approximately 40–50% of the soluble sugars disappeared during the first day of germination in both types of germinating embryos (FIG. 24, panel B). In the isolated embryos, the sugar level continued to decline from day 2 to day 4 but at a slower rate and only 15% of the sugars was left when the germination was terminated at day 7.

In contrast, the sugar levels of intact seed embryos began to rise after day 2 and increased with time until the germination was terminated at day 9. These results reveal that the reserved carbohydrates in the embryos were rapidly consumed by the growing seedlings, but the sugars in the embryos of intact seeds were replenished by the starch hydrolysis products transported from the endosperms during germination.

Glucose Differentially Regulates the Expression of α-Amylase Genes in Germinating Embryo To investigate the possibility that sugars transported from the endosperm were responsible for the suppression of αAmy3 and αAmy8 expression in the germinating embryo 2 days after germination (FIGS. 23A and 23B), the effect of sugar on the expression of αAmy3 and αAmy8 in the embryo was studied. Embryos were isolated from dry intact seeds and germinated in water or treated with the major end product of starch hydrolysis—glucose.

Figure 25A:
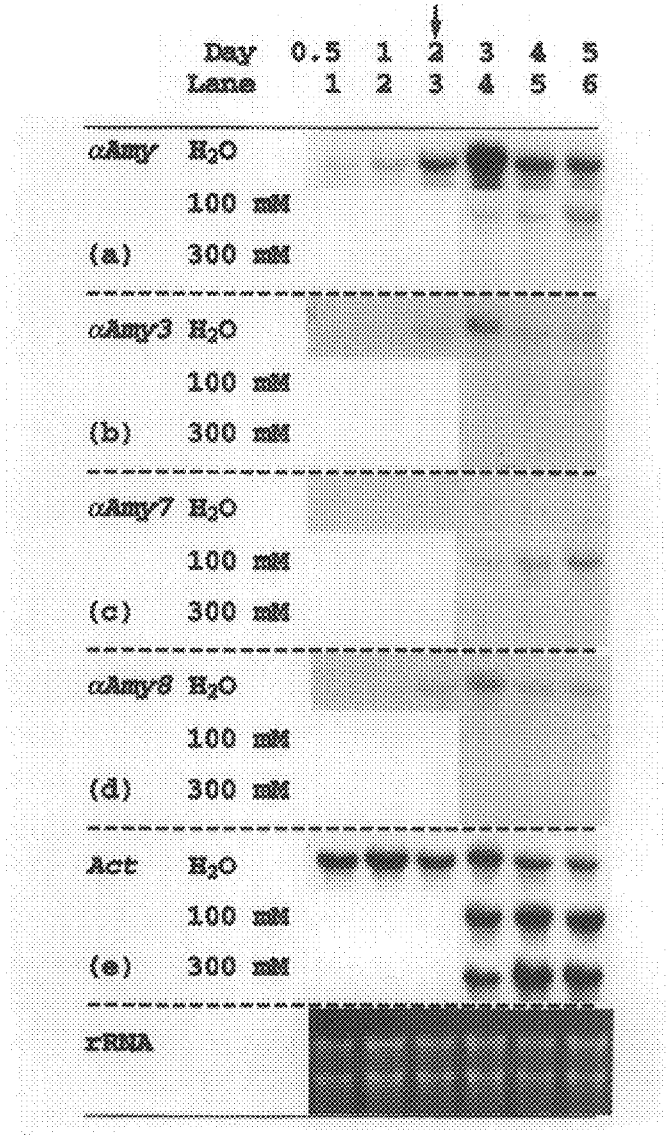
FIGS. 25A and 25B are RNA gel blot analysis showing differential suppression of α-amylase gene expression in germinating rice embryos by glucose. Isolated embryos were germinated in water for 2 days and divided into 3 groups. One group of the embryos remained in water, the other two groups were respectively incubated in high (FIG. 25A) or low (FIG. 25B) concentrations of glucose. These embryos were germinated for another 3 days. Total RNA was purified from the embryos and subjected to RNA gel blot analysis using the α-amylase genes containing coding region (αAmy8-C) or gene-specific regions as the probes. Ten μg total RNA was loaded in each lane. The arrow indicates the time point when glucose treatment was applied. Denomination of gene names is as described in the legend of FIG. 22A.

The embryos were first germinated in water for 2 days and then divided into three groups; one group remained incubating in water and the other two groups were respectively incubated in 100 and 300 mM glucose. The incubation proceeded for another 3 days. Total RNA was purified from the embryos and subjected to RNA gel blot analysis (FIG. 25A). The accumulation of total α-amylase (αAmy) mRNA in the embryos germinated in water increased with time, reached a peak at day 3, and declined at day 4 (FIG. 25A, panel a).

In contrast, the accumulation of α-amylase mRNA was significantly reduced in embryos treated with 100 mM glucose and was further reduced by 300 mM glucose. Patterns of accumulation of α-amylase mRNA corresponding to αAmy3 (FIG. 25A, panel b) and αAmy8 (FIG. 25A, panel d) were similar to that of total α-amylase mRNA.

Interestingly, accumulation of αAmy7 mRNA was not detected in embryos incubated in water. Instead, it was detected in embryos treated with 100 mM glucose (FIG. 25A, panel c). However, the expression of αAmy7 in embryos could be abolished by 300 mM glucose.

The result demonstrates that expression of αAmy3 and αAmy8 was suppressed by glucose at concentrations lower than that required for αAmy7. Accumulation of actin mRNA in embryos germinated in water was relatively constant for the first 3 days and decreased slightly after day 4 (FIG. 25A, panel e). Treatment of embryos with either 100 or 300 mM glucose resumed the accumulation of actin mRNA at day 4 and day 5.

Figure 25B:
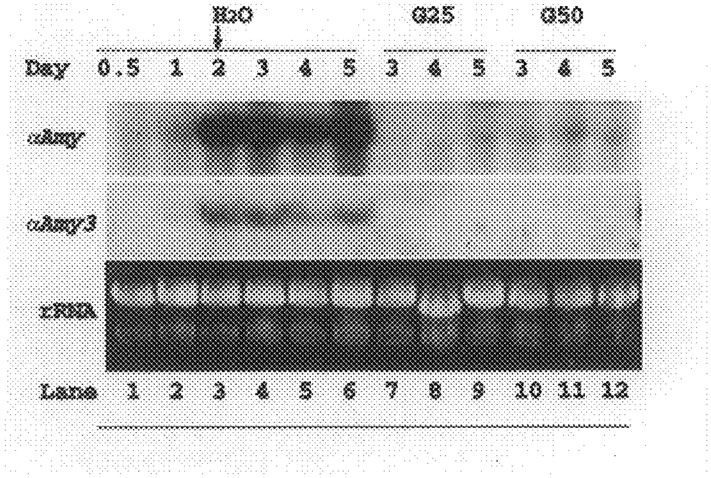

To determine whether lower concentrations of glucose could suppress the expression of α-amylase genes, similar experiment was performed except that the concentrations of glucose were reduced to 25 and 50 mM (FIG. 25B). The accumulation of total α-amylase mRNA in the embryos germinated in water increased with time (FIG. 25B, lanes 1–6). In contrast, the accumulation of α-amylase mRNA was significantly reduced in embryos treated with both 25 and 50 mM glucose (FIG. 25B, lanes 7–12). Pattern of accumulation of αAmy3 mRNA was similar to that of total α-amylase mRNA.

Figure 22A:
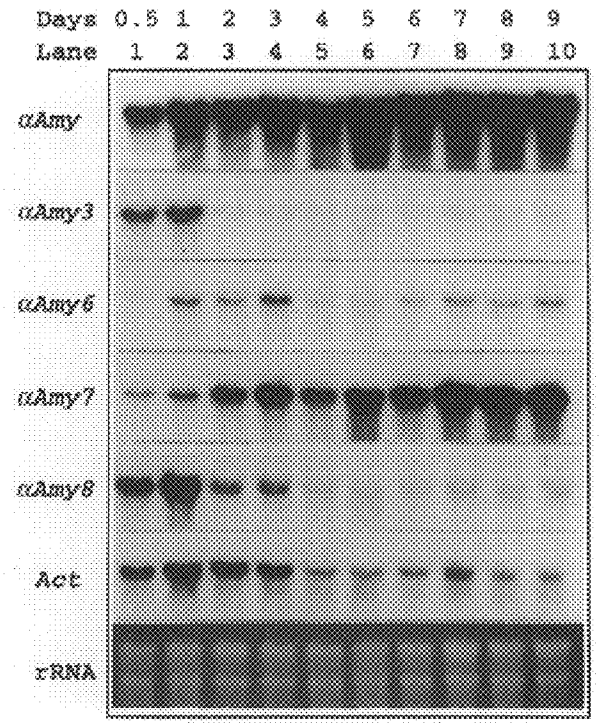
FIGS. 22A and 22B are RNA gel blot analysis showing time course of expression of α-amylase genes in aleurone cells of germinating rice seeds. Seeds were germinated for various lengths of time. Total RNA was purified from the aleurone cells and subjected to RNA gel blot analysis using the α-amylase genes containing coding region (αAmy8-C) or gene-specific regions as probes. Five μg total RNA was loaded in each lane. αAmy indicates total α-amylase mRNA; αAmy3, αAmy6, αAmy7, and αAmy8 indicates mRNA corresponding to each of the four α-amylase genes;. Act indicates total actin mRNA.
Figure 22B:
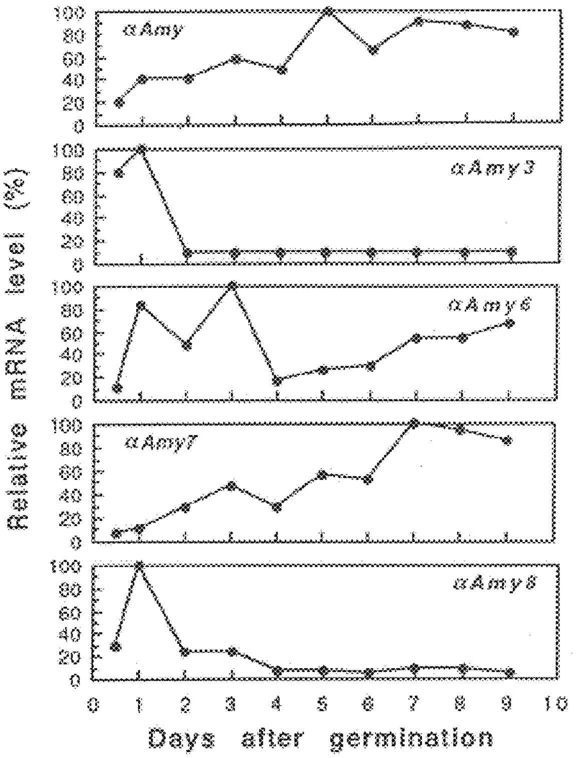

III. High Concentration of Sugars Differentially Regulates the Expression of α-Amylase Genes in Aleurone Cells FIGS. 22A and 22B show that expression of the four α-amylase genes in the aleurone cells fluctuated during the course of germination. To investigate whether the variations in α-amylase mRNA accumulation were related to the variations in sugar content in the endosperm during germination, rice seeds were germinated in water for various lengths of time and the concentration of soluble sugars in the endosperm determined. The fresh weight of the endosperm progressively decreased during germination, while levels of soluble sugars in the endosperm increased rapidly after day 3 and reached a maximum at day 5 after germination (FIG. 24, panel C). Accumulation of sugars remained maximal from days 5–8, then declined at day 9. Therefore levels of total soluble sugars in the entire endosperm remained relatively constant during the period days 5–8 even though α-amylase mRNA levels fluctuated.

To determine whether sugars were able to suppress the expression of α-amylase genes in the aleurone cells as in the embryo (FIGS. 25A and 25B), rice seeds were germinated and treated with 50 or 100 mM glucose for various lengths of time. Total RNA was purified from the aleurone cells and subjected to RNA gel blot analysis. Expression of αAmy3, αAmy7 and αAMy8 in the aleurone cells was not significantly altered by glucose at concentrations ≦100 mM (data not shown). Accumulation of high concentrations of hydrolysis products in the subaleurone space of the endosperm of germinating barley seeds has been proposed to inhibit the production of α-amylases by the aleurone layer (Jones and Armstrong, Plant Physiol. 48: 137–142, 1971). Here, it is found that the concentration of sugars which accumulated in the endosperm 5 days after germination could be higher than 500 mM (Table 6).

To test the possibility that the expression of α-amylase genes in the aleurone cells might be suppressed by a high concentration of sugars, rice seeds were germinated in high concentrations of glucose or mannitol. Rice seeds were first germinated in water for 3 days, then divided into seven groups; one group remained incubating in water, the other six groups were incubated in 300, 400, or 500 mM of glucose or mannitol. The incubation proceeded for another 3 days. Total RNA was purified from the aleurone cells and subjected to RNA gel blot analysis (FIG. 26).

Figure 26:
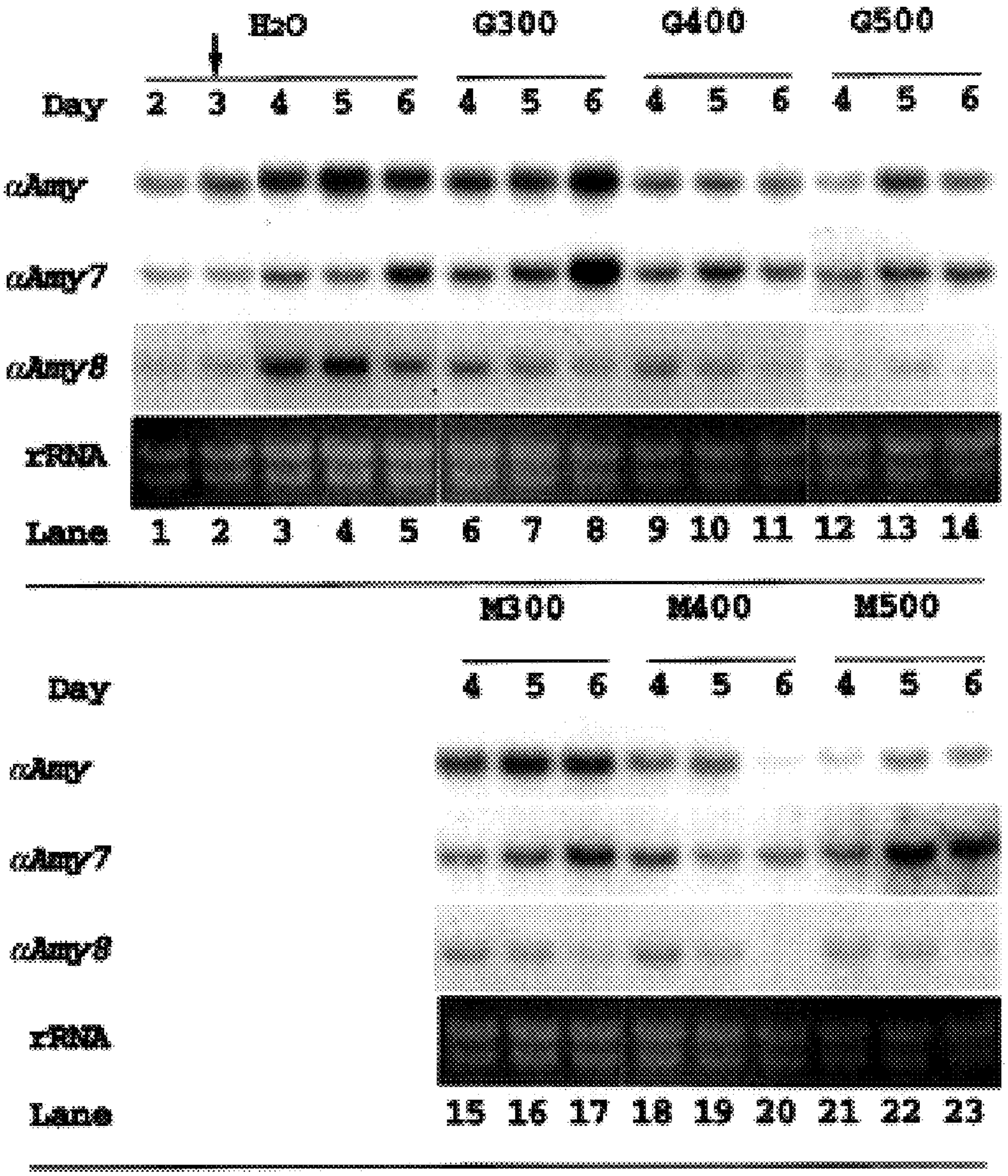
FIG. 26 is RNA gel blot analysis showing suppression of α-amylase gene expression in aleurone cells by high concentrations of glucose and mannitol. Seeds were germinated in water for 3 days, longitudinally cut half-way at endosperms from the ventral side, and divided into seven groups. One group of the germinating seeds remained in water, the other groups were incubated in 300, 400, or 500 mM of glucose (G) or mannitol (M). These seeds were then germinated for another 3 days. Total RNA was purified from the aleurone cells and RNA gel blot analysis was performed using αAmy8-C or αAmy7 and αAmy8 gene-specific DNA as the probes. Five μg total RNA was loaded in each lane. The arrow indicates the time point when glucose treatment was applied. The experiment was performed twice producing the same result.

Accumulation of total α-amylase mRNA in the aleurone cells of seeds germinated in water increased with time and peaked at day 5 (FIG. 26, lanes 1–5). The pattern was not significantly altered by 300 mM glucose (FIG. 26, lanes 6–8) or mannitol (FIG. 26, lanes 15–17). However, it was significantly reduced by glucose (FIG. 26, lanes 9–14) or mannitol (FIG. 26, lanes 18–23) at concentrations ≧400 mM. Surprisingly, different expression patterns were observed for αAmy7 and αAmy8. Glucose and mannitol at 300–500 mM did not affect the expression of αAmy7, but significantly reduced the expression of αAmy8 in aleurone cells (compare FIG. 26, lanes 6–14 and lanes 15–23 with lanes 3–5). These results suggest that expression of various α-amylase genes in the aleurone cells is subject to differential regulation by osmotically active sugars.

IV. Glucose Suppresses the Synthesis of Gibberellins in Germinating Embryo

To investigate whether sugars transported from the endosperm cause a decline in gibberellin synthesis in the embryo during germination, glucose was applied to the germinating rice seeds and gibberellins produced in the embryos were measured by a bioassay (Nishijima et al. (1992), supra). In this method, seeds of nondwarf rice cultivars (Taipei 309) were first treated with the GA-biosynthesis inhibitor uniconazole for 2 days. The seeds were then germinatnated in extracts prepared from the embryos of rice seeds germinated in 50 mM glucose or mannitol for various lengths of time.

Figure 28:
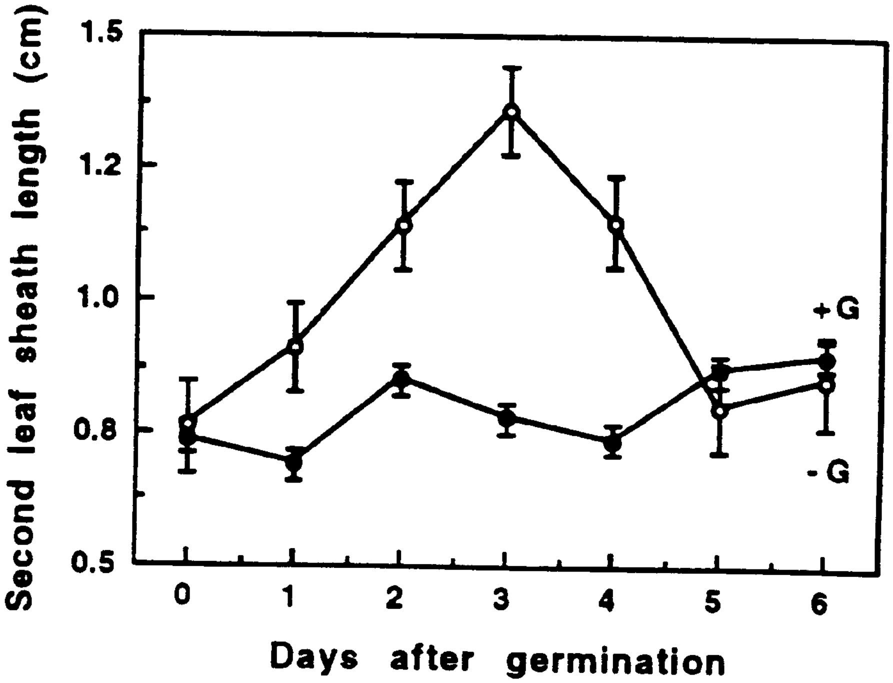
FIG. 28 shows that production of gibberellins in germinating embryos is suppressed by glucose. Seeds were germinated for various lengths of time and the level of gibberellins in embryos was determined by a bioassay using nondwarf rice seedlings as described in Methods. Levels of gibberellins in the germinating embryos are expressed as the length of the second leaf sheath of rice seedlings. +G indicates seeds germinated in the presence of 50 mM glucose. −G indicates seeds germinated in the absence of glucose but containing 50 mM mannitol.

The lengths of the second leaf sheath of the growing seedlings was measured 3 days after incubation. Results in FIG. 28 show that the accumulation of gibberellins in the embryos germinated in 50 mM mannitol increased with time, peaked at day 3, and declined thereafter. In contrast, germination of seeds in 50 mM glucose inhibited the increase-of gibberellin accumulation in embryos.

Discussion

Figure 27A:
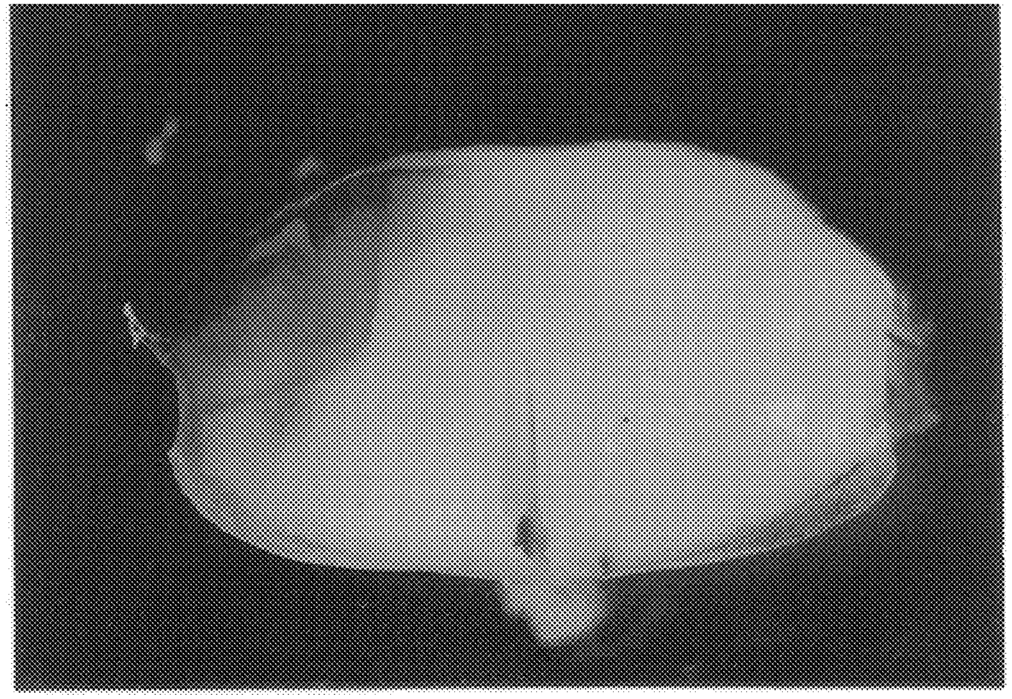
FIGS. 27A and 27B show histochemical analysis of αAmy8/GUS gene expression during germination of transgenic rice seeds. Transgenic seeds were germinated in water for 1 day (FIG. 27A) and 5 days (FIG. 27B) at room temperature, longitudinally cut in half, and stained with X-glucuronide.
Figure 27B:
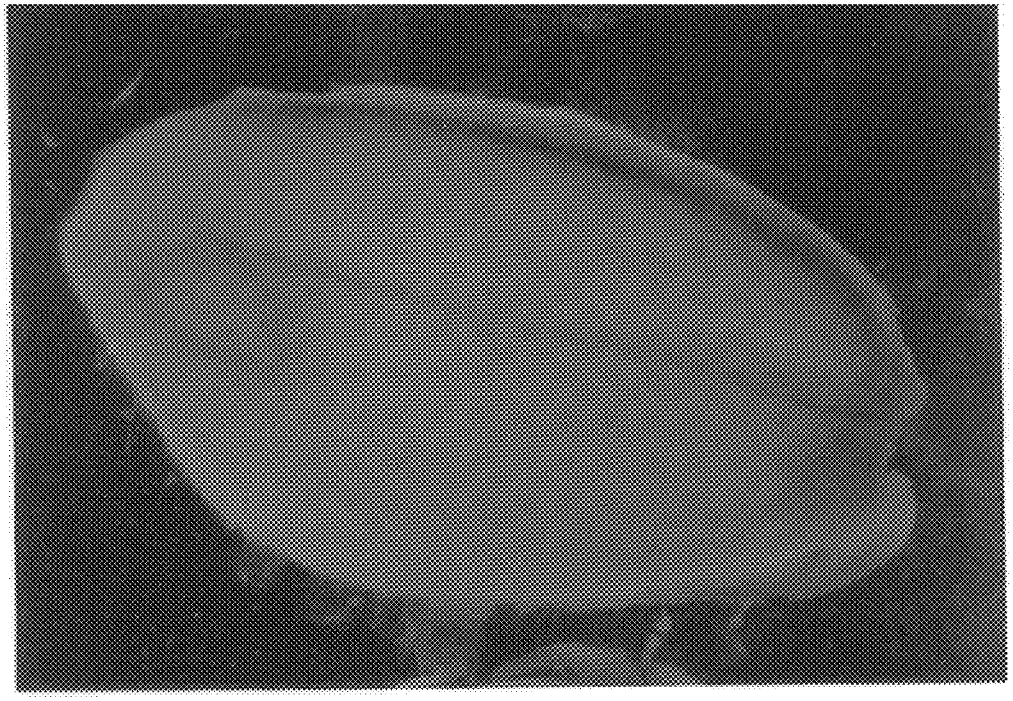

I. Both Gibberellins and Osmotically Active Sugars Regulate the Expression of α-Amylase Genes in Aleurone Cells FIGS. 27A and 27B show the histochemical analysis of αaAmy8/GUS gene expression during germination of transgenic rice seeds. Although it is generally accepted that gibberellins which diffuse from the embryo activate the expression of α-amylase genes in the aleurone layer at early stages of germination, little is known of the regulation of α-amylase gene expression in aleurone cells at later stages, or in other tissues of the germinating seed. In aleurone cells, accumulation of αAmy3, αAmy6, and αAmy8 mRNA initially increased with time, presumably induced by gibberellins produced in the embryo during germination. However, the mRNA levels of these α-amylase genes fluctuated after reaching a peak at day 5 (FIGS. 22A and 22B). The fluctuation suggests that some mechanism exists which operates to induce or suppress α-amylase gene expression, and which is controlled at the level of either transcription and/or mRNA stability.

Osmotically active solutes accumulating in the endosperm of germinating barley seeds are important factors repressing the biosynthesis of α-amylases in the aleurone layer (Jones and Armstrong (1971), supra). Since the concentration of soluble sugars in the endosperm reached 50 mg/g (approximately 550 mM) 5 days after germination (panel C of FIG. 24 and Table 5) and the expression of αAmy8 in the aleurone layer could be suppressed by high concentrations ($\geq$300 mM) of glucose and mannitol (FIG. 26), we hypothesize that the levels of α-amylase mRNA fluctuated in response to the transient rise and fall of the levels of hydrolysis products in the subaleurone space. According to this hypothesis, synthesis of α-amylases in the aleurone would initially increase in response to gibberellins, and subsequent secretion of α-amylases into the starchy endosperm would lead to hydrolysis of starch adjacent to the aleurone cells.

The hydrolysis products might therefore accumulate in the subaleurone space of the endosperm to levels high enough to exert osmotic stress and suppress the production of α-amylases. However, subsequent withdrawal and adsorption of hydrolysis products by the scutellum due to rapid seedling growth would cause a drop in the level of osmotically active solutes in the subaleurone space, which in turn would release the suppression of α-amylase gene expression. Therefore, both gibberellins and osmotically active sugars would regulate the expression of α-amylase genes in the aleurone cells.

The transient rise and fall of soluble sugars in the endosperm was not detected between day 5 and day 9 after germination (FIG. 24, panel C). The reason may be that the local concentrations of soluble sugars in the subaleurone space rose and fell but were not detected due to the use of whole endosperm extracts for sugar determination. Fluctuation in α-amylase mRNA levels could have resulted from an opposing interaction between gibberellins and osmotically active solutes during the course of germination. Alternatively, gibberellins and osmotically active solutes might regulate the expression of α-amylase genes at different stages during germination.

In the latter hypothesis, gibberellins would serve as important signals in activating the expression of α-amylase genes at early stages. The synthesis of gibberellins in the embryo ceased 4 to 5 days after germination (FIG. 28) due to inhibition by sugars transported from the endosperm (FIG. 24, panel B), but activation of α-amylase gene expression might be effective for several days during germination. At later stages, osmotic regulation of α-amylase production would become a more effective form of control because the osmotically active substances accumulate in a region of the endosperm immediately adjacent to the aleurone cells, whereas gibberellins have to be transported a considerable distance to the aleurone cells to be effective.

II. Transient Expression of αAmy3 and αAmy8 in the Embryo Correlates with Depletion and Replenishment of Sugars The evidence presented here supports the notion that the expression of αAmy3 and αAmy8 is suppressed by sugars transported from the endosperm via a feed-back control mechanism. Karrer and Rodriguez (1992, supra) have demonstrated that the expression of αAmy3 (Amy3D) in isolated rice embryos is suppressed by endosperm extracts of germinating rice seeds and by pure sugars. However, they did not observe the transient expression of αAmy8 (Amy3E) in the germinating rice embryo (Karrer et al (1991), supra). The decline in levels of αAmy3 and αAmy8 mRNA (FIGS. 23A and 23B) correlated with the elevation of sugar levels in the germinating embryos (FIG. 24, panel B).

Glucose has been shown to constitute more than half of the total soluble sugars derived from the hydrolysis of starch in the endosperms of germinating rice and barley seeds. If the sugar concentrations were calculated based on the molecular weight of glucose, two days after germination-the concentration of sugars was 3.9 mg/g (approximately 30 mM) in the embryo (panel B of FIG. 24 and Table 5) and 8.7 mg/g (approximately 150 mM) in the endosperm (panel C of FIG. 24 and Table 5). Scutellum connects the embryonic axis and the endosperm, and is responsible for transport of soluble sugars and other nutrients from the endosperm into the growing embryonic axis.

Therefore, the local concentration of sugars transported from the endosperm and accumulated in the scutellar epithelium at day 2 could be high enough (between 30 to 150 mM) to suppress the expression of αAmy3 and αAmy8 in the scutellum. This notion is supported by the observation that 25 mM glucose was sufficient to suppress the expression of αAmy3 in the isolated embryo (FIG. 25B), while up to 100 mM of mannitol (a non-metabolizable sugar) was not enough to have any effect (data not shown). This result also indicates that the suppression of αAmy3 and αAmy8 expression by sugars would not merely due to osmotic changes. The apparent rise of sugar levels in the whole embryo extract was not detected until day 3 (FIG. 24, panel B), which might have been because whole embryo extract for sugar determination was used. Induction of actin gene expression by 100 and 300 mM glucose (FIG. 25A, panel e) indicates that suppression of α-amylase gene expression was also not due to a general inhibition of gene expression and demonstrates the specificity of sugar metabolite regulation.

III. α-Amylase Genes Respond Differentially to Sugar Concentrations in the Enbryo and Aleurone Cells The differences in timing and magnitude of the rise and fall of α-amylase mRNA levels in embryo and aleurone cells suggest that the expression of various α-amylase genes is differentially regulated. In germinating embryos the level of αAmy7 mRNA continued to increase after the levels of αAmy3 and αAmy8 mRNA had fallen (FIGS. 23A and 23B) and the sugar content had risen (FIG. 24, panel B), suggesting that under the same conditions expression of αAmy7 might have been less sensitive to sugar suppression.

This hypothesis is supported by the observation that in the isolated embryo expression of αAmy7 was not inhibited by low concentrations (up to 100 mM) of glucose (FIG. 25A), whereas expression of αAmy3 was inhibited by glucose as low as 25 mM (FIG. 25B). Interestingly, αAmy7 was not expressed in isolated embryos germinated in water but its expression in these embryos was stimulated by 100 mM glucose (FIG. 25A, panel c). Nevertheless, a high concentration (300 mM) of glucose could inhibit the expression of αAmy7 in the isolated embryos. In cultured rice suspension cells, expression of αAmy7 is induced by sucrose starvation and suppressed by 100 mM sucrose in the medium (Sheu et al., manuscript in preparation), suggesting that the expression of αAmy7 in embryos is regulated differently from in suspension cells.

The concentrations of hydrolysis products in the endosperm ranged between 360 and 550 mM from days 5 to 8 after germination (Table 5B). In the aleurone, expression of αAmy8 was inhibited by glucose or mannitol at concentrations ≧300 mM, whereas the expression of αAmy7 was not inhibited (FIG. 26). This suggests that expression of αAmy7 might be less sensitive to the osmotic inhibition exerted by high concentrations of solutes in the endosperm. It may also explain why in the aleurone level of αAmy7 mRNA was not altered when levels of the other α-amylase mRNAs declined after reaching a first peak on day 5 (FIGS. 22A and 22B).

The above results-suggest that the alternate and/or differential expression of α-amylase genes in the embryo and aleurone during germination is due to differences in their sensitivities to sugar metabolites and osmotic stress. The differential sensitivities of α-amylase genes to sugar concentrations provides a potential mechanism for altering the pattern of enzyme distribution in response to changing carbohydrate status and requirement for sugars in embryo and endosperm during germination and seedling elongation. It has been proposed that the early expression of αAmy3 (Amy3D) followed by later isozymes (αAmy7 or Amy1A) may be an important part of the transition from germination to seedling elongation in rice (Thomas and Rodriguez, Plant Physiol. 106: 1235–1239, 1994).

IV. Sugars Regulate the Synthesis of Gibberellins in Embryos

In our germinating rice seeds, the level of gibberellins released by the embryo increased with time and peaked at day 3 (FIG. 28), a result similar to that reported for germinating barley seeds. Treatment of scutellum with sugars prevents the production of gibberellins. In this report the decline in gibberellin concentration correlated with the elevation of sugar concentration in embryos (FIG. 24, panel B), presumably because sugars transported from the endosperm also suppress the production of gibberellins.

It is found found that application of 50 mM glucose to the germinating seeds prevented the production of gibberellins in the embryos. Concentrations of mannitol up to 100 mM did not affect the accumulation of gibberellins (data not shown), suggesting that the suppression of gibberellin production by sugars was not due to osmotic changes. In the embryo, 50 mM glucose dramatically affected both α-amylase gene expression and gibberellin production. However, in the aleurone, only concentrations of glucose above 300 mM were effective in preventing the response of α-amylase genes to gibberellins. Thus, a model is proposed in which sugars regulate the expression of α-amylase genes and synthesis of gibberellins in the embryo via a metabolite feedback control mechanism, but regulate the expression of α-amylase genes in the aleurone via an osmotic control mechanism.

V. A Feedback and Osmotic Control Loop in Germinating Cereal Grain

The concept of a feedback control loop controlling gibberellin levels has been proposed for germinating barley. On the basis of our studies, we would redefine the control loop connecting embryo and endosperm of a germinating cereal grain as a loop comprising control of both gibberellin production and α-amylase gene expression by sugar metabolites and osmotic stress. In this control loop, active metabolism commences and respiration rate rises rapidly following hydration of the dry seed. The substrates consumed in respiratory metabolism during the early period of germination are sugars or oligosaccharides, which cause a rapid drop in the level of sugars in the scutellum.

Depletion of sugars in the scutellum may trigger the expression of αAmy3 and αAmy8 and degradation of starch in this tissue, and onset of gibberellin production and release into the endosperm. It is also possible that the pre-existing gibberellins in the embryo trigger the expression of αAmy3 and αAmy8 in the scutellum. The breakdown of endosperm starch begins initially in the region immediately adjacent to the scutellar epithelium and later in regions under the aleurone layers (Okamoto et al., Plant Cell Physiol. 21: 201–204, 1980).

Figure 29:
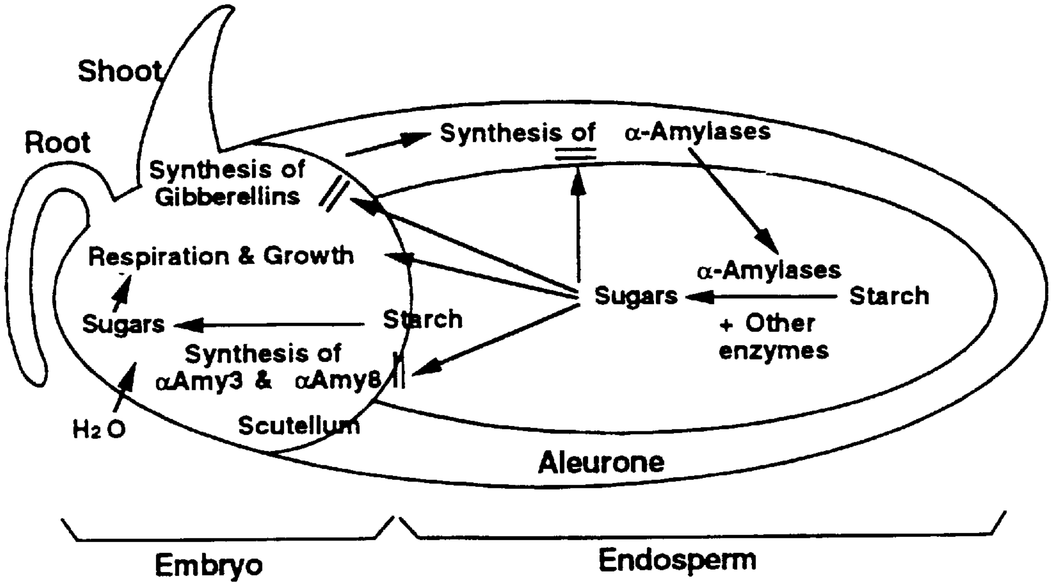
FIG. 29 provides a scheme illustrating the interactions among sugars, -gibberellins, and α-amylase genes in rice grains following germination. Imbibition of seed with water→Depletion of sugars in embryo→expression of αAmy3 and αAmy8 in scutellum, hydrolysis of starch in scutellum, and production and release of gibberellins by embryo→expression of α-amylase genes in aleurone cells triggered by gibberellins→hydrolysis of endosperm starch first by α-amylases secreted from the scutellum and later by α-amylases secreted from the aleurone cells→release of soluble sugars→sugars taken up by the scutellum that causes rise of sugar levels in embryo→sugars turn off expression of αAmy3 and αAmy8 and production of gibberellins in embryo→sugars osmotically regulate the expression of α-amylase genes in aleurone cells.

As hydrolysis products from the endosperm reach the embryo, sugar reserves in the scutellum are restored. This coincides with, and is thought to be the cause of, the cessation of αAmy3 and αAmy8 expression and gibberellin production. Endosperm starch is gradually hydrolyzed by α-amylases synthesized and secreted by aleurone cells and a high concentration of hydrolysis products in turn suppresses the expression of α-amylase genes in aleurone cells. A summary of the feedback and osmotic control loop is shown in FIG. 29. related metabolites that accumulate in the embryo and endosperm during germination serve as regulatory signals and osmotica to directly or indirectly control the expression of α-amylase genes and metabolic activities. These regulatory mechanisms presumably act to control the rate of starch hydrolysis in the scutellum and the endosperm to match the rate of sugar transport and supply to the growing young seedling. Vigorous seedling growth relies indispensably on a functional communication between the embryo and endosperm for allocation of sugars and starch in these tissues. We believe that this communication operates via sugars and gibberellins as signalling messengers and contributes to the multiple mechanisms that regulate the expression of α-amylase genes in cereal grains.

EXAMPLE VII

Production of Glucoamylase in Transgenic Rice Seeds

A. Cloning of glucoamylase gene from Rhizopus sp.

The fungus Rhizopus produces large amounts of glucoamylase which has extremely strong hydrolyzing activity toward raw starch. The nucleotide sequence of glucoamylase cDNA and genomic DNA of *Rhizopus oryzae* has been published (Ashikari et al., Agric. Biol. Chem. 50: 957–964, 1986). According to the nucleotide sequence of glucoamylase cDNA, the 5' and 3' primers which locate right upstream of the initiation codon ATG and right down stream of the termination codon TAA, were designed. The total cellular RNA was isolated from *R. oryzae* mycelia by the method of Verwoerd et al. (1989) and digested with RNase-free DNase I to remove any DNA contamination. The total cellular RNA and the two primers were used for reverse transcription—polymerase chain reaction (RT-PCR) of glucoamylase cDNA using the BRL MMLV reverse transcriptase. The derived DNA fragment was subcloned into the EcoRI site of pBR322. DNA sequencing was performed to confirm that the cloned DNA fragment is glucoamylase cDNA.

B. Expression of Glucoamylase Gene in Yeasts

Figure 31A:
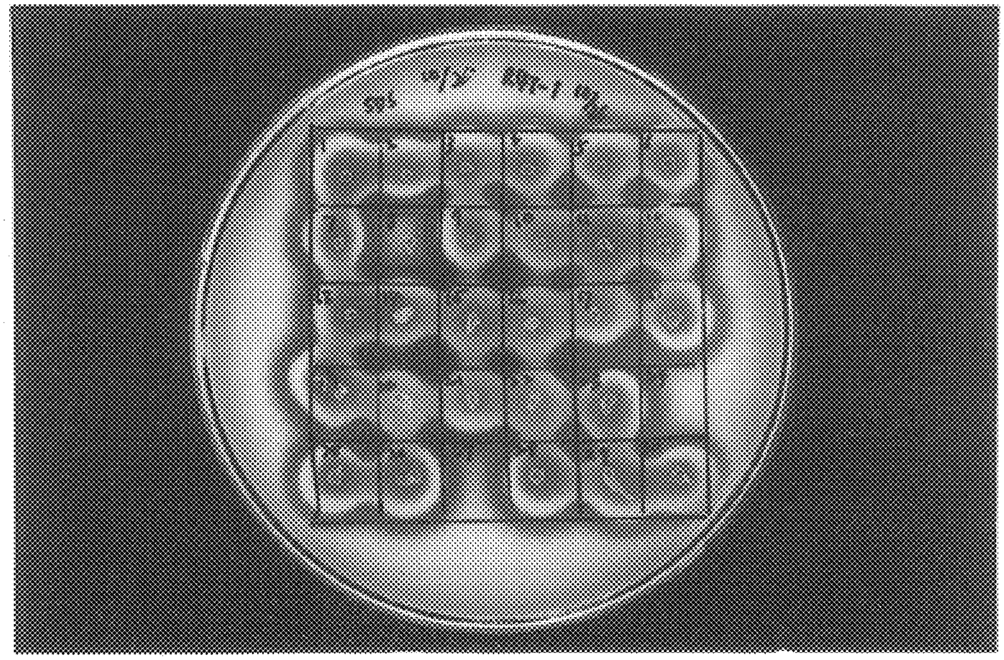
FIGS. 31A and 31B show starch-clearing zone plate assay for glucoamylase and α-amylase expression. Yeasts transformed with the glucoamylaase gene (FIG. 31A) or αAmy3 (FIG. 31B) was grown in YPDS medium and incubated at 30° C. for 10 days.
Figure 31B:
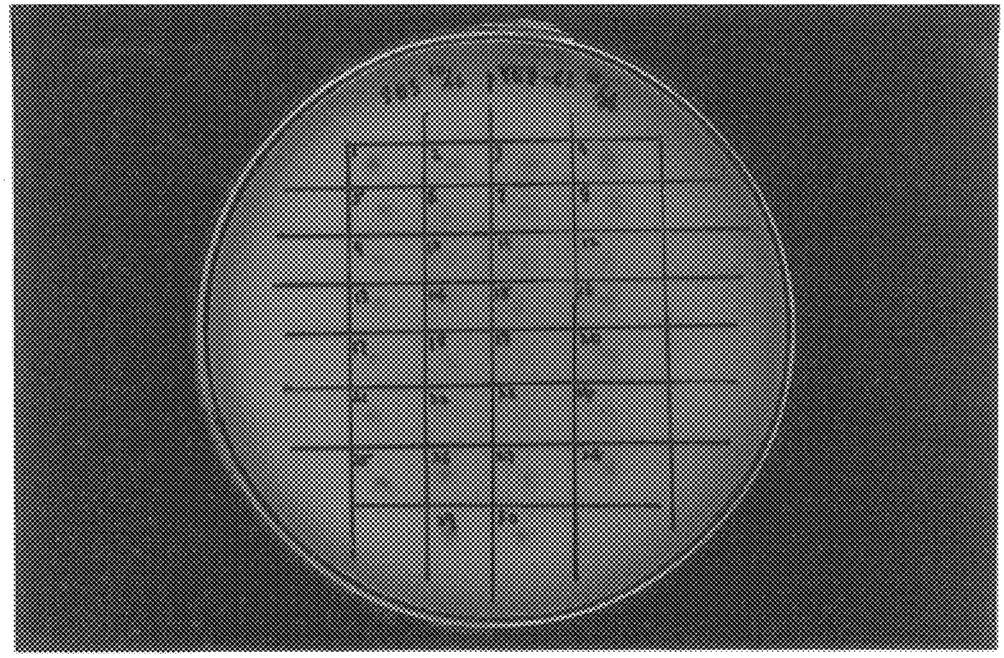

It takes much of work and time to transform rice and obtain transgenic rice. Before doing transformation of rice, it is intended to express the cloned glucoamylase cDNA in yeast first in order to test the starch hydrolyzing activity of said enzyme. The glucoamylase cDNA was excised from pBR322, subcloned into the yeast expression vector pYE8 (FIG. 30A), and expressed under the control of GAP promoter. The derived plasmid, designated as R4T-1, was delivered into yeast strain 20B12 (matα, trp1, pep4). The transformed yeasts were first selected on SDS medium (containing yeast nitrogen base 0.45 g; ammonium sulfate, 6.25 g; dextrose, 20 g; and potato soluble starch 15 g in 1 L), then subcultured on YPDS medium (containing yeast extract, 10 g; peptone 20 g; dextrose 20 g; potato soluble starch, 15 g; and agar, 18 g in 1 L) for a few days, and stained with iodine vapor. Because the Rhizopus glucoamylase cDNA contains a signal peptide sequence, the expressed glucoamylase should be secreted extracellularly. Yeast colonies which secreted glucoamylase and hydrolyzed starch form starch-clearing zones in agar plate.

cDNA of a rice α-amylase gene, αAmy3, was also subcloned into pYE8 and the derived plasmid was designated as pYE8-C3 (FIG. 30B) and expressed in yeasts. Comparison of the sizes of the starch-clearing zones formed during the same incubation time indicating that the Rhizopus glucoamylase has much higher starch hydrolytic activity than the α-amylase encoded by the rice αAmy3 gene (FIGS. 31A and 31B).

C. Expression of Glucoamylase Gene in Rice Seed

After confirming that the Rhizopus glucoamylase gene encodes an enzyme which has very high starch hydrolyzing activity, next, transformation of rice with this glucoamylase gene is to be conducted. The glucoamylase gene is inserted into the protein expression cassette pA8H(2)-A, designated as pGA-2 (FIGS. 32A and 32B), and delivered into rice via the Agrobacterium-mediated transformation. Secretion and activity of glucoamylase expressed in the transgenic rice callus is to be tested on MS medium containing starch. Transgenic cell lines expressing the glucoamylase gene will be regenerated and seeds of the transgenic plants will be harvested.

Because the glucoamylase gene in rice is fused downstream of the α-amylase promoter and signal sequence, it should be expressed in the aleurone cells during seed germination and secreted into the starchy endosperm as endogenous α-amylases. It is very likely that the endosperm starch will be rapidly hydrolyzed during germination due to the expression of both glucoamylase and endogenous α-amylases. The α-amylase from black mold (*Aspergillus awamori*) alone had only a weak activity against raw starch but together with glucoamylase the activity was about three times the sum of their separate actvitics (Ueda (1981), supra).

The Bacillus α-amylase overexpressed in tobacco was properly secreted into the intercellular space and the expression level was about 0.3% of total soluble protein (Pen et al (1992), supra). No apparent effect of the he presence of α-amylase on tobacco plant phenotype was observed. Therefore, the transgenic rice overexpressing glucoamylase may also have no much effect on the growth of the plant. As such, the ultimate goal of the instant invention, i.e. the application of such a novel rice variety in industrial glucose production and alcohol fermentation, can be readily accomplished according to the Examples. The same approach may also be applied for transformation of barley and maize that are other major cereals for the production of glucose and beer in industry.

From the above teachings, it is apparent that various modifications and variations can be made without daparting from the spirit and scope of the present invention. It is therefore to be understood that this invention may be practiced otherwise than as specifically described.

TABLE 1

Relative accumulation of α-amylase mRNA in germinating rice seeds as detected by α-amylase gene-specific probes.

| | Days after germination | | | | | |
|---|---|---|---|---|---|---|
| Probes | 1 | 2 | 3 | 4 | 5 | 6 |
| OSamy-c | 0[a] | 25 | 73 | 100 | 67 | 47 |
| αAmy6-C-3' | 0 | 23 | 73 | 100 | 27 | 26 |
| αAmy7-C-3' | 0 | 26 | 72 | 100 | 50 | 48 |
| αAmy8-C-3' | 0 | 31 | 98 | 100 | 27 | 23 |
| αAmy10-C-3' | 0 | 23 | 64 | 100 | 47 | 44 |

[a]Level of α-amylase mRNA was determined by densitometric scanning of the autoradiograms shown in FIG. 6A, and corrected with the mRNA level of pcRAc1.3. The relative mRNA accumulation for each α-amylase gene was then determined by dividing the α-amylase mRNA level of each day by the mRNA level (peak level) of day 4.

TABLE 2

Relative accumulation of α-amylase mRNA in cultured suspension cells of rice at later growth stages as detected by α-amylase gene-specific probes.

| | Days in culture | | | |
|---|---|---|---|---|
| Probes | 8 | 10 | 12 | 14 |
| OSamy-c | 1.0[a] | 3.6 | 39.5 | 39.8 |
| αAmy6-C-3' | 1.0 | 1.3 | 4.1 | 1.2 |
| αAmy7-C-3' | 1.0 | 1.8 | 6.2 | 9.8 |
| αAmy8-C-3' | 1.0 | 2.2 | 37.0 | 44.5 |
| αAmy10-C-3' | 1.0 | 1.3 | 1.2 | 5.0 |

[a]Level of α-amylase mRNA was determined by densitometric scanning of the autoradiograms shown in FIG. 6B, and corrected with the mRNA level of pOScx-3'. The relative mRNA accumulation for each α-amylase gene was then determined by dividing the α-amylase mRNA level of each day by the mRNA level (basal level) of day 8.

TABLE 3

Effect of PSC on the efficiency of rice transformation by Agrobacterium

| Agrobacterium Strains | Addition of PSC | No. of immature embryos inoculated | No. of Transgenic callus | No. of Transgenic plant | Frequency for induction of transgenic callus (%) | Frequency for induction of transgenic plants (%) |
|---|---|---|---|---|---|---|
| A281 (pAG8) | + | 250 | 17 | 4 | 0.8 | 1.6 |
| A281 (pAG8) | − | 60 | 2 | 0 | 2.5 | 0 |

*PSC = potato suspension culture

TABLE 4

Yield of GUS produced by suspension cells of different transgenic plant species.

| Transgenic cell lines[1)] | Yield[2)] in cell medium (μg/g) | % of Total protein[3)] |
|---|---|---|
| Rice (Tainung 62) | | |
| C7 | 135 | 10 |
| C11 | 156 | 10 |

TABLE 4-continued

Yield of GUS produced by suspension cells of different transgenic plant species.

| Transgenic cell lines[1)] | Yield[2)] in cell medium (μg/g) | % of Total protein[3)] |
|---|---|---|
| Rice (Tainan 5) | | |
| C51 | 370 | 40 |
| C52 | 303 | 40 |
| Tobacco | | |
| TO1 | 163 | 25 |
| TO2 | 150 | 15 |
| Potato | | |
| P1 | 30 | 15 |
| P2 | 33 | 20 |

[1)]Suspension cells were grown in sucrose-free medium for 2 days. Proteins were collected from the culture medium, fractionated by SDS-PAGE, and analyzed by Western blot analysis using the GUS antibodies. GUS was quantified by comparison with known amount of purified *E. coli* GUS loaded on the same gel.
[2)]Yield = total amount of GUS colleced from culture medium/total fresh weight of cells collected.
[3)]% of Total protein = total amount of GUS collected from culture medium/total amount of proteins collected from culture medium.

TABLE 5

Estimatian of the fresh weight, sugar content, water content, and glucose concentration of embryo (Em) from germinating rice seeds.

| | Fresh weight | Sugar[a] | | Water[b] | | Glucose[c] conc. |
|---|---|---|---|---|---|---|
| Day | mg/Em | mg/g | mg/Em | % | mg/Em | mM |
| 0.5 | 2.22 | 6.4 | 0.01 | 63.1 | 1.40 | 50 |
| 1 | 1.93 | 3.9 | 0.01 | 75.1 | 1.45 | 30 |
| 2 | 3.85 | 3.9 | 0.02 | 78.7 | 3.03 | 28 |
| 3 | 5.12 | 5.4 | 0.03 | 84.2 | 4.31 | 36 |
| 4 | 5.57 | 5.9 | 0.03 | 78.5 | 4.37 | 42 |
| 5 | 6.28 | 7.0 | 0.04 | 80.1 | 5.03 | 49 |
| 6 | 7.21 | 8.8 | 0.06 | 78.8 | 5.68 | 61 |

TABLE 5-continued

Estimatian of the fresh weight, sugar content, water content, and glucose concentration of embryo (Em) from germinating rice seeds.

| | Fresh weight | Sugar[a] | | Water[b] | | Glucose[c] conc. |
|---|---|---|---|---|---|---|
| Day | mg/Em | mg/g | mg/Em | % | mg/Em | mM |
| 7 | 7.22 | 7.9 | 0.06 | 76.6 | 5.53 | 58 |
| 8 | 7.24 | 7.8 | 0.06 | 74.6 | 5.40 | 58 |

TABLE 6

Estimation of the fresh weight, sugar content, water content, and glucose concentration of endosperm (End) from germinating rice seeds.

| | Fresh weight | Sugar[a] | | Water[b] | | Glucose[c] conc. |
|---|---|---|---|---|---|---|
| Day | mg/End | mg/g | mg/End | % | mg/End | mM |
| 0.5 | 25.8 | 4.4 | 0.11 | 29.7 | 7.66 | 82 |
| 1 | 25.7 | 4.1 | 0.11 | 28.1 | 7.21 | 81 |
| 2 | 24.3 | 8.7 | 0.21 | 31.5 | 7.65 | 152 |
| 3 | 22.5 | 12.8 | 0.29 | 33.7 | 7.58 | 211 |
| 4 | 21.6 | 30.5 | 0.66 | 38.3 | 8.26 | 441 |
| 5 | 18.5 | 51.2 | 0.95 | 51.6 | 9.55 | 548 |
| 6 | 18.1 | 48.9 | 0.89 | 57.9 | 10.49 | 468 |
| 7 | 16.5 | 50.7 | 0.84 | 60.0 | 9.90 | 470 |
| 8 | 15.3 | 48.6 | 0.74 | 74.1 | 11.34 | 366 |

Fifty seeds were germinated in water for various lengths of time. Embryos and endosperms were separated after germination.
[a]Determined with a method described previously (Chen et al., 1994).
[b]Water content = fresh weight − dry weight. % = water content/fresh weight.
[c]Since glucose is the predominant soluble sugar in germinating rice seeds (Murata et al., 1968), glucose concentration is estimated by dividing sugar content with water content and molecular weight (180) of glucose.

What is claimed is:

1. A method for producing a transgenic monocot plant, comprising the steps of:

transforming an immature embryo of a monocot plant via Agrobacterium-mediated transformation with a DNA expressible in cells of said immature monocot embryo, wherein said DNA comprises plant α-amylase gene promoter and signal peptide-encoding sequences operatively connected to an exogenous sequence encoding a desired gene product, wherein said promoter is induced under a sugar-depleted or sugar-free condition to promote expression of said exogenous sequence, and wherein the transforming step is enhanced by co-culture with a dicot suspension culture;

regenerating a transgenic monocot plant from said transformed embryo; and growing the transgenic monocot plant whereby at least a part of said transgenic monocot plant expresses said gene product under a sugar-depleted or sugar-free condition.

2. A method according to claim 1, wherein the dicot suspension culture is a potato suspension culture.

3. A method for producing a transgenic monocot plant, comprising the steps of:

transforming an immature embryo of a monocot plant via Agrobacterium-mediated transformation with a DNA expressible in cells of said immature monocot embryo, wherein said DNA comprises plant α-amylase gene promoter and signal peptide-encoding sequences operatively connected to an exogenous sequence encoding a desired gene product, and wherein said promoter is induced under a sugar-depleted or sugar-free condition to promote expression of said exogenous sequence;

regenerating a transgenic monocot plant from said transformed embryo; and growing the transgenic monocot plant whereby at least a part of said transgenic monocot plant expresses said gene product under a sugar-depleted or sugar-free condition.

4. A method for producing a gene product, comprising the steps of:

cultivating angiosperm host cell, said host cell comprising a chimeric gene, said chimeric gene comprising a promoter sequence derived from an α-anylase gene of a plant operably connected to a nucleotide sequence encoding a desired gene product, wherein expression of said chimeric gene is induced by a sugar-depleted or sugar-free condition;

subjecting said cultivated host cell to a sugar-depleted or sugar free condition to promote expression of said chimeric gene; and recovering the desired gene product.

5. A method according to claim 4 wherein said chimeric gene further comprises a sequence encoding an α-amylase signal peptide fused in-frame with the sequence encoding the desired gene product.

6. A method according to claim 4 wherein said promoter sequence is selected from the group consisting of the αAmy6-C, αAmy7-C, αAmy8-C, and αAmy10-C promoters from *Oryza sativa.*

* * * * *

UNITED STATES PATENT AND TRADEMARK OFFICE
CERTIFICATE OF CORRECTION

PATENT NO. : 6,288,302 B1
DATED : September 11, 2001
INVENTOR(S) : Su-May Yu, Li-Fei Liu and Ming-Tsair Chan It is certified that error appears in the above-identified patent and that said Letters Patent is hereby corrected as shown below:

<u>Column 84,</u>
Line 46, "cultivating angiosperm host cell" should read -- cultivating an angiosperm host cell --.
Line 48, "α-anylase" should read -- α-amylase --.

Signed and Sealed this

Twenty-first Day of May, 2002

*Attest:*

JAMES E. ROGAN
*Director of the United States Patent and Trademark Office*

*Attesting Officer*